(12) United States Patent
Jimenez et al.

(10) Patent No.: US 9,072,371 B2
(45) Date of Patent: Jul. 7, 2015

(54) ORAL CARE SYSTEM, KIT AND METHOD

(75) Inventors: Eduardo Jimenez, Manalapan, NJ (US); Sharon Kennedy, Randallstown, MD (US); Robert Moskovich, East Brunswick, NJ (US); John Gatzemeyer, Hillsborough, NJ (US); Gary L. Berge, Crystal Lake, IL (US); Suman Kumar Chopra, Monroe, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 870 days.

(21) Appl. No.: 13/254,447

(22) PCT Filed: Dec. 16, 2010

(86) PCT No.: PCT/US2010/060867
§ 371 (c)(1),
(2), (4) Date: Sep. 1, 2011

(87) PCT Pub. No.: WO2011/079027
PCT Pub. Date: Jun. 30, 2011

(65) Prior Publication Data
US 2011/0314623 A1    Dec. 29, 2011

Related U.S. Application Data

(63) Continuation-in-part of application No. PCT/US2009/069408, filed on Dec. 23, 2009, and a continuation-in-part of application No. PCT/US2009/069402, filed on Dec. 23, 2009.
(Continued)

(51) Int. Cl.
*A46B 11/00* (2006.01)
*A61C 19/06* (2006.01)

(52) U.S. Cl.
CPC ....... *A46B 11/0024* (2013.01); *Y10T 29/49826* (2015.01); *A46B 11/0027* (2013.01);
(Continued)

(58) Field of Classification Search
USPC ............ 401/83, 118, 123–125, 154, 172–175
See application file for complete search history.

(56) References Cited

U.S. PATENT DOCUMENTS

| 64,732 A | 5/1867 | Wylie |
| 261,456 A | 7/1882 | Hoffman |

(Continued)

FOREIGN PATENT DOCUMENTS

| CN | 201025977 | 2/2008 |
| DE | 2725495 | 12/1977 |

(Continued)

OTHER PUBLICATIONS

International Search Report and Written Opinion in International Application No. PCT/US10/60881 mailed May 16, 2011.
(Continued)

*Primary Examiner* — David Walczak
*Assistant Examiner* — Bradley Oliver
(74) *Attorney, Agent, or Firm* — Ryan M. Flandro

(57) ABSTRACT

An oral care system and method for applying a fluid to an oral surface, including a method of manufacturing the same. In one embodiment, the invention can be an oral care system comprising: a toothbrush; and a dispenser detachably coupled to the toothbrush, the dispenser comprising: an internal reservoir containing a fluid; and a conduit in fluid communication with the reservoir and terminating in an orifice for dispensing the fluid; and a plug having a proximal plug portion disposed within the conduit and a distal plug portion disposed within a socket of the toothbrush.

24 Claims, 29 Drawing Sheets

Related U.S. Application Data

(60) Provisional application No. 61/410,514, filed on Nov. 5, 2010, provisional application No. 61/423,397, filed on Dec. 15, 2010, provisional application No. 61/423,414, filed on Dec. 15, 2010, provisional application No. 61/423,435, filed on Dec. 15, 2010, provisional application No. 61/423,449, filed on Dec. 15, 2010.

(52) U.S. Cl.
CPC ......... *A46B11/0034* (2013.01); *A46B 11/0065* (2013.01); *A46B 2200/1066* (2013.01); *A61C 19/066* (2013.01)

(56) References Cited

U.S. PATENT DOCUMENTS

| | | |
|---|---|---|
| 766,556 A | 8/1904 | Symonds |
| 1,062,480 A | 5/1913 | Larocque |
| 1,244,324 A | 10/1917 | Hackley |
| 1,292,416 A | 1/1919 | Auld |
| 1,546,516 A | 7/1925 | Smith |
| 1,555,064 A | 9/1925 | La Mothe |
| 1,668,511 A | 5/1928 | McLaughlin |
| 1,701,030 A | 2/1929 | Collins |
| 1,746,474 A | 2/1930 | Hogner |
| 1,913,528 A | 6/1933 | White |
| 1,975,723 A | 10/1934 | Johnssen |
| 2,068,213 A | 1/1937 | Wilson |
| 2,247,003 A | 6/1941 | Smith et al. |
| D134,723 S | 1/1943 | Riksheim |
| 2,356,874 A | 8/1944 | Nageotte |
| 2,399,660 A | 5/1946 | Boulicault |
| 2,437,769 A | 3/1948 | Traylor |
| 2,438,641 A | 3/1948 | Loehr |
| 2,445,571 A | 7/1948 | Fuston |
| 2,448,033 A | 8/1948 | Kruck |
| 2,521,882 A | 9/1950 | Swift et al. |
| 2,541,949 A | 2/1951 | Thacker et al. |
| 2,579,899 A | 12/1951 | Burrows |
| 2,637,060 A | 5/1953 | Cowan |
| 2,670,881 A | 3/1954 | Sjoblom |
| 2,676,568 A | 4/1954 | Maczynski |
| 2,718,299 A | 9/1955 | Atwater et al. |
| 2,771,858 A | 11/1956 | Cribbs et al. |
| 2,800,899 A | 7/1957 | Barron |
| 2,845,645 A | 8/1958 | Wishnefsky et al. |
| 2,885,110 A | 5/1959 | Tregilgas |
| 2,885,116 A | 5/1959 | Tregilgas |
| 2,968,827 A | 1/1961 | Leo et al. |
| 3,108,687 A | 10/1963 | Dayton |
| 3,148,684 A | 9/1964 | Keeler |
| 3,181,539 A | 9/1964 | Keeler |
| 3,187,758 A | 6/1965 | Eklund |
| 3,215,320 A | 11/1965 | Heisler et al. |
| 3,293,749 A | 12/1966 | George et al. |
| 3,296,642 A | 1/1967 | Aylott |
| 3,358,699 A | 12/1967 | Bau |
| 3,359,991 A | 12/1967 | Spatz |
| 3,359,992 A | 12/1967 | Cishek et al. |
| 3,378,176 A | 4/1968 | Snyder |
| 3,406,694 A | 10/1968 | Odence |
| 3,468,612 A | 9/1969 | Aston |
| 3,683,924 A | 8/1972 | Louie |
| 3,910,706 A | 10/1975 | Del Bon |
| 3,986,645 A | 10/1976 | Baldwin et al. |
| 4,068,974 A | 1/1978 | Meyer |
| 4,201,491 A | 5/1980 | Kohler |
| 4,275,750 A | 6/1981 | Clark |
| 4,277,194 A | 7/1981 | Smith |
| 4,296,518 A | 10/1981 | Furrier et al. |
| 4,323,157 A | 4/1982 | Idec |
| 4,331,267 A | 5/1982 | Duncan et al. |
| 4,340,367 A | 7/1982 | Vadas et al. |
| 4,350,712 A | 9/1982 | Kocharian et al. |
| 4,384,645 A | 5/1983 | Manfredi |
| 4,413,760 A | 11/1983 | Paton |
| 4,506,810 A | 3/1985 | Goncalves |
| 4,527,574 A | 7/1985 | Manfredi |
| 4,543,679 A | 10/1985 | Rosofsky et al. |
| 4,573,820 A | 3/1986 | Kirchhoff |
| 4,582,059 A | 4/1986 | Tiwari |
| 4,594,015 A | 6/1986 | Pomares |
| 4,641,766 A | 2/1987 | Vlasich |
| 4,655,372 A | 4/1987 | Ross et al. |
| 4,659,327 A | 4/1987 | Bennett et al. |
| 4,662,385 A | 5/1987 | Schefer |
| 4,763,815 A | 8/1988 | Von Schuckmann et al. |
| 4,767,032 A | 8/1988 | Smith |
| 4,776,717 A | 10/1988 | Iizuka et al. |
| 4,808,022 A | 2/1989 | Iizuka et al. |
| 4,826,341 A | 5/1989 | Kwak |
| 4,865,481 A | 9/1989 | Scales |
| 4,866,809 A | 9/1989 | Pelletier |
| 4,874,117 A | 10/1989 | Kay et al. |
| 4,879,781 A | 11/1989 | Desimone |
| 4,886,186 A | 12/1989 | Andris |
| 4,887,924 A | 12/1989 | Green |
| 4,892,427 A | 1/1990 | Ford |
| D310,308 S | 9/1990 | Wolsey |
| 4,954,000 A | 9/1990 | Gueret |
| 4,997,299 A | 3/1991 | Ohba |
| 5,000,356 A | 3/1991 | Johnson et al. |
| 5,011,317 A | 4/1991 | Gueret |
| 5,016,782 A | 5/1991 | Pfanstiel |
| 5,018,892 A | 5/1991 | Krueckel et al. |
| 5,028,158 A | 7/1991 | Fey |
| 5,066,155 A | 11/1991 | English et al. |
| 5,156,479 A | 10/1992 | Iizuka |
| 5,199,807 A | 4/1993 | Uchida |
| 5,217,475 A | 6/1993 | Kuber |
| 5,234,136 A | 8/1993 | Kopis |
| 5,244,298 A | 9/1993 | Greenhouse |
| 5,249,876 A | 10/1993 | Hattman |
| 5,294,205 A | 3/1994 | Moeck et al. |
| 5,336,005 A | 8/1994 | Moeck et al. |
| 5,403,105 A | 4/1995 | Jameson |
| 5,423,623 A | 6/1995 | Bakic |
| 5,425,591 A | 6/1995 | Contreras et al. |
| 5,454,660 A | 10/1995 | Sakurai et al. |
| 5,540,361 A | 7/1996 | Fattori |
| 5,547,302 A | 8/1996 | Dornbusch et al. |
| 5,560,518 A | 10/1996 | Catterall et al. |
| 5,569,278 A | 10/1996 | Persad |
| 5,573,341 A | 11/1996 | Iaia |
| 5,608,940 A | 3/1997 | Panyon, Jr. |
| 5,611,687 A | 3/1997 | Wagner |
| 5,695,788 A | 12/1997 | Woods |
| 5,697,531 A | 12/1997 | Fattori |
| 5,709,004 A | 1/1998 | Paduano et al. |
| 5,725,133 A | 3/1998 | Iaia |
| 5,733,058 A | 3/1998 | Hofmann |
| 5,765,573 A | 6/1998 | Gueret |
| 5,772,347 A | 6/1998 | Gueret |
| 5,791,801 A | 8/1998 | Miller |
| 5,803,640 A | 9/1998 | Nakajima et al. |
| 5,827,002 A | 10/1998 | Nakajima |
| 5,827,308 A | 10/1998 | Thakur et al. |
| 5,839,622 A | 11/1998 | Bicknell et al. |
| 5,851,079 A | 12/1998 | Horstman et al. |
| 5,860,572 A | 1/1999 | Harrold et al. |
| 5,862,817 A | 1/1999 | Lee |
| 5,879,095 A | 3/1999 | Gueret |
| 5,893,860 A | 4/1999 | Ripich et al. |
| 5,911,532 A | 6/1999 | Evancic |
| 5,916,228 A | 6/1999 | Ripich et al. |
| 5,941,254 A | 8/1999 | Heler |
| 5,955,114 A | 9/1999 | Llanos |
| 5,970,990 A | 10/1999 | Dunton et al. |
| 5,980,145 A | 11/1999 | Griffith |
| 5,996,850 A | 12/1999 | Morali et al. |
| 6,015,293 A | 1/2000 | Rimkus |
| 6,039,053 A | 3/2000 | Turrentine |
| 6,056,469 A | 5/2000 | Algorri |
| 6,056,763 A | 5/2000 | Parsons |
| 6,070,598 A | 6/2000 | Gueret |

(56) References Cited

U.S. PATENT DOCUMENTS

| | | | |
|---|---|---|---|
| 6,071,026 A | 6/2000 | Martinez et al. |
| 6,082,918 A | 7/2000 | Gueret |
| 6,086,276 A | 7/2000 | Gueret |
| 6,099,315 A | 8/2000 | Markowitz |
| 6,200,055 B1 | 3/2001 | Fusaro, Jr. |
| 6,202,247 B1 | 3/2001 | Lorenz, Jr. |
| 6,210,061 B1 | 4/2001 | Johnson |
| 6,213,662 B1 | 4/2001 | Aljanedi |
| 6,220,773 B1 | 4/2001 | Wiegner et al. |
| 6,224,573 B1 | 5/2001 | Yeager et al. |
| 6,227,209 B1 | 5/2001 | Kim et al. |
| 6,238,117 B1 | 5/2001 | Griebel et al. |
| 6,290,417 B1 | 9/2001 | Kaminski |
| 6,325,076 B1 | 12/2001 | Ramirez |
| 6,331,085 B1 | 12/2001 | Schrepf et al. |
| 6,345,629 B1 | 2/2002 | Vives |
| 6,363,949 B1 | 4/2002 | Brown |
| 6,368,001 B1 | 4/2002 | Roeder |
| 6,398,439 B1 | 6/2002 | Szekely |
| 6,406,694 B1 | 6/2002 | LaRosa |
| 6,439,885 B2 | 8/2002 | Antler |
| 6,440,149 B1 | 8/2002 | Potti |
| 6,450,716 B1 | 9/2002 | Szekely |
| 6,475,172 B1 | 11/2002 | Hall |
| 6,488,427 B1 | 12/2002 | Breidenbach et al. |
| 6,592,281 B2 | 7/2003 | Clark et al. |
| 6,607,323 B2 | 8/2003 | Breidenbach et al. |
| 6,647,581 B1 | 11/2003 | Persad et al. |
| 6,648,641 B1 | 11/2003 | Viltro et al. |
| 6,672,783 B1 | 1/2004 | Licata et al. |
| 6,688,317 B2 | 2/2004 | Gueret |
| 6,688,793 B2 | 2/2004 | Goyet |
| 6,688,796 B1 | 2/2004 | Lin |
| 6,745,781 B2 | 6/2004 | Gueret |
| 6,746,170 B2 | 6/2004 | Delage |
| 6,752,558 B1 | 6/2004 | Hsu |
| 6,824,018 B1 | 11/2004 | Eaddy et al. |
| 6,866,438 B2 | 3/2005 | Bauer et al. |
| 6,880,999 B2 | 4/2005 | Biegel et al. |
| 6,918,511 B1 | 7/2005 | Spatz et al. |
| 6,923,587 B2 | 8/2005 | Lee |
| 6,957,753 B2 | 10/2005 | Tani |
| 7,029,484 B2 | 4/2006 | Ripich |
| 7,044,671 B2 | 5/2006 | Parikh et al. |
| 7,051,642 B2 | 5/2006 | Kageyama |
| 7,055,527 B2 | 6/2006 | Tien |
| 7,086,564 B1 | 8/2006 | Corrigan |
| 7,086,796 B2 | 8/2006 | Severa |
| 7,089,564 B2 | 8/2006 | Chen et al. |
| 7,114,505 B2 | 10/2006 | Bauer et al. |
| 7,143,462 B2 | 12/2006 | Hohlbein |
| 7,144,175 B2 | 12/2006 | Biegel |
| 7,168,435 B2 | 1/2007 | Vieu et al. |
| 7,192,212 B2 | 3/2007 | Gutberlet et al. |
| 7,201,527 B2 | 4/2007 | Thorpe et al. |
| 7,210,870 B2 | 5/2007 | Breidenbach et al. |
| 7,217,054 B2 | 5/2007 | Noguchi |
| 7,226,231 B2 | 6/2007 | Py et al. |
| 7,237,974 B2 | 7/2007 | Pfenniger et al. |
| 7,237,975 B2 | 7/2007 | Noguchi |
| 7,264,471 B2 | 9/2007 | Malcmacher |
| 7,293,928 B2 | 11/2007 | Lane |
| 7,303,348 B2 | 12/2007 | Phipps et al. |
| 7,309,184 B2 | 12/2007 | Butcher et al. |
| 7,309,185 B2 | 12/2007 | Thorpe et al. |
| 7,331,731 B2 | 2/2008 | Hohlbein et al. |
| 7,347,360 B2 | 3/2008 | Lasch et al. |
| 7,374,360 B1 | 5/2008 | Szekely |
| 7,396,180 B2 | 7/2008 | Bugla et al. |
| 7,399,133 B1 | 7/2008 | Eversole |
| 7,401,373 B2 | 7/2008 | Tybinkowski et al. |
| 7,461,988 B2 | 12/2008 | Albisetti |
| 7,465,113 B2 | 12/2008 | Gueret |
| 7,474,048 B2 | 1/2009 | Forrest et al. |
| 7,481,591 B2 | 1/2009 | Dumler |
| 7,520,406 B2 | 4/2009 | Jaichandra et al. |
| 7,540,054 B2 | 6/2009 | Goldstein |
| 7,557,936 B2 | 7/2009 | Dickinson |
| 7,614,811 B2 | 11/2009 | Kaufman et al. |
| 7,641,411 B2 | 1/2010 | Biegel |
| 7,651,291 B2 | 1/2010 | Py et al. |
| 7,665,923 B2 | 2/2010 | Py et al. |
| 7,677,827 B1 | 3/2010 | Manukian |
| 7,823,593 B2 | 11/2010 | Gueret |
| 8,016,507 B2 | 9/2011 | Wright |
| 2002/0054783 A1 | 5/2002 | Gueret |
| 2002/0073496 A1 | 6/2002 | Kim |
| 2003/0012594 A1 | 1/2003 | Andersen |
| 2003/0057236 A1 | 3/2003 | Delage |
| 2004/0028456 A1 | 2/2004 | Giraldo |
| 2004/0092981 A1 | 5/2004 | Barlow et al. |
| 2004/0237996 A1 | 12/2004 | Fischer et al. |
| 2004/0240928 A1 | 12/2004 | Trocino |
| 2005/0006409 A1 | 1/2005 | Ganzeboom |
| 2005/0026774 A1 | 2/2005 | Nolan |
| 2005/0036821 A1 | 2/2005 | Pfenniger et al. |
| 2005/0069372 A1 | 3/2005 | Hohlbein et al. |
| 2005/0199655 A1 | 9/2005 | Petit |
| 2006/0058821 A1 | 3/2006 | Jansheski |
| 2006/0207627 A1 | 9/2006 | Thorpe et al. |
| 2006/0233588 A1 | 10/2006 | Gueret |
| 2006/0260635 A1 | 11/2006 | Dabney |
| 2006/0269351 A1 | 11/2006 | Mcafee |
| 2006/0269354 A1 | 11/2006 | Lane |
| 2006/0272666 A1 | 12/2006 | Wyatt et al. |
| 2006/0275225 A1 | 12/2006 | Prencipe et al. |
| 2007/0007302 A1 | 1/2007 | Jaichandra et al. |
| 2007/0079845 A1 | 4/2007 | Gueret |
| 2007/0227553 A1 | 10/2007 | Gueret |
| 2007/0231055 A1 | 10/2007 | Albisetti |
| 2007/0292194 A1 | 12/2007 | Albisetti et al. |
| 2008/0063464 A1 | 3/2008 | Prague |
| 2008/0089733 A1 | 4/2008 | Lochak |
| 2008/0189888 A1 | 8/2008 | Hohlbein |
| 2008/0274066 A1 | 11/2008 | Montgomery |
| 2009/0074679 A1 | 3/2009 | Silverman |
| 2009/0254055 A1 | 10/2009 | Clarke |
| 2009/0261007 A1 | 10/2009 | Sanchez |
| 2009/0288262 A1 | 11/2009 | Hall |
| 2009/0317432 A1 | 12/2009 | Kergosien |
| 2010/0168638 A1 | 7/2010 | Korogi et al. |
| 2010/0240013 A1 | 9/2010 | Levine |
| 2010/0284726 A1 | 11/2010 | Ottaviani et al. |
| 2011/0308030 A1 | 12/2011 | Jimenez et al. |
| 2012/0114410 A1 | 5/2012 | Jimenez et al. |
| 2012/0163902 A1 | 6/2012 | Jimenez et al. |

FOREIGN PATENT DOCUMENTS

| | | |
|---|---|---|
| DE | 3832224 | 8/1989 |
| DE | 29613012 | 10/1996 |
| EP | 0308549 | 3/1989 |
| EP | 0385815 | 9/1990 |
| EP | 1506726 | 2/2005 |
| ER | 1596074 | 6/1970 |
| FR | 850458 | 12/1939 |
| FR | 907669 | 3/1946 |
| FR | 2597734 | 10/1987 |
| GB | 666082 | 2/1952 |
| GB | 792448 | 3/1958 |
| GB | 1190280 | 4/1970 |
| GB | 2085717 | 5/1982 |
| GB | 2280361 | 2/1995 |
| GB | 2307674 | 6/1997 |
| GB | 2393642 | 4/2004 |
| JP | 48-093167 | 12/1973 |
| NL | 2002311 | 6/2010 |
| WO | WO 93/03648 | 3/1993 |
| WO | WO 96/01579 | 1/1996 |
| WO | WO 98/09572 | 3/1998 |
| WO | WO 98/18695 | 5/1998 |
| WO | WO 01/00103 | 1/2001 |
| WO | WO 02/17967 | 3/2002 |
| WO | WO 2004/112637 | 12/2004 |

(56) References Cited

FOREIGN PATENT DOCUMENTS

| WO | WO 2005/065373 | 7/2005 |
|----|----------------|--------|
| WO | WO 2008/062935 | 5/2008 |
| WO | WO 2009/151455 | 12/2009 |
| WO | WO 2010/132590 | 11/2010 |
| WO | WO 2011/078863 | 6/2011 |
| WO | WO 2011/078864 | 6/2011 |
| WO | WO 2011/079027 | 6/2011 |
| WO | WO 2011/079028 | 6/2011 |
| WO | WO 2012/082102 | 6/2012 |
| WO | WO 2012/082183 | 6/2012 |
| WO | WO 2012/082185 | 6/2012 |

OTHER PUBLICATIONS

International Search Report and Written Opinion in International Application No. PCT/US09/069408 mailed Jul. 23, 2010.
International Search Report and Wiitten Opinion in International Application No. PCT/US09/069402 mailed Jul. 23, 2010.
International Search Report and Written Opinion in International Application No. PCT/US10/060861 mailed Jun. 8, 2011.
International Search Report and Written Opinion in International Application No. PCT/US10/049102 mailed Jun. 7, 2011.
Written Opinion for PCT/US2009/069402 mailed on Dec. 16, 2011.
Written Opinion for PCT/US2009/069408 mailed on Dec. 16, 2011.
ISR and Written Opinion for PCT/US2010/060105 mailed on Aug. 30, 2011.
ISR and Written Opinion for PCT/US2010/060867 mailed on Oct. 14, 2011.
ISR and Written Opinion for PCT/US2010/060874 mailed on Jan. 11, 2012.
ISR and Written Opinion for PCT/US2010/060877 mailed on Oct. 7, 2011.
Written Opinion for PCT/US2010/060881 mailed on Dec. 28, 2011.
ISR and Written Opinion for PCT/US2011/023356 mailed on Oct. 21, 2011.
ISR and Written Opinion for PCT/US2011/045010 mailed on Nov. 25, 2011.
ISR and Written Opinion for PCT/US2011/046132 mailed on Dec. 1, 2011.
Written Opinion for PCT/US2011/046132, mailed Nov. 26, 2012.

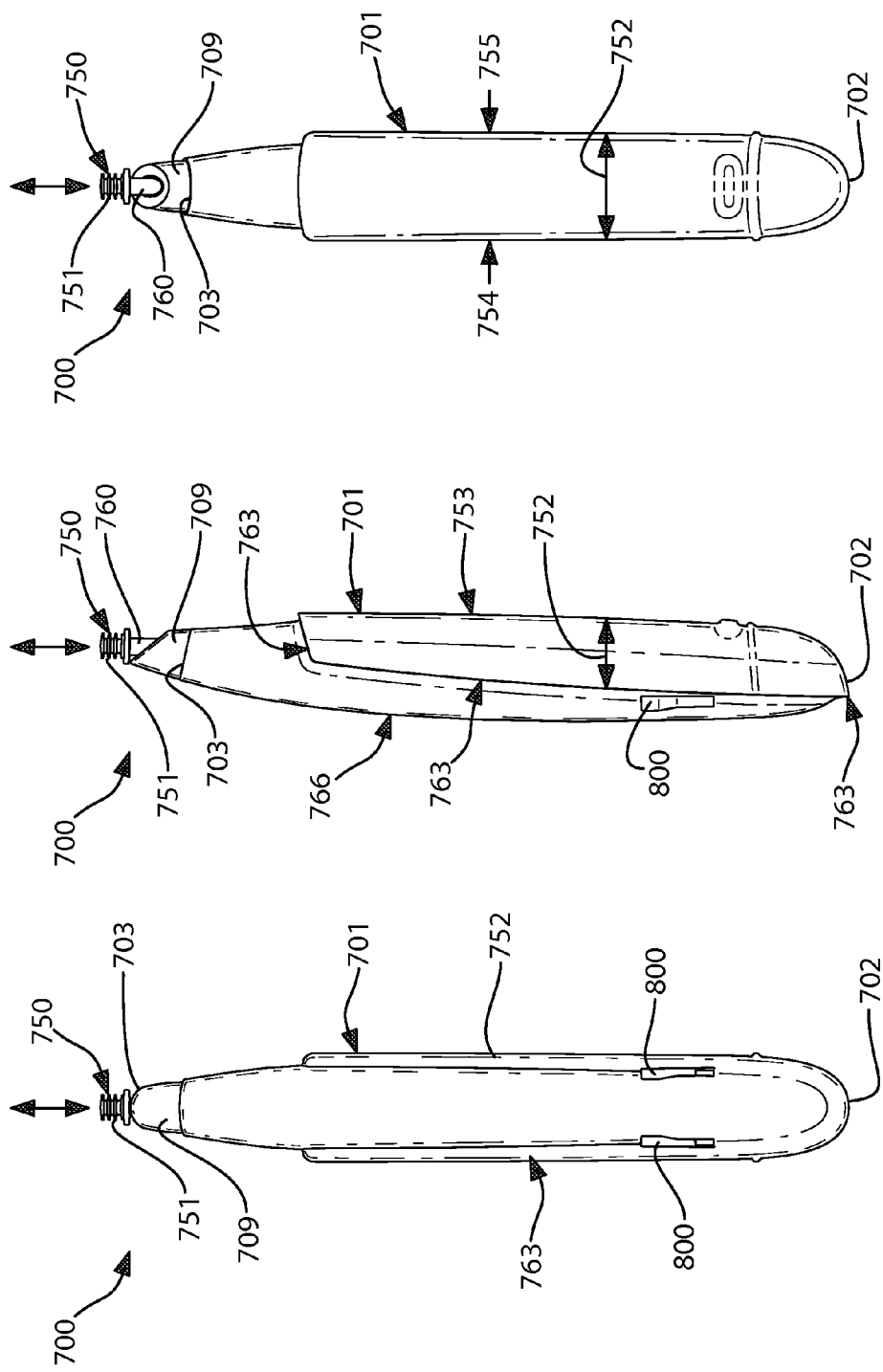

ic cabinets but also requires that the user remember to use the whitening system. Furthermore, these tray-based systems are not conveniently portable for transport and/or travel.

ORAL CARE SYSTEM, KIT AND METHOD

CROSS-REFERENCE TO RELATED APPLICATIONS

This application is a national stage entry under 35 U.S.C. §371 of International Patent Application No. PCT/US2010/060867, filed 16 Dec. 2010, which is a continuation in part of International Application No. PCT/US2009/069408 filed on Dec. 23, 2009 and International Application No. PCT/US2009/069402 filed on Dec. 23, 2009. PCT/US/2010/060867 also claims priority to U.S. Provisional Application No. 61/410,514 filed on Nov. 5, 2010; U.S. Provisional Application No. 61/423,397 filed on Dec. 15, 2010; U.S. Provisional Application No. 61/423,414 filed on Dec. 15, 2010; U.S. Provisional Application No. 61/423,435 filed on Dec. 15, 2010; and U.S. Provisional Application No. 61/423,449 filed on Dec. 15, 2010, all of which are incorporated herein by reference.

FIELD OF THE INVENTION

The present invention relates generally to oral care systems, kits and methods, and specifically to a system, kit and method including a toothbrush having an open cavity that retains a removable dispenser containing an oral care fluid.

BACKGROUND OF THE INVENTION

Oral care products or agents are applied in different ways. For example, without limitation, a common technique used for tooth whitening products is to cast an impression of a person's teeth and provide a tray of the shape of this impression. A person then only needs to add a whitening composition to the tray and to apply the tray to his/her teeth. This is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to ones teeth. After a few treatments the teeth gradually whiten.

A problem with existing brushing techniques is that saliva in the mouth contains the enzyme catalase. This enzyme will catalize the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative effect on the whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen.

A more portable, compact and convenient way to store oral care products, and to dispense and apply those oral care products to oral surfaces is desired.

BRIEF SUMMARY OF THE INVENTION

Embodiments of the present invention provide an efficient, compact, and portable oral care system that combines an oral care implement such as a toothbrush with an oral care product or agent dispenser in a highly portable and convenient housing. Advantageously, such embodiments are especially suited for easy transport and/or travel.

Preferred embodiments of the present invention are directed to a toothbrush having an open cavity in its handle that retains a removable dispenser containing a fluid, such as an oral care fluid, reservoir. In some exemplary embodiments, the oral care fluid includes oral care agents, either active or non-active, that may include without limitation whitening, enamel protection, anti-sensitivity, fluoride, tartar protection, or other agents. The dispenser can be detachably docked and stored at least partially within the handle of the toothbrush so that a gripping portion of the dispenser protrudes from the toothbrush for access to a user permitting easy removal and use of the dispenser. In some embodiments, the dispenser is configured as and forms a removable portion of the handle itself. The dispenser can be completely removable from the toothbrush in certain embodiments so that the user can apply the fluid to his/her teeth with ease, and then reinsert the dispenser in the toothbrush for convenient storage. In certain embodiments, the dispenser may be a pen-like component. The toothbrush can removably and non-fixedly secure the dispenser within the handle so that the dispenser can be repetitively removed and reinserted therein. In some embodiments, the dispenser may be adapted to be user-refillable for repeated use.

According to one embodiment of the present invention, an oral care system includes a toothbrush and a dispenser detachably coupled to the toothbrush. In some embodiments, the dispenser may form a constituent portion of a handle of the toothbrush. The dispenser may include a housing having an internal reservoir configured for containing a fluid, a dispensing orifice in the housing in fluid communication with the reservoir, and a fluid delivery system. The fluid delivery system may be a ratcheting type dispensing system in one embodiment including a ratchet rod extending into the reservoir, an actuator operably coupled to the ratchet rod for imparting movement thereto, and a two-piece plunger assembly operably coupled to the ratchet rod and axially movable within the housing by activation of the actuator. The plunger assembly forms a selectively-positionable transverse end wall of the reservoir, which in some embodiments is movable or advanceable only in a single axial direction. The plunger assembly includes an outer cup seal slidably engaged with the housing and an inner plunger disposed at least partially in the cup seal. The plunger also includes a pawl movably engaged with ratchet rod, wherein activation of the actuator moves the plunger assembly in a first direction and dispenses the fluid from the reservoir via the orifice.

According to one embodiment of the present invention, an oral care system includes a toothbrush and a dispenser detachably coupled to the toothbrush. The dispenser includes a housing having a distal dispensing end, a proximal actuating end, and an internal reservoir configured for containing a fluid defined therebetween. A dispensing orifice may be disposed in the distal dispensing end of the housing in fluid communication with the reservoir for delivering the fluid. The dispenser further includes a fluid delivery system including a ratchet rod extending into the reservoir, a resiliently deformable actuator disposed on the actuating end of the housing and operably coupled to the ratchet rod for imparting movement thereto, and a plunger assembly operably coupled to the ratchet rod and axially movable within the housing in a first direction by activation of the actuator. The plunger assembly forms a selectively-positionable end wall of the reservoir. In some embodiments, the actuator may be formed of a self-biasing elastomeric material having an elastic memory and being biased towards the operating end of the housing. Depressing the actuator deforms and partially collapses the actuator inwards and moves the ratchet rod and plunger assembly together in the first direction and dispenses the fluid from the reservoir via the orifice. Releasing the actuator causes the actuator to reassume an un-depressed and undeformed position under the self-biasing force of the actuator material elastic memory. This retracts the ratchet rod in a second direction opposite the first. The plunger assembly remains stationary in an advanced axial position.

A method for dispensing an oral care product from an oral care system is also provided. In one embodiment, the method includes: providing an oral care system including a toothbrush and a dispenser detachably mounted to the toothbrush, the dispenser including a distal dispensing end, a proximal operating end, and reservoir containing an oral care product. The dispenser may further include a ratcheting fluid dispensing mechanism including: a ratchet rod axially movable within the housing; a resiliently deformable push button formed of an elastomeric material and operably coupled to the ratchet rod for imparting motion thereto, the push button having an elastic memory and being self-biased towards an undeformed inactive position; and a plunger assembly axially slidable within the housing and including a pawl operably coupled to the ratchet rod, the plunger assembly forming a movable end wall of the reservoir. The method further includes the steps of: detaching the dispenser from toothbrush; depressing the push button, wherein the push button becomes activated and deformed; moving the ratchet rod and plunger assembly together in a first distal axial direction wherein the plunger assembly is moved from a first position to a second position and oral care product is dispensed; releasing the push button, wherein the push button is returned to the undeformed inactive position under the self-biasing force of the push button; and retracting the ratchet rod in a second proximal direction, wherein the plunger assembly remains stationary in the second position.

In one aspect of the preferred embodiments, an oral care system according to the present invention includes: a toothbrush including: a handle having a proximal end, a distal end and a longitudinal axis; a head connected to the distal end of the handle, the head including one or more tooth engaging elements extending from the head; an elongated tubular cavity formed into the handle, the cavity extending along the longitudinal axis of the handle and having an open end at the proximal end of the handle; and a dispenser including: an elongated tubular housing having a dispensing end and a gripping end; a reservoir located within the housing, the reservoir containing an fluid; and an applicator protruding from the dispensing end of the housing, the applicator selected from a group consisting of bristles, a sponge material and a fibrillated material; the dispenser sized and shaped to be slid into and out of the cavity of the toothbrush between a storage state and an application state, the storage state including the dispenser non-fixedly secured within the cavity of the handle so that at least a majority of the length of the dispenser is located within the cavity and the gripping end of the dispenser protrudes from the open end of the cavity, and the application state including the dispenser entirely removed from the cavity and separated from the toothbrush so that a user can apply the fluid to teeth via the applicator.

In another aspect of the preferred embodiments, an oral care kit according to the present invention includes: a toothbrush including: a handle having a proximal end, a distal end and a longitudinal axis; a head connected to the distal end of the handle, the head including one or more tooth engaging elements extending from the head; an elongated tubular cavity formed into the handle, the cavity extending along the longitudinal axis of the handle and having an open end at the proximal end of the handle; and a dispenser including: an elongated tubular housing having a dispensing end and a gripping end; a reservoir located within the housing, the reservoir containing an fluid; a fluid delivery channel extending from the reservoir to an applicator protruding from the dispensing end of the housing; and a cap operably coupled to the dispensing end and enclosing the applicator, the dispensing end of the housing including a feature that mates with a feature of the cap to non-fixedly secure the cap to the dispenser; the dispenser sized and shaped to be slid into and out of the cavity of the toothbrush between a storage state and an application state, the storage state including the dispenser non-fixedly secured within the cavity of the handle so that at least a majority of the length of the dispenser is located within the cavity and the gripping end of the dispenser protrudes from the open end of the cavity, and the application state including the dispenser entirely removed from the cavity and separated from the toothbrush so that a user can apply the fluid to teeth via the applicator.

In yet another aspect of the preferred embodiments, an oral care system according to the present invention includes: a toothbrush including: a handle having a proximal end, a distal end and a longitudinal axis; a head connected to the distal end of the handle, the head including one or more tooth engaging elements extending from the head; an elongated tubular cavity formed into the handle, the cavity extending along the longitudinal axis of the handle and having an open end at the proximal end of the handle; and a dispenser including: an elongated tubular housing having a dispensing end and a gripping end; a reservoir located within the housing, the reservoir containing a fluid; and a fluid delivery channel extending from the reservoir to an applicator protruding from the dispensing end of the housing, the applicator selected from a group consisting of bristles, a sponge material and a fibrillated material; the dispenser sized and shaped to be slid into and out of the cavity of the toothbrush between a storage state and an application state, the storage state including the dispenser non-fixedly secured within the cavity of the handle so that at least a majority of the length of the dispenser is located within the cavity and the gripping end of the dispenser protrudes from the open end of the cavity, and the application state including the dispenser entirely removed from the cavity and separated from the toothbrush so that a user can apply the fluid to teeth via the applicator.

In still another aspect of the preferred embodiments, an oral care system according to the present invention includes: a toothbrush including: a handle having a proximal end, a distal end and a longitudinal axis; a head connected to the distal end of the handle, the head including one or more tooth engaging elements extending from the head; a cavity formed into the handle, the cavity extending along the longitudinal axis of the handle and having an open end at the proximal end of the handle; and a dispenser including: a housing having a dispensing end and a gripping end; a reservoir located within the housing, the reservoir containing a fluid; and a fluid delivery channel extending from the reservoir to an applicator protruding from the dispensing end of the housing; the dispenser sized and shaped to be slid into and out of the cavity of the toothbrush between a storage state and an application state, the storage state including the dispenser non-fixedly secured within the cavity of the handle so that at least a majority of the length of the dispenser is located within the cavity and the gripping end of the dispenser protrudes from the open end of the cavity, and the application state including the dispenser entirely removed from the cavity and separated from the toothbrush so that a user can apply the fluid to teeth via the applicator.

In a further aspect of the preferred embodiments, an oral care system according to the present invention includes: a toothbrush including: a handle having a proximal end, a distal end and a longitudinal axis; a head connected to the distal end of the handle, the head including one or more tooth engaging elements extending from the head; a cavity formed into the handle, the cavity extending along the longitudinal axis of the handle and having an opening; and a dispenser including: a housing having a dispensing end and a gripping end; a reservoir located within the housing, the reservoir containing a fluid; and a fluid delivery channel extending from the reservoir to an applicator protruding from the dispensing end of the housing; the dispenser sized and shaped to be slid into and out of the cavity of the toothbrush via the opening between a storage state and an application state, the storage state including the dispenser non-fixedly secured within the cavity of the handle so that at least a majority of the dispenser is located within the cavity, and the application state including the dispenser entirely removed from the cavity and separated from the toothbrush so that a user can apply the fluid to teeth via the applicator.

In a still further aspect of the preferred embodiments, the invention can be an oral care system comprising: a toothbrush including: a handle having a proximal end, a distal end and a longitudinal axis; a head connected to the distal end of the handle; a cavity formed into the handle and having an opening; and a dispenser including: a housing having a dispensing end and a gripping end; a fluid located within the housing for being dispensed via an orifice in the dispensing end; and the dispenser sized and shaped to be slid into and out of the cavity of the toothbrush via the opening between a storage state and an application state, the storage state including the dispenser non-fixedly secured within the cavity of the handle, and the application state including the dispenser entirely removed from the cavity and separated from the toothbrush so that a user can apply the fluid.

In another aspect, the invention can be an oral care system comprising: a toothbrush; and a dispenser detachably coupled to the toothbrush, the dispenser comprising: an internal reservoir containing a fluid; and a conduit in fluid communication with the reservoir and terminating in an orifice for dispensing the fluid from the reservoir; and a plug having an axis, a proximal plug portion disposed within the conduit, and a distal plug portion disposed within a socket of the toothbrush, wherein a first axial force is required to remove the proximal plug portion from the conduit of the dispenser and a second axial force is required to remove the distal plug portion from the socket of the toothbrush, the second axial force being greater than the first axial force.

In a further aspect, the invention can be an oral care system comprising: a toothbrush; and a dispenser detachably coupled to the toothbrush, the dispenser comprising: an internal reservoir containing a fluid; and a conduit in fluid communication with the reservoir and terminating in an orifice for dispensing the fluid; and a plug having a proximal plug portion disposed within the conduit and a distal plug portion disposed within a socket of the toothbrush.

In a still further aspect, the invention can be a method of manufacturing an oral care system comprising: a) providing a toothbrush having a socket; b) providing a dispenser having an internal reservoir containing a fluid and a conduit in fluid communication with the reservoir, the conduit terminating in an orifice for dispensing the fluid from the reservoir, and a plug having a proximal plug portion disposed within and sealing the conduit and a distal plug portion extending from the dispenser; and c) detachably coupling the dispenser to the toothbrush by sliding the distal plug portion into the socket of the toothbrush.

In an even further aspect, the invention can be a method of applying a fluid to an oral surface comprising: a) providing an oral care system comprising a toothbrush having a socket, a dispenser detachably coupled to the toothbrush, the dispenser comprising an internal reservoir containing a fluid and a conduit in fluid communication with the reservoir, the conduit terminating in an orifice for dispensing the fluid from the reservoir, and a plug having a proximal plug portion disposed within the conduit and a distal plug portion disposed within a socket of the toothbrush; b) detaching the dispenser from the toothbrush, the proximal plug portion sliding out of the conduit and the distal plug portion remaining in the socket of the toothbrush; and c) dispensing the fluid from the dispenser via the orifice onto the oral surface.

In preferred exemplary embodiments, any suitable fluid may be used, for example a suitable oral care fluid may be used with embodiments and methods described herein according to the present invention. Accordingly, the oral care treatment system may be any type of system including without limitation tooth whitening, enamel protection, anti-sensitivity, fluoride, tartar protection/control, and others. The invention is expressly not limited to any particular type of fluid, oral care system or oral care agent, unless specifically claimed.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention

BRIEF DESCRIPTION OF THE DRAWINGS

The features of the preferred embodiments will be described with reference to the following drawings in which like elements are labeled similarly.

FIGS. 23-25 are a top view, side elevation view, and bottom view respectively of the dispenser of the oral care system of FIG. 16.

DETAILED DESCRIPTION OF THE INVENTION

Figure 1:
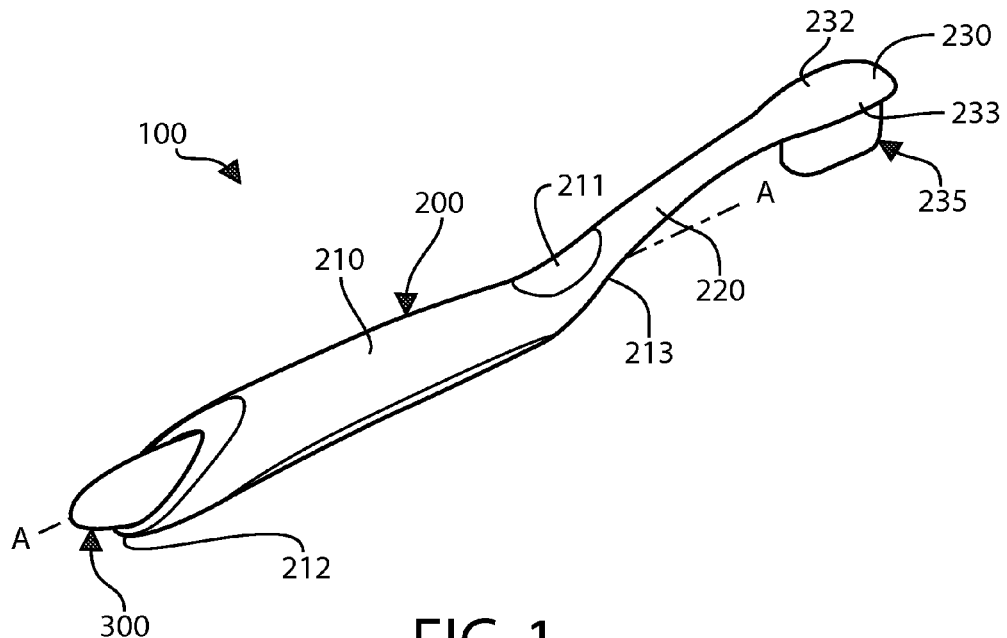
FIG. 1 is a rear perspective view of an oral care system including a toothbrush and fluid dispenser according to one embodiment of the present invention.

The following description of the preferred embodiment(s) is merely exemplary in nature and is in no way intended to limit the invention, its application, or uses. The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

In the description of embodiments of the invention disclosed herein, any reference to direction or orientation is merely intended for convenience of description and is not intended in any way to limit the scope of the present invention. Moreover, the features and benefits of the invention are illustrated by reference to preferred embodiments. Accordingly, the invention expressly should not be limited to such preferred embodiments illustrating some possible but non-limiting combination of features that may be provided alone or in other combinations of features; the scope of the invention being defined by the claims appended hereto.

Preferred embodiments of the present invention will now be described with respect to one possible oral care or treatment system. Embodiments of the oral care system may include without limitation the following agents: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of fluid and the invention is expressly not limited to any particular oral care system or agent alone.

Figure 2:
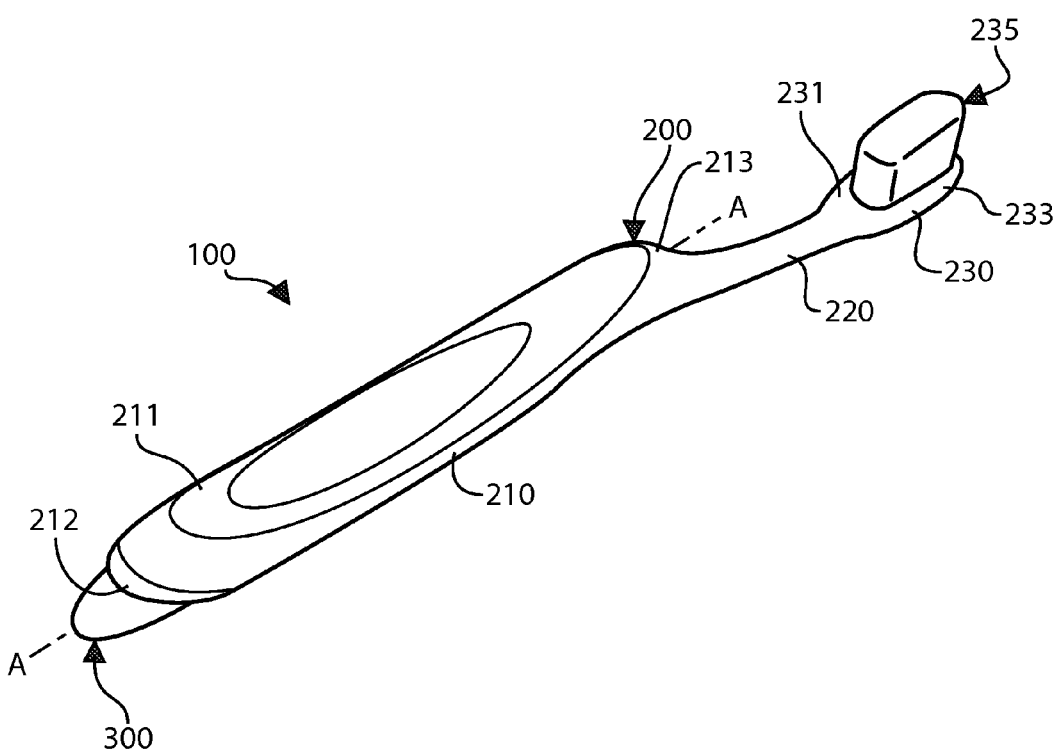
FIG. 2 is a front perspective view of the oral care system of FIG. 1.
Figure 3:
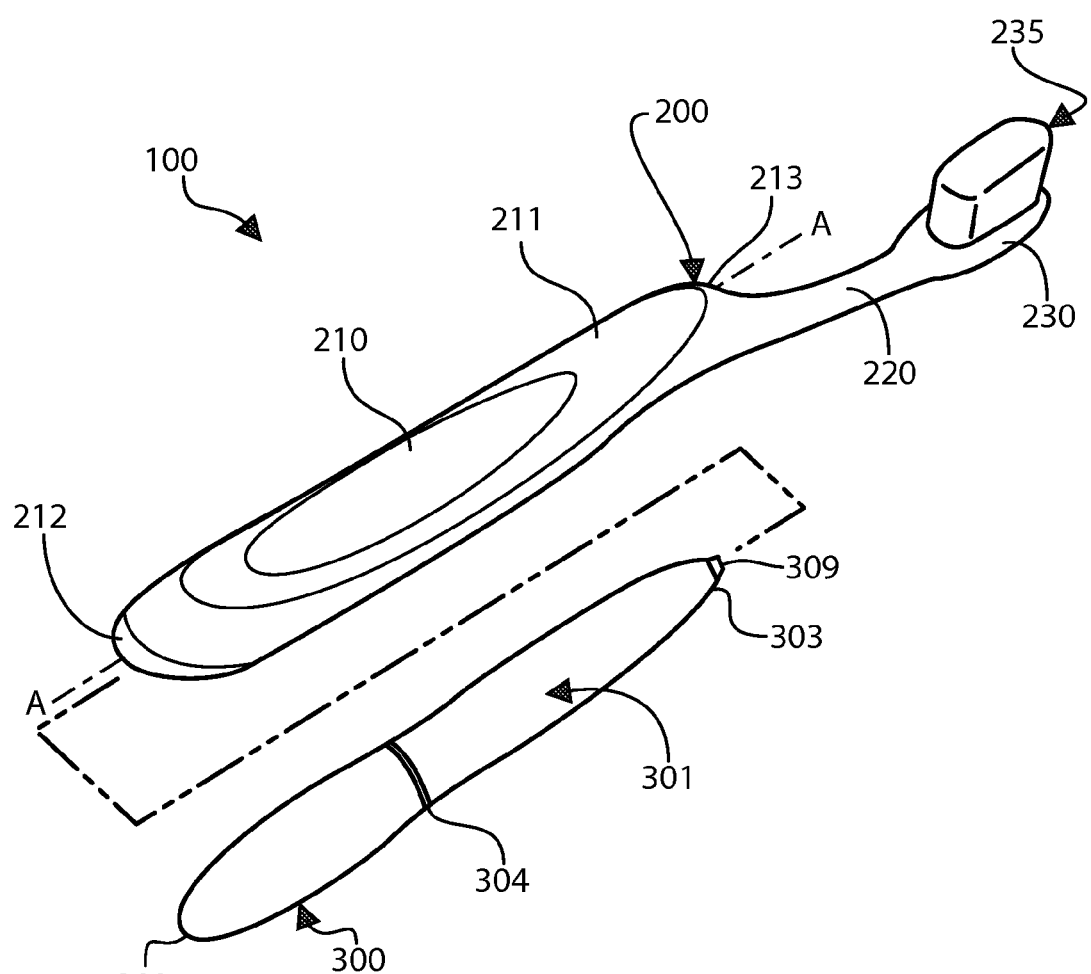
FIG. 3 is a front perspective view of the oral care system of FIG. 1 with the dispenser removed from the toothbrush.

Referring to FIGS. 1-3, an oral care system 100 is illustrated according to one embodiment of the present invention. The oral care system 100 is a compact readily portable self-contained user-friendly system that comprises all of the necessary components and chemistries necessary for a user to perform a desired oral care treatment routine. As will be described in greater detail below, the oral care system 100 in one exemplary embodiment generally takes the form of a modified toothbrush having a removable dispenser disposed at least partially within its handle. Because the dispenser is located within the handle of the toothbrush itself, the oral care system 100 is portable for travel, easy to use, and reduces the amount of required storage space. Furthermore, since the toothbrush and dispenser are housed together, the user is less likely to misplace the dispenser and be more inclined to maintain the oral treatment routine with the dispenser since brushing will remind the user to simply detach and apply the contents of the dispenser.

The oral care system 100 generally comprises a toothbrush body 200 (hereinafter referred to simply as a toothbrush) and a dispenser 300. While the invention is described herein with respect to the use of a toothbrush as one of the two primary components of the oral care system 100, it is to be understood that other alternate oral care implements can be used within the scope of the invention, including tongue cleaners, tooth polishers and specially designed ansate implements having tooth engaging elements. In certain instances, the toothbrush 200 may include tooth engaging elements that are specifically designed to increase the effect of the active agent in the dispenser on the teeth. For example, the tooth engaging elements may include elastomeric wiping elements that assist in removing stains from teeth and/or assist with forcing the fluid into the tubules of the teeth. Moreover, while the toothbrush 200 is preferably a manual toothbrush, the toothbrush may be a powered toothbrush in other embodiments of the invention. It is to be understood that the inventive system can be utilized for a variety of intended oral care needs by filling the dispenser 300 with any oral care material, such as an oral care agent that achieves a desired oral effect. In one embodiment, the oral care agent, is preferably free of (i.e., is not) toothpaste as the dispenser is intended to augment not supplant the brushing regimen. The oral care agent and/or its medium can be selected to complement a toothpaste formula, such as by coordinating flavors, colors, aesthetics, or active ingredients.

The toothbrush 200 generally comprises a handle portion 210, a neck portion 220 and a head portion 230. The handle 210 provides the user with a mechanism by which he/she can readily grip and manipulate the toothbrush 200. The handle 210 may be formed of many different shapes, sizes, materials and a variety of manufacturing methods that are well-known to those skilled in the art, so long as it can house the dispenser 300 therein as described in detail below. If desired, the handle 210 may include a suitable textured grip 211 made of soft elastomeric material. The handle 210 can be a single or multi-part construction. The handle 210 extends from a proximal end 212 to a distal end 213 along a longitudinal axis A-A. As will be described in greater detail below with respect to FIG. 6, a cavity 240 is formed within the handle 210. An opening 215 is provided at the proximal end 212 of the handle 210 that provides a passageway into the cavity 240 through which the dispenser 300 can be inserted and retracted. While the opening 215 is located at the proximal end 212 of the handle in the exemplified embodiment, the opening may be located at other positions on the handle 210 in other embodiments of the invention. For example, the opening 215 may be located on a longitudinal surface of the handle 210 (e.g., the front surface, the rear surface and/or the side surfaces) and be elongated to provide sufficient access to the cavity 240, as further described herein with respect to an alternative embodiment shown in FIG. 16.

The handle 210 transitions into the neck 220 at the distal end 213. While the neck 220 generally has a smaller transverse cross-sectional area than the handle 220, the invention is not so limited. Broadly speaking, the neck 220 is merely the transition region between the handle 210 and the head 230 and can conceptually be considered as a portion of the handle 210. In this manner, the head 230 is connected to the distal end 213 of the handle 210 (via the neck 220).

The head 230 and handle 220 of the toothbrush 200 are preferably formed as a single unitary structure using a molding, milling, machining or other suitable process. However, in other embodiments, the handle 210 and head 230 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 230 and handle 210 are of a unitary or multi-piece construction (including connection techniques) is not limiting of the present invention, unless specifically stated. In some embodiment of the invention, the head 230 may be detachable (and replaceable) from the handle 210 using techniques known in the art.

The head 230 generally comprises a front surface 231, a rear surface 232 and a peripheral side surface 233 that extends between the front and rear surfaces 231, 232. The front surface 231 and the rear surface 232 of the head 230 can take on a wide variety of shapes and contours, none of which are limiting of the present invention. For example, the front and rear surfaces 231, 232 can be planar, contoured or combinations thereof. Moreover, if desired, the rear surface 232 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 230 is normally widened relative to the neck 220 of the handle 210, it could in some constructions simply be a continuous extension or narrowing of the handle 210.

The front surface 231 of the head 230 comprises a collection of oral cleaning elements such as tooth engaging elements 235 extending therefrom for cleaning and/or polishing contact with an oral surface and/or interdental spaces. While the collection of tooth engaging elements 235 is preferably suited for brushing teeth, the collection of cleaning elements 235 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements preferably has a hardness property in the range of A8 to A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 235 of the present invention can be connected to the head 120 in any manner known in the art. For example, staples/anchors, in-mold tufting (IFT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 200 and the dispenser 300 are non-unitary separate structures that are specially designed to be non-fixedly secured together when in an assembled state (referred to herein as a storage state) and completely isolated and separated from one another when in a disassembled state (referred to herein as an application state). The toothbrush 200 and the dispenser 300 are illustrated in the storage state in FIGS. 1 and 2 and in the application state in FIG. 3. The dispenser 300 can be slidably manipulated and moved between the storage state (FIGS. 1 and 2) in which the dispenser is docked in toothbrush handle portion 210 and the application state (FIG. 3) in which the dispenser is removed from handle portion 210 by the user as desired. The dispenser docking system for nesting and disengagement of dispenser 300, and the relevant structural elements of the toothbrush 200 and dispenser 300 comprising the docking system, will now be described in greater detail.

Figure 4:
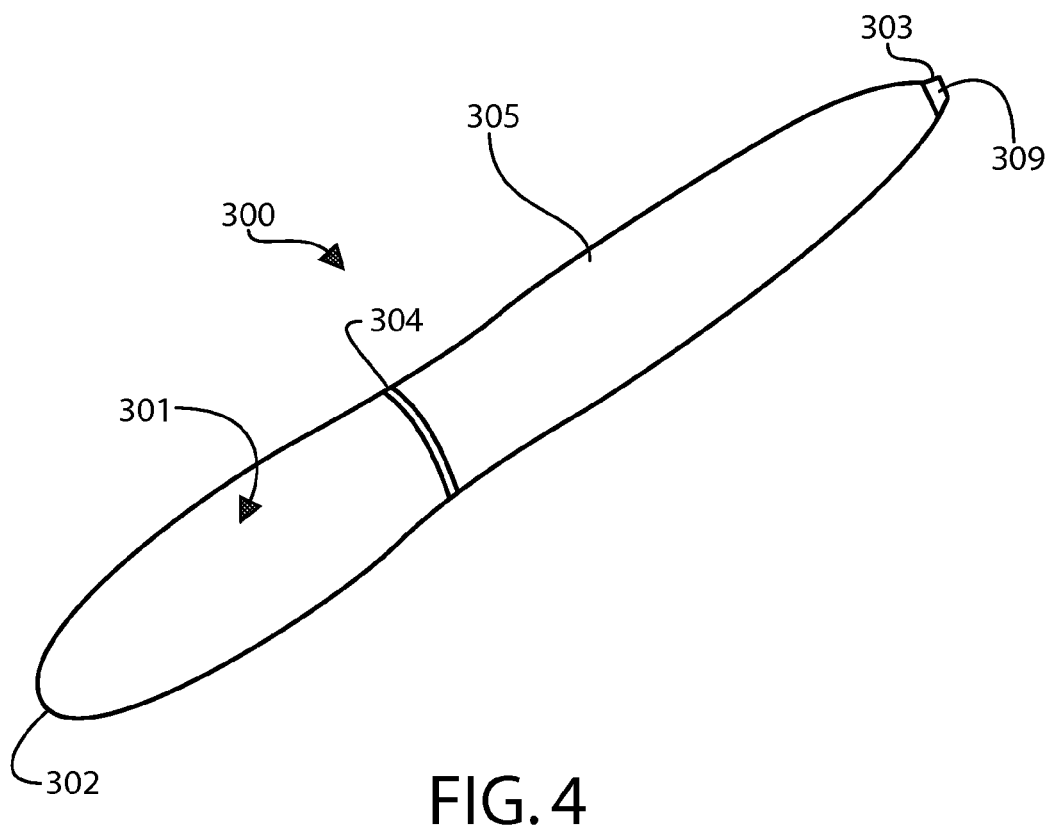
FIG. 4 is a perspective view of the dispenser of the oral care system of FIG. 1.
Figure 5:
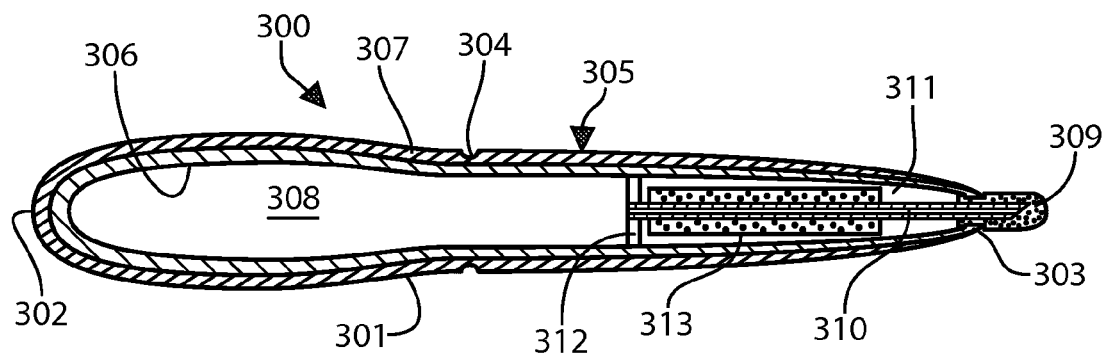
FIG. 5 is a longitudinal cross-sectional view of the dispenser of FIG. 4.

Referring now to FIGS. 4 and 5, the dispenser 300 is schematically illustrated. The dispenser 300 is an elongated tubular pen-like structure. The dispenser 300 has a housing 301 that extends between a gripping end 302 (which can be conceptually considered as the proximal end) and a dispensing end 303 (which can be conceptually considered as the distal end). An annular groove 304 is formed into the outside surface 305 of the housing 301. While the groove 304 is located near a middle point along the length of the housing 301, the groove 304 can be located on the housing 301 at any position desired. Moreover, while the groove 304 is illustrated as a concisely defined channel, in other embodiment the groove can be formed by a gradually sloping curvature, a segmented ring of depressions, and/or a simple dimple or contour of the housing 301.

The housing 301 generally comprises an inner layer 306 and an outer layer 307. The inner layer 306 is preferably constructed of a material that is sufficiently rigid to provide the necessary structural integrity for the dispenser 300. For example, the inner layer can be made out of a moldable hard plastic. Moldable hard thermoplastics are preferred. Suitable plastics include polymers and copolymers of ethylene, propylene, butadiene, vinyl compounds and polyesters such as polyethylene terephthalate. The chosen plastic(s), however, must be compatible with the oral care agent that is to be stored within the dispenser 300 and should not be corroded or degraded by the oral care agents.

The outer layer 307 is preferably made of a soft resilient material, such as an elastomeric material. Suitable elastomeric materials include thermoplastic elastomers (TPE) or other similar materials used in oral care products. The elastomeric material of the outer layer 307 may have a hardness durometer measurement ranging between A13 to A50 Shore hardness, although materials outside this range may be used. A preferred range of the hardness durometer rating is between A25 to A40 Shore hardness. While an over-molding construction is preferred for the outer layer 307, a suitable deformable thermoplastic material, such as TPE, may be formed in a thin layer and attached to inner layer 306 with an appropriate adhesive, sonic welding, or by other means. It should be noted, however, that in some embodiments of the invention, the housing 301 may be constructed of a single layer of material.

Figure 7A:
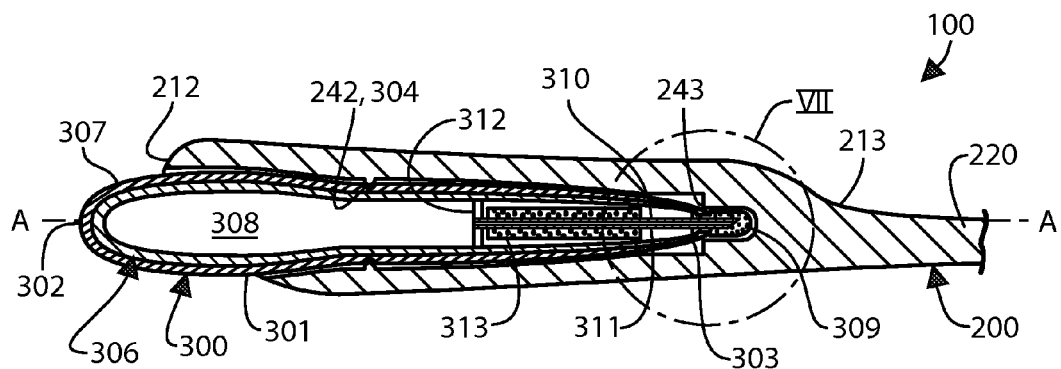
FIG. 7A is a longitudinal cross-sectional view of the oral care system of FIG. 1 in the storage state.

Referring to FIGS. 5 and 7A, the housing 301 forms an internal chamber which defines a reservoir 308 for holding the desired fluid, oral care material or product, which can be any active or inactive oral care agent. The oral care agent and/or its carrier may be in any form such as a solid or a flowable material including without limitation viscous pastes/gels or less viscous liquid compositions. Preferably, the oral care agent is a flowable material having a low viscosity in preferred embodiments. Any suitable oral care agent can be used in the present invention. For example, the oral care agent includes whitening agents, including without limitation, peroxide containing tooth whitening compositions. Suitable peroxide containing tooth whitening compositions are disclosed in U.S. patent Ser. No. 11/403,372, filed Apr. 13, 2006, to the present assignee, the entirety of which is hereby incorporated by reference. While a tooth whitening agent or a sensitivity agent is one of the preferred agents in the present invention, any other suitable oral care agents or fluids can be used with embodiments of the present invention and, thus, stored within the reservoir 308. Contemplated oral care fluids or agents can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The oral care fluid in one embodiment is preferably free of (i.e., is not) toothpaste. Instead, the oral care fluid is intended to provide supplemental oral care benefits in addition to merely brushing one's teeth. Other suitable oral care fluids could include lip balm or other materials that are typically available in a semi-solid state.

In some embodiments, the materials useful in the fluid contained in the reservoir may include oral care compositions comprising a basic amino acid in free or salt form. In one embodiment, the basic amino acid may be arginine. Various formulations would be useful to supply the arginine to the user. One such oral care composition, e.g., a dentifrice, may be used comprising:

i. an effective amount of a basic amino acid, in free or salt form, e.g., arginine, e.g., present in an amount of at least about 1%, for example about 1 to about 30%; by weight of total formulation, weight calculated as free base;
 ii. an effective amount of fluoride, e.g., a soluble fluoride salt, e.g., sodium fluoride, stannous fluoride or sodium monofluorophosphate, providing from about 250 to about 25,000 ppm fluoride ions, e.g., about 1,000 to about 1,500 ppm; and
 iii. an abrasive, e.g., silica, calcium carbonate or dicalcium phosphate.

The dental treatment materials of the present invention preferably have a viscosity suitable for use in tooth treatment applications and methods. As used herein, the "viscosity" shall refer to "dynamic viscosity" and is defined as the ratio of the shearing stress to the rate of deformation as measured by AR 1000-N Rheometer from TA Instruments, New Castle, Del.

When measured at a shear rate of 1 seconds$^{-1}$, the viscosity preferably will have a range with the lower end of the range generally about 0.0025 poise, preferably about 0.1 poise, and more preferably about 75 poise, with the upper end of the range being selected independently of the lower end of the range and generally about 10,000 poise, preferably about 5,000 poise, and more preferably about 1,000 poise. Non-limiting examples of suitable viscosity ranges when measured at a shear rate of 1 seconds$^{-1}$ includes, about 0.0025 poise to about 10,000 poise, about 0.1 poise to about 5,000 poise, about 75 poise to about 1000 poise, and about 0.1 poise to about 10,000 poise.

When measured at a shear rate of 100 seconds$^{-1}$, the viscosity will have a range with the lower end of the range generally about 0.0025 poise, preferably about 0.05 poise, and more preferably about 7.5 poise, with the upper end of the range being selected independently of the lower end of the range and generally about 1,000 poise, preferably about 100 poise, and more preferably about 75 poise. Non-limiting examples of suitable viscosity ranges when measured at a shear rate of 100 seconds.sup.31 1 includes, about 0.0025 poise to about 1,000 poise, about 0.05 poise to about 100 poise, about 7.5 poise to about 75 poise, and about 0.05 poise to about 1,000 poise.

When measured at a shear rate of 10,000 seconds$^{-1}$, the viscosity will have a range with the lower end of the range generally about 0.0025 poise, preferably about 0.05 poise, and more preferably about 5 poise, with the upper end of the range being selected independently of the lower end of the range and generally about 500 poise, preferably about 50 poise. Non-limiting examples of suitable viscosity ranges when measured at a shear rate of 10,000 seconds$^{-1}$ includes, about 0.0025 poise to about 500 poise, about 0.05 poise to about 50 poise, about 5 poise to about 50 poise, and about 0.05 poise to about 500 poise.

Each of the formulations contains a viscosity agent that adjusts the viscosity of the formulation to a level which permits effective flow from the reservoir 308, through the delivery channel 310, and to the dispensing end 303. This agent may be water, thickeners or thinners. The viscosity should be adjusted in relationship to the dimensions of the delivery channel 310 (including length, internal transverse cross-sectional area, shape, etc.), the composition of the delivery channel 310 used (i.e., hollow channel, porous channel, etc.), and the amount of force available to move the formulations through the delivery channel 310.

The reservoir 308 is fluidly coupled to an applicator 309 which protrudes from the dispensing end 303 of the housing 301 by the delivery channel 310. The delivery channel 310 delivers the oral care fluid from the reservoir 308 to the applicator 309. Of course, in some embodiments, a delivery channel may not be necessary or may merely be an extension of the reservoir or a space connecting the reservoir and the applicator (or an opening in the dispensing end). The user then presses and/or rubs the applicator 309 against his/her teeth to apply the oral care fluid to his/her teeth, preferably after brushing. The application process is much like using a standard pen and/or marker.

The applicator 309 may be constructed of bristles, a porous or sponge material, or a fibrillated material. Suitable bristles include any common bristle material such as nylon or PBT. The sponge-like materials can be of any common foam material such as urethane foams. The fibrillated surfaces can be comprised of various thermoplastics. In the use of bristles, the delivery channel 310 will deliver the composition to near the ends of the bristles. Usually there will be a single delivery channel. For sponge and fibrillated surfaces there usually will be plurality of smaller diameter channels so as to more uniformly distribute the composition onto the user's teeth. In one embodiment, the fibrillated material will have an essentially planar surface that has a plurality of protruding fibrils up to about 3 millimeter in length. Such a fibrillated surface provides a mini-brush surface. The invention, however, is not so limited and the applicator 309 can be any type of surface and/or configuration that can apply a viscous substance onto the hard surface of teeth, including merely an uncovered opening/orifice.

The delivery channel 310 can be a suitable sized tubular conduit having a hollow passageway or it can be constructed of a porous material. The mechanism of delivery of the fluid from the reservoir 308 to the applicator 309 (or an orifice in the dispensing end) can be strictly by capillary action, a mechanical or chemical pumping action, compression/squeezing of the dispenser 300, gravity and/or combinations thereof. In one embodiment, at least a portion of the housing 301 can be constructed to be transversely deformable so that the user can squeeze the dispenser 300, thereby increasing the pressure inside reservoir 308 and forcing the oral care fluid outwards from the reservoir 308 through the applicator 309. In such an embodiment, a one-way valve may be built into the dispenser to allow air back into the reservoir so that the dispenser housing 301 resumes its uncompressed/un-deformed state after use. In other embodiments, a piston-like mechanism can be used to the whitening agent from the reservoir 308 to the applicator 309. Of course, other mechanisms and actions can be used to achieve the dispensing goal. In certain embodiments, the delivery channel 310 may further include a one-way valve that only allows the oral care fluid to flow from the reservoir 308 toward the applicator 309, thereby preventing saliva or other contaminants from being drawn from the applicator 309 back into the reservoir 308 and/or delivery channel 310.

In the illustrated embodiment of the dispenser 300, an overflow chamber 311 is created near the dispensing end 303 by the addition of a transverse wall 312. The transverse wall 312 separates and substantially seals the reservoir 308 from the overflow chamber 311. The delivery channel 310 extends through the transverse wall 312 and through the overflow chamber 311, thereby fluidly coupling the reservoir 308 to the applicator 309. A porous material, which is in the form of a sleeve 313 can be positioned within the overflow chamber 311. The overflow chamber 311 can minimize excessive amounts of the oral care fluid from reaching the applicator 309 or leaking from the dispenser 300. The overflow chamber 311 will not be needed in all embodiments of the dispenser, depending on the delivery mechanism used.

The details of the dispenser 300 described above are not to be considered limiting of the present invention unless specifically recited in the claims. It is to be understood that the structural details of the dispenser body and its fluid delivery system can vary greatly.

However, in one embodiment, in order to make the oral care system 100 user friendly for travel, the reservoir 308 and/or the volume of active fluid in the reservoir may be selected so that the oral care system 100 can be taken on airplanes. Since about 2002, the volume of liquid that can be taken onto an airplane in the U.S. and other countries in a single container is limited, typically to about 3 fluid oz. The reservoir 308 and/or the volume of fluid in the reservoir 308 can be selected to meet the applicable regulatory standard, which may change from country to country and/or over time. In other embodiments, the reservoir 308 and/or volume of fluid may be selected to last a predetermined period of time assuming a suggested oral care regimen, such as at least two weeks, which may be at least 8 fluid oz. In other embodiments, the reservoir 308 and/or volume of fluid may be selected to last a period of time (assuming a suggested oral care regimen) that corresponds to a suggested life cycle of the toothbrush.

Furthermore, in some embodiments of the invention, the applicator 309 may be omitted from the dispenser 300. In such an embodiment, the desired oral care material will be delivered from the reservoir 308 of the dispenser 300 via a mere orifice in the dispensing end 303. Depending on the type of oral care material being used, this orifice may act like a nozzle or port for dispensing and/or ejecting a liquid or paste oral car material to the desired oral surface. Such an arrangement is especially useful when combined with a compressible/squeezable dispenser housing. In embodiments where a semi-solid oral care material is used, such as lip balm, the orifice may merely provide a passageway from the reservoir through which the semi-solid oral care material will protrude or can be slidably extended and refracted by any suitable conventional axial or rotary extension mechanism.

Figure 6:
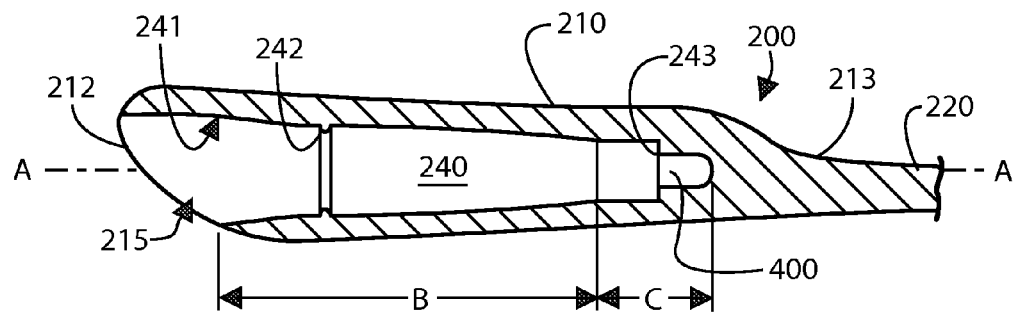
FIG. 6 is a longitudinal cross-sectional view of the handle of the toothbrush of the oral care system of FIG. 1.
Figure 7B:
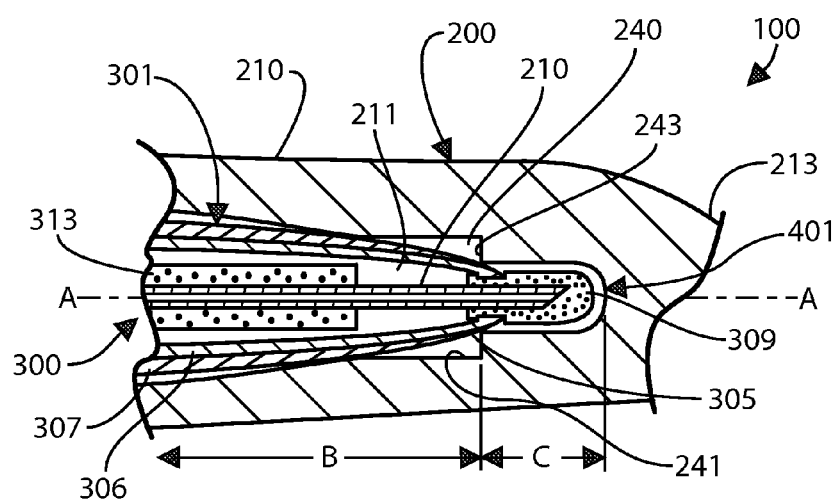
FIG. 7B is a close-up view of area VII of FIG. 7A.

Referring now to FIGS. 6, 7A, and 7B, the details of the toothbrush 200 which provide a nesting volume for the dispenser 300 in the docked or storage state will be described. The handle 210 of the toothbrush 200 comprises an internal cavity 240 that is sized and shaped to accommodate the dispenser 300. The cavity 240 is a generally tubular cavity that extends along the longitudinal axis A-A of the handle 210 and is defined by an inner surface/wall 241 that circumferentially surrounds the axis A-A. The opening 215, which is a substantially transversely oriented and located at the proximal end 212 of the handle 210 in one embodiment, provides a passageway from exterior of the toothbrush 200 to the internal cavity 240. The opening 215 is sized and shaped to allow the dispenser 300 to be slid into and out of the internal cavity 240. The size and shape of the cavity 240 generally corresponds to the size and shape of a portion of the dispenser 300 and, as described below with respect to FIG. 7A, non-fixedly and removably secures the dispenser 300 within the handle 210.

The cavity 240 comprises a longitudinal section B and a longitudinal section C. The longitudinal section B of the cavity 240 is sized and shaped to accommodate the housing 301 of the dispenser 300 while the longitudinal section C of the cavity 240 is sized and shaped to accommodate the applicator 309 and distal dispensing end 303 of the dispenser 300. More specifically, the longitudinal section B has both transverse and longitudinal cross-sectional profiles that generally correspond to the transverse and longitudinal cross-sectional profiles of the portion of the housing 301 of the dispenser 300 that nests within the cavity 240. Similarly, section C has transverse and longitudinal cross-sectional profiles that generally correspond to the transverse and longitudinal cross-sectional profiles of the applicator 309 and distal dispensing end 303 of the housing 301 of the dispenser 300 that nests within the cavity 240. Of course, the invention is not limited to such correspondence in all embodiments.

With continuing reference to FIGS. 6, 7A, and 7B, the cavity 240 has a generally tapered transverse section for a major portion of the longitudinal length of the cavity comprising the longitudinal sections A and B, wherein the transverse cross-section decreases as one moves forward/away from the opening 215 towards distal end 213 of handle portion 210. The tapered transverse cross-section of the cavity 240 assists with guiding and centering the dispenser 300 into proper placement and seating within the cavity 240 in the docked or storage state. The transverse cross-sectional area of section C is preferably substantially less than the transverse cross-sectional area of the longitudinal section B to coincide with the corresponding tapered shape of dispenser 300. As best shown in FIG. 6, in one embodiment the plane of the opening 215 is preferably angled transversely with respect to the longitudinal axis so as to further assist with the removal from and reinsertion of the dispenser 300 into the cavity 240.

With continuing reference to FIGS. 6, 7A, and 7B, the inner wall 241 of the cavity 240 comprises an annular ridge 242 that is designed to non-fixedly mate with the annular groove 304 of the dispenser 300 when in the storage or docked state. The annular ridge 242 and groove 304 provides a locking system for removably securing the dispenser 300 in the handle portion 210 of the toothbrush 200. In one possible embodiment, the annular ridge 242 is preferably convex shaped in cross-section and the groove 304 may have a complementary concave cross section to facilitate a smooth but locking engagement between the ridge and the groove (see FIGS. 6 and 7A). Of course, other mating shapes and/or features can be utilized on the dispenser 300 and the wall 241 instead of a groove/ridge arrangement for removably securing the dispenser 300 in the handle portion 210 of the toothbrush 200. The annular ridge 242 may also form a transition between the longitudinal section B and the longitudinal section C of the cavity 240 as shown.

With continuing reference to FIGS. 6, 7A, and 7B, the inner wall 241 of the cavity 240 also further includes an annular shoulder 243 that preferably is located near the distal end 213 of the handle portion 210 as shown. The annular shoulder 243 provides a protruding structure that creates the smaller distal transverse cross-sectional area of the longitudinal section C in the form of an applicator end receptacle 400 near the distal end 213 of the handle portion 210. While the annular shoulder 243 is illustrated as a rectangular corner or edge, it can take on a wide variety of shapes and cross-sectional profiles or contours, including an angled edge, a curved radius or arcuate edge, or others. The annular shoulder 243 is configured and adapted to mutually engage the distal dispensing end 303 of the dispenser 300 when inserted fully into the cavity 240. This provides a stopper for the dispensing end 303 of the housing 301 of the dispenser 300 so as to prevent over-insertion and contact between the forward-most transverse/vertical distal end wall 401 of the inner wall 241 of the cavity and the free end of the applicator 309 that could lead to "bleeding" or leaking of the oral care fluid from the dispenser 300 into the cavity 240 during storage/docking, which could create a mess and loss of oral care fluid. Accordingly, the annular shoulder 243 preferably creates a small gap between the free end of the applicator 309 and the distal end wall 401 of the cavity 241 (see FIG. 7B). The receptacle 400 is further preferably configured and sized to receive the applicator 309 therein and may generally conform to the shape and size of the applicator 309 while providing a suitable circumferential gap therebetween so as to also prevent lateral engagement between the applicator and the wall of the receptacle 400 to prevent leaking. Of course, in some embodiments of the invention, the annular shoulder 243 may be omitted wherein the cavity 241 and dispenser 300 may preferably be mutually configured so that a small gap remains between the end of the applicator 309 and the distal end wall 401 of the cavity 240 when the dispenser 300 is fully seated and docked in the cavity 241 of the handle portion 210 of the toothbrush 200. The annular shoulder 243 and its structural cooperation with the dispenser 300 will be described in greater detail below.

Referring now to FIGS. 7A and 7B concurrently, the structural cooperation between the dispenser 300 and the toothbrush 200 in the storage or docked state will be discussed in greater detail. As illustrated, the oral care system 100 is in the storage state. When in the storage state, the dispenser 300 is slidably positioned within the cavity 240 of the handle 210 of the toothbrush 200 as illustrated. A majority of the length of the dispenser 300 is nested within the cavity 240 of the toothbrush, and preferably at least 75% of the length of the dispenser 300 is nested within the cavity 240 of the toothbrush 200. Most preferably, 75% to 95% of the length of the dispenser 300 is nested within the cavity 240 of the toothbrush 200 in the storage or docked state.

When in the docked or storage state, the annular groove 304 of the dispenser 300 matingly receives the annular ridge 242 of the inner wall 241 of the cavity 240, thereby non-fixedly securing the dispenser 300 in its place. The mating of the groove 304 and the ridge 242 secures the dispenser in place until the user applies sufficient axial force so as to overcome the mating interaction between the groove 304 and the ridge 242, thereby dislodging the dispenser 300 from the toothbrush 200 for use. The exact force required to overcome the mating engagement will be dictated by the respective size, tolerances and materials of construction of the groove 304 and the ridge 242.

The resilient outer layer 307 of the dispenser 300 further facilitates the non-fixed securing between the dispenser 300 and the toothbrush 200 in that the outer layer 307 is compressed by the ridge 242 and/or other portions of the inner wall 241. Furthermore, the compression of the resilient outer layer 307 increases the amount of axial force needed to overcome the increased frictional contact between the inner wall 241 and the outer surface 305 of the housing 301 of the dispenser 300.

The mating between the groove 304 and the ridge 242 also performs another function in that the mating interaction forms a hermetic seal between the wall 242 and the outer surface 305 of the dispenser 300. This hermetic seal prevents water and other fluids that may compromise the integrity of the applicator 309 and/or the activity of the oral care fluid from entering the cavity 240. The compression of the resilient outer layer 307 also adds to this effect. In addition to keeping water and other unwanted fluid from entering the cavity 240 when the dispenser is in the storage state, the hermetic seal also prevents the applicator from drying out during periods of non-use.

When in the docked or storage state, the annular shoulder 243 also assists in the role of maintaining the integrity of the applicator 309 and the oral care fluid during periods of non-use and/or brushing with the toothbrush 200. More specifically, when in the storage state, the annular shoulder 243 contacts (and slightly compresses) the outer surface 305 of the housing 301, thereby forming a second hermetic seal and/or barrier that isolates the longitudinal section C of the internal cavity 240 from the longitudinal section B of the cavity 240. Thus, there are two hermetic seals protecting the longitudinal section C and the applicator 309 from the outside environment in the storage or docked state. Of course, only one or the other may be used. Moreover, one or both of the hermetic seals may also be formed by mere contact between the outside surface 305 of the dispenser 300 and the inner wall 241.

The hermetic seal formed by the annular shoulder may be especially helpful in preventing unwanted leaking and/or drying of the applicator 309 because of the small free volume available in the longitudinal section C of the cavity 240. In other embodiments, the dispenser 300 may be non-fixedly secured within the cavity 240 of the toothbrush 200 by a mere compression fit and/or frictional surface contact between the dispenser 300 and the internal wall 241.

Figure 8:
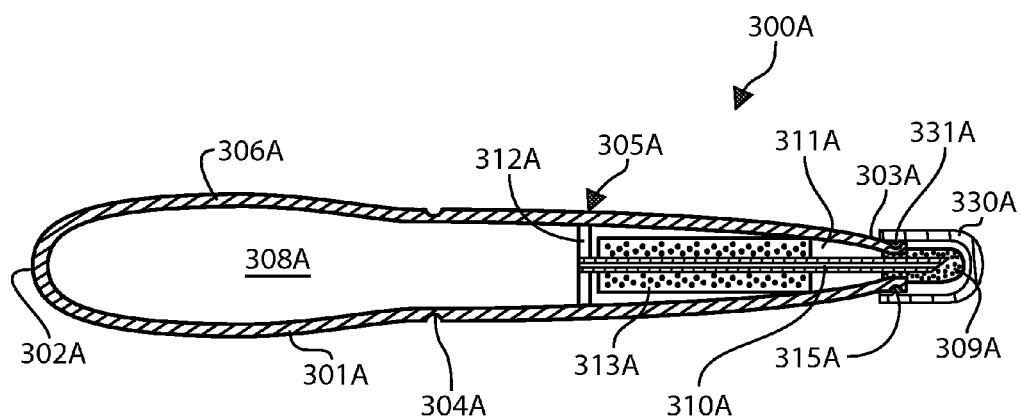
FIG. 8 is a longitudinal cross-sectional view of a dispenser according to an alternative embodiment of the invention having a cap enclosing the applicator.

Referring now to FIG. 8, an alternative embodiment of a dispenser 300A is illustrated according to the present invention. The dispenser 300A is identical to that of the dispenser 300 of FIGS. 4 and 5 with the exception that the dispensing end 303A is adapted to have a cap 330A secured thereto and is constructed of a single layer 306A of material. In order to avoid redundancy, a detailed discussion of those components of the dispenser 300A that are substantially identical to that of the dispenser 100 is omitted. However, for reference and clarity, like numbers are used to identify like parts with the exception of the alphabetical suffix "A" being added.

The dispensing end 303A of the housing 301A of the dispenser 300A includes a surface feature (in the form of an annular groove 315A) for mating with a corresponding structure (in the form of an annular ridge 331A). Mating between the annular groove 215A of the housing 301A with the annular ridge 331A of the cap 330A non-fixedly secures the cap 330A to the housing 301A, thereby enclosing the applicator 309A so as to prevent leaking and/or drying out of the fluid. While a groove/ridge mating assembly is exemplified to hold the cap 330A in place, other surface features and structures that can matingly engage and/or cooperate with one another can be used. Structures and methods of attaching a cap to a tubular body are known in the art.

The housing 301A of the dispenser 300A is also a single layer 306A construction. The material of the single layer 306A should provide the necessary structural rigidity and be compatible with the oral care fluid.

Figure 9:
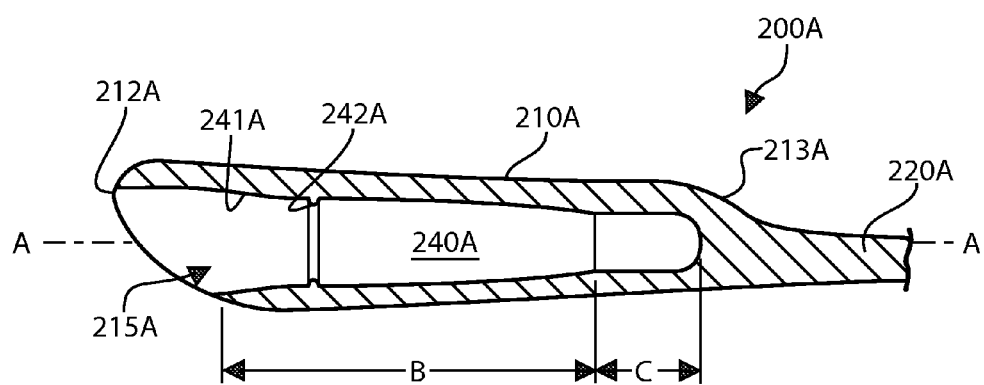
FIG. 9 is a longitudinal cross-sectional view of a toothbrush having a storage cavity designed to accommodate the dispenser (with the cap) of FIG. 8 according to the present invention.

Referring now to FIG. 9, a toothbrush 200A specifically designed to accommodate the dispenser 300A with the cap 330A remaining on is illustrated. The toothbrush 200A is identical to that of the toothbrush 200 of FIGS. 1-7B with the exception that the internal cavity 240A is shaped differently to accommodate the dispenser 300A with the cap 330A. In order to avoid redundancy, a detailed discussion of those components of the toothbrush 200A that are substantially identical to that of the toothbrush 200 is omitted. However, for reference and clarity, like numbers are used to identify like parts with the exception of the alphabetical suffix "A" being added.

Figure 10:
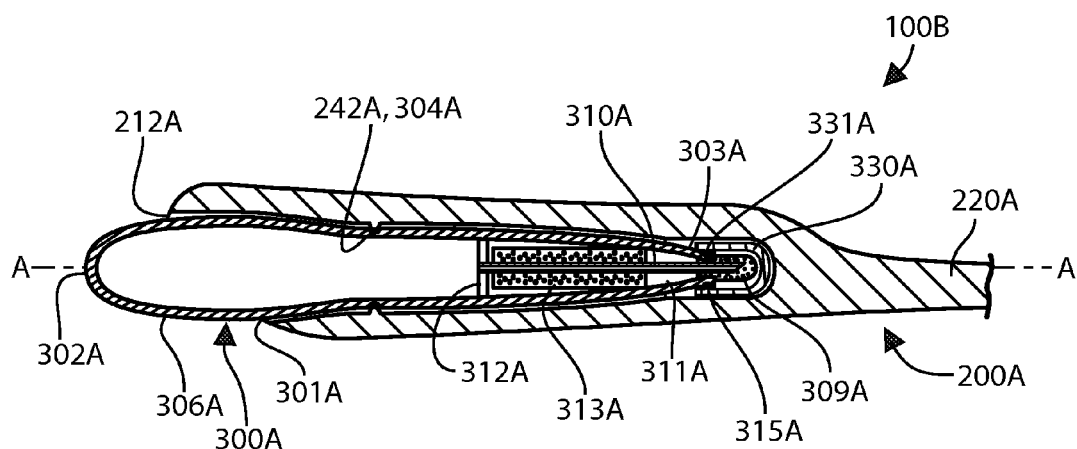
FIG. 10 is a longitudinal cross-sectional view of the toothbrush of FIG. 9 wherein the dispenser (with the cap) of FIG. 8 is non-fixedly secured within the storage cavity.

The internal cavity 240A of toothbrush 200A has a section C that is designed to accommodate the cap 330A of the dispenser 300A. Because the cavity 240A accommodates the dispenser 300A with its cap 330A attached, there is no need for a shoulder to be built into the wall 241A as the cap 330A forms a second hermetic seal for the applicator 309A. The dispenser 300A (with the cap 330A) is shown in the storage position within the toothbrush 200A in FIG. 10.

Figure 11:
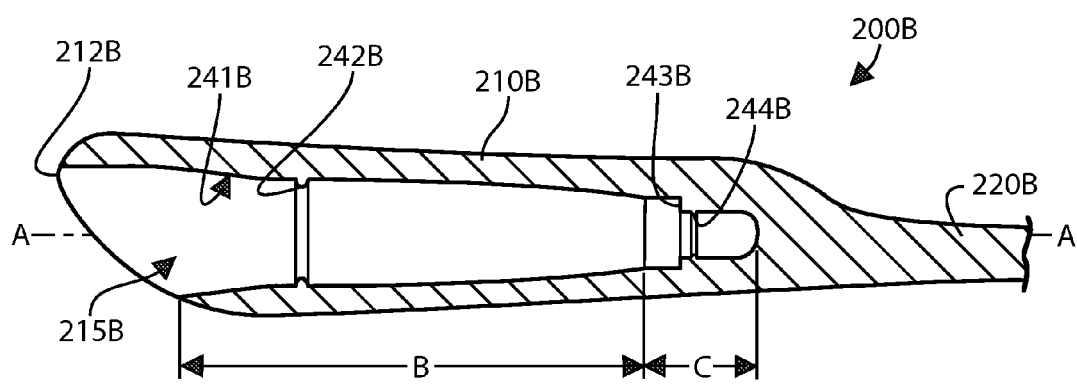
FIG. 11 is a longitudinal cross-sectional view of a toothbrush having a storage cavity designed to accommodate the dispenser of FIG. 8 (without the cap) according to the present invention.
Figure 12:
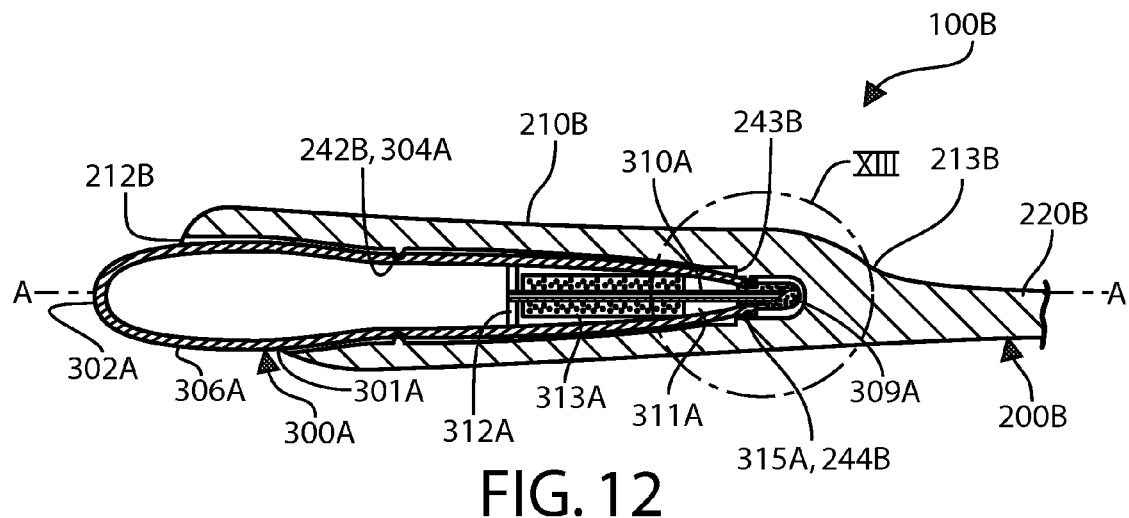
FIG. 12 is a longitudinal cross-sectional view of the toothbrush of FIG. 11 wherein the dispenser of FIG. 8 (without the cap) is non-fixedly secured within the storage cavity.
Figure 13:
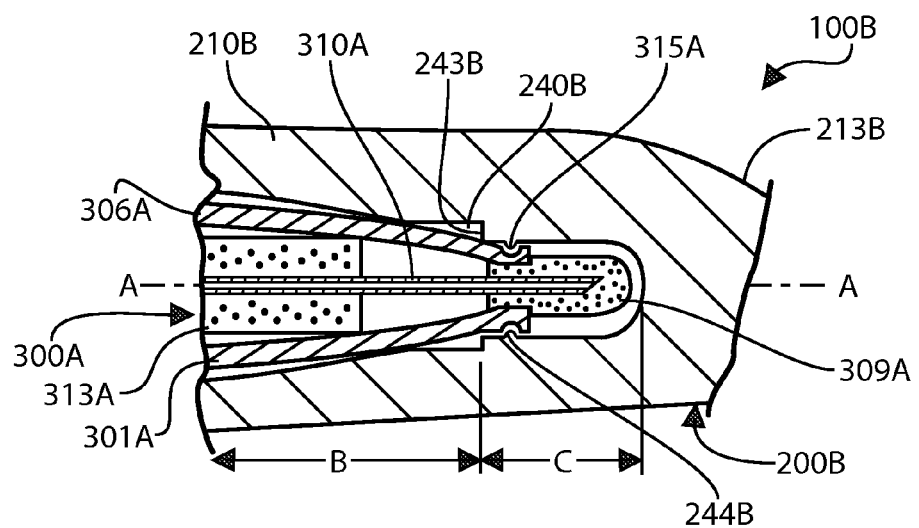
FIG. 13 is a close-up view of area XIII of FIG. 12.

Referring now to FIGS. 11-13 concurrently, a toothbrush 200B specifically designed to accommodate the dispenser 300A without the cap 330A on is illustrated. The toothbrush 200B is identical to that of the toothbrush 200 of FIGS. 1-7B with the exception that the longitudinal section C of the internal cavity 240B is shaped differently to accommodate the dispenser 300A without the cap 330A. In order to avoid redundancy, a detailed discussion of those components of the toothbrush 200B that are substantially identical to that of the toothbrush 200 is omitted. However, for reference and clarity, like numbers are used to identify like parts with the exception of the alphabetical suffix "B" being added.

The longitudinal section C of the cavity 240 B is designed to accommodate the applicator 309A of the dispenser 300A without its cap. Of particular interest is the fact that the longitudinal section C of the cavity 240B is specifically designed to mate with the annular groove 315A located at the dispensing end 303A of the dispenser 300A. Specifically, the inner wall 241B further comprises an annular ridge 244B located in the longitudinal section C of the cavity 240B. When the dispenser 300A is in the storage state (without the cap) within the toothbrush 200B, the annular ridge 244B mates with the annular groove 315B of the dispenser 300B, thereby sealing and enclosing the applicator 309A.

Conceptually, the inner wall 240B of the longitudinal section C of the cavity 240B is contoured to be identical to the structure of the cap 330A. Thus, even though the cap 330A is removed, the same level of protection and conservation of the applicator 309A (and the fluid) is achieved. As a result, the groove 304A can be omitted if desired. The same surface feature (exemplified as the groove 315A) of the dispenser 300A can be used to: (1) secure a cap 330A to protect the applicator 309A during shipping, manufacturing and/or when on sale; (2) assist with non-fixedly securing the dispenser 300A within the cavity 240B in the storage state; and (3) seal and protect the applicator 309A in the storage state.

As a result of the aforementioned changeability between the cap 330A and the longitudinal section C of the cavity 240B, the oral care system 100B is especially suitable for sale as a kit. Replacement dispensers 300A can be sold without the need to keep track of the cap 330A once it is removed and used with the toothbrush 200B.

The oral care system 100 of FIGS. 1-7B (or the other oral care systems and/or components exemplified in FIGS. 8-13) can also be sold as a kit. Any kit can include at least one toothbrush 200 and one dispenser 300 holding an oral care fluid. In other embodiments, a kit may include at least one toothbrush 200 and a plurality of dispensers 300; each dispenser 300 holding a different oral care fluid formulation (e.g. whitening, enamel protection, anti-sensitivity, fluoride, tartar protection, etc.). The dispensers 300 may further be marked with indicia and/or color coded to identify and correspond with the particular oral care formulation contained inside. In yet further embodiments of the kit, toothbrush 200 may have a user-replaceable head 230 and the kit may include one or preferably more such heads of different types and/or configurations of tooth cleaning/engaging elements 235 and/or tongue cleaners.

Figure 14:
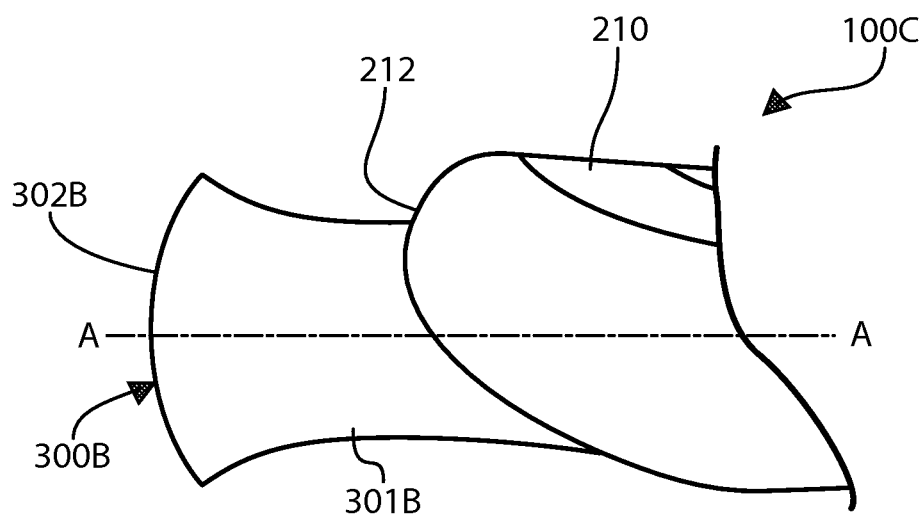
FIG. 14 is a side view of the gripping end of a dispenser protruding from the handle of the toothbrush according to one embodiment wherein the gripping end is shaped for ease of gripping.
Figure 15:
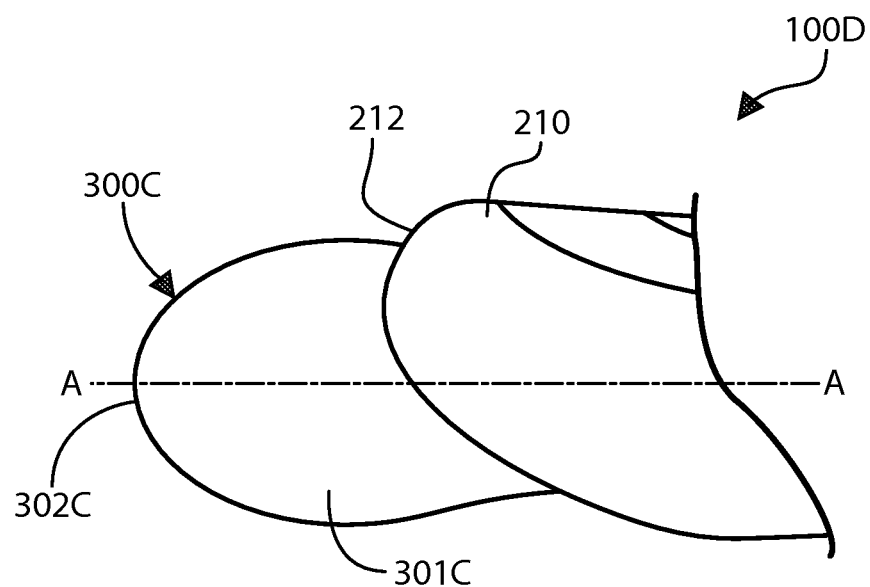
FIG. 15 is a side view of the gripping end of a dispenser protruding from the handle of the toothbrush according to another embodiment wherein the gripping end is shaped for ease of gripping.

Referring now to FIGS. 14 and 15 concurrently, the oral care systems 100C and 100D are illustrated. The oral care systems 100C and 100D are identical to that of the oral care systems of FIGS. 1-13 with the exception that gripping ends 302B, C of the dispenser 300B, C are shaped so that a user can easily grasp the dispensers 300B, C for removal from the toothbrushes 200. Dispenser 300B has a flared end while dispenser 300C has a bulbous end.

FIGS. 16-34 show an alternative embodiment of an oral care system 500 according to another embodiment of the present invention. In this embodiment, as further described below, the toothbrush handle has a longitudinally elongated opening leading to a cavity adapted for removably receiving a dispenser therein. The opening in this alternative toothbrush handle is formed along a substantially longitudinal portion of the handle, whereas the opening 215 in the handle portion 210 of the toothbrush 200 previously described with respect to the oral care system 100 (see, e.g. FIG. 6) is substantially located in the proximal end 212 portion of the handle 210 and axially aligned with the longitudinal axis A-A. Furthermore, whereas the oral care fluid dispenser 300 is axially inserted into and removed from the handle 210 and its internal cavity 240 in the embodiments exemplified in FIGS. 1-15, the dispenser in this alternative oral care system embodiment 500 is at least partially laterally/transversely insertable into the handle for seating and mounting. Also, as further described herein for this alternative embodiment, the dispenser itself may form a substantial portion of the handle of the toothbrush which is gripped by the user thereby advantageously providing ready access to and convenient use of the dispenser. More specifically, the dispenser in this alternative embodiment conceptually forms a circumferential section of the transverse cross-sectional area of the handle, which can be thought of a par-cylindrical section.

Referring initially now to FIGS. 16-19, the alternative embodiment of the oral care system 500 generally includes a toothbrush 600 and a dispenser 700 removably disposed therein. The toothbrush 600 and the dispenser 700 may be generally similar to the toothbrush 200 and the dispenser 300 in structure, manufacture, and functionality to the oral care system 100 and its components as already described above with respect to FIGS. 1-15, except for differences as specially noted in the description of the oral care system 500 which follows.

The dispenser 700 is movable between a storage state (shown in FIG. 16) in which the dispenser is docked or mounted in the toothbrush handle 610 and an application state (shown in FIG. 17) in which the dispenser 700 is dismounted or removed from the handle 610 and ready for use in an oral care regimen. When removed, the dispenser 700 is preferably completely separated and isolated from the toothbrush 600.

With continuing reference to FIGS. 16-20, the toothbrush 600 generally includes a handle portion 610, a neck portion 620 and a head portion 630. The handle 610 can be a single or multi-part construction. The handle 610 extends from a proximal end 612 to a distal end 613 along a longitudinal axis A-A. The handle 610 includes a front portion 660 defining a front surface 652, a rear portion 661 defining a rear surface 653, and a pair of opposing and spaced peripheral or lateral side surfaces 650, 651 extending between the front and rear surfaces 652, 653. The front portion 660 of the handle 610 is fixedly attached to the distal end 613 portion of the handle (i.e. distal sheath portion 661 in one embodiment) and extends longitudinally to the proximal end 612 of the handle 610. Accordingly, as further explained herein, the front portion 660 forms a cantilevered portion of the handle 610 that detachably engages and supports the dispenser 700. The handle 610 transitions into the neck 620 at the distal end 613 of the handle that supports toothbrush head 630 via the handle

610. While the neck 620 generally may have a smaller transverse cross-sectional area to the handle 620, the invention is not so limited.

With continuing reference to FIGS. 16-20, the toothbrush head 630, neck 620, and handle 610 of the toothbrush 600 may be formed as a single unitary structure, or in other embodiments the these parts may be formed as separate structures which are fixedly or detachably assembled together. In some embodiments, the head 630 may be removably attached to the neck 620 thereby forming a user-replaceable head that allows the user to replace heads with worn out tooth cleaning/engaging elements or interchange heads having alternate type cleaning elements. The head 630 generally comprises a front surface 631, a rear surface 632 and a lateral or peripheral side surface 633. The front surface 631 comprises a plurality of oral cleaning elements such as tooth engaging elements 635 extending therefrom for contact with an oral surface and/or interdental spaces. The tooth engaging elements 635 may generally be formed from various types of cleaning elements such as those already described herein with respect to tooth engaging elements 235.

Figure 19:
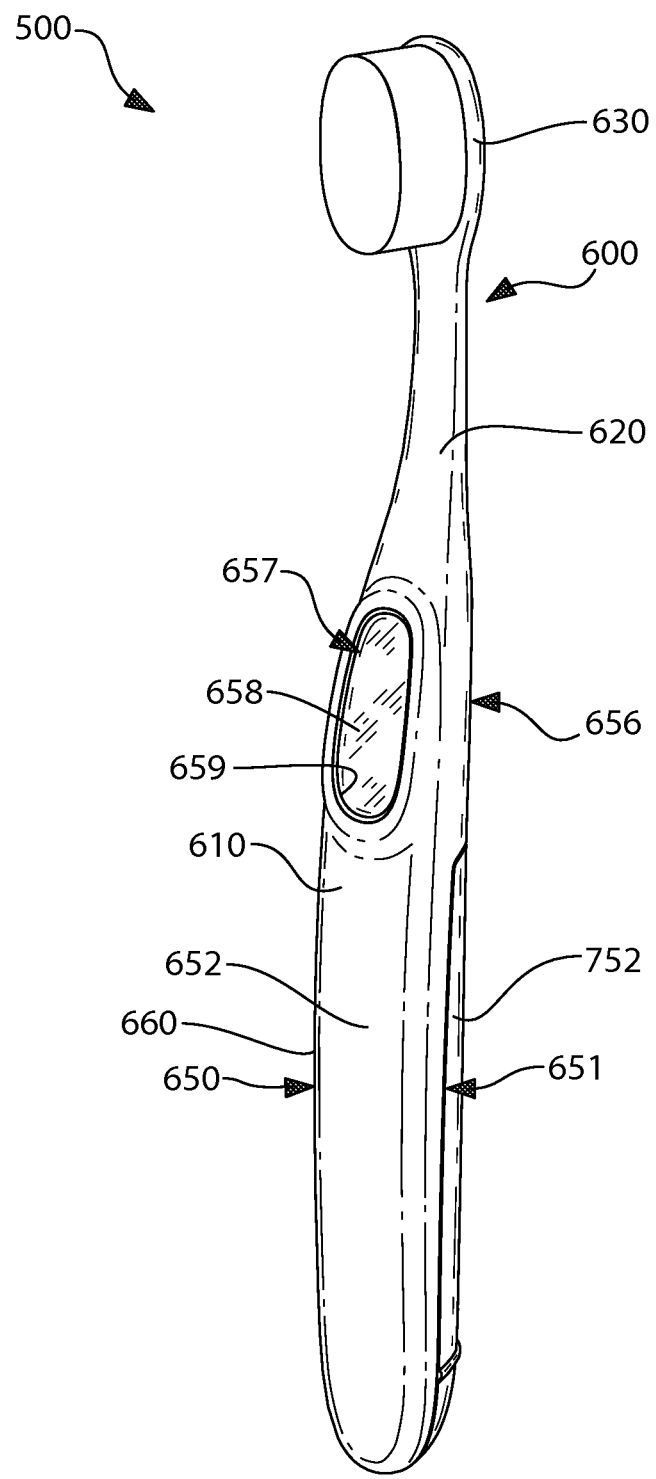
FIG. 19 is a front perspective view thereof.
Figure 20:
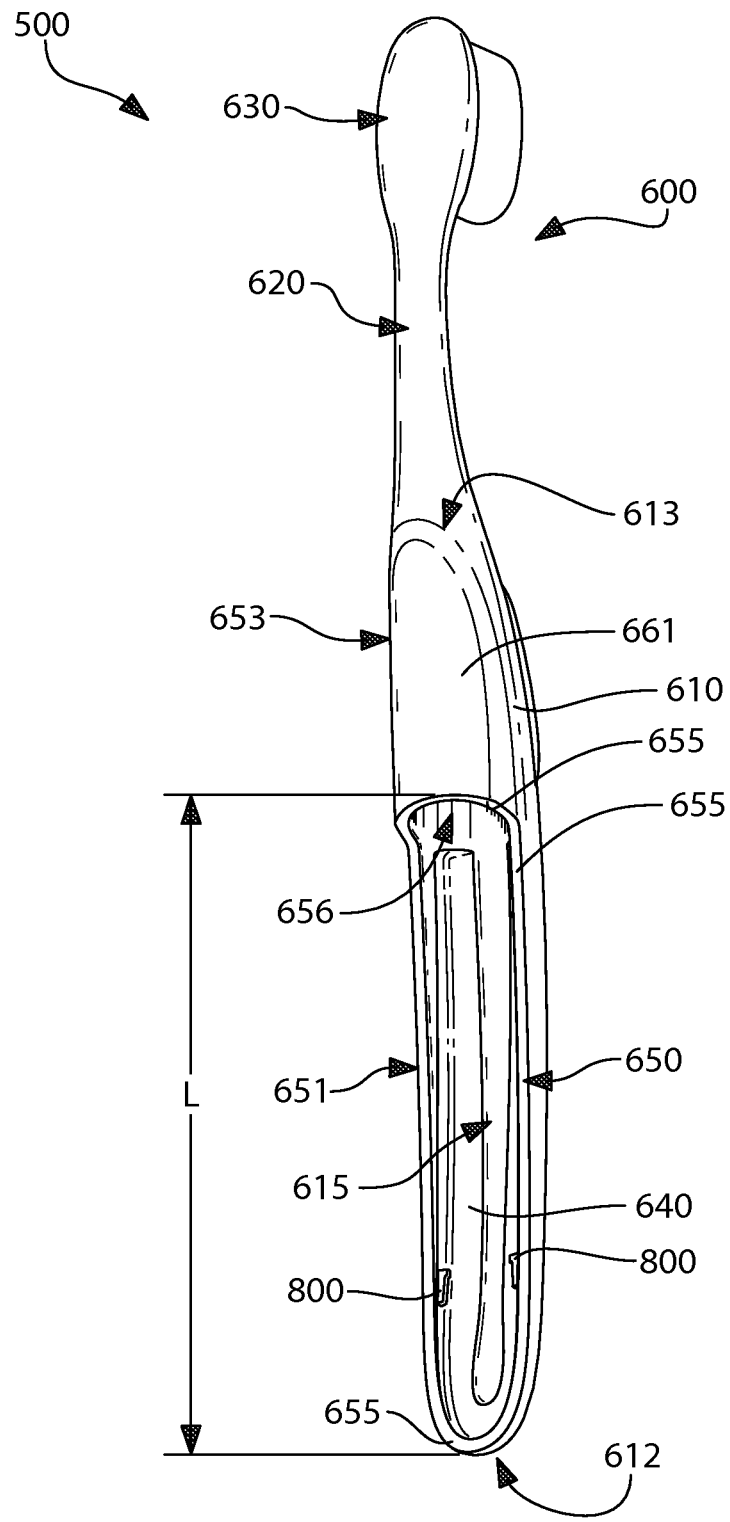
FIG. 20 is a rear perspective view thereof with the dispenser completely removed from the toothbrush.
Figure 21:
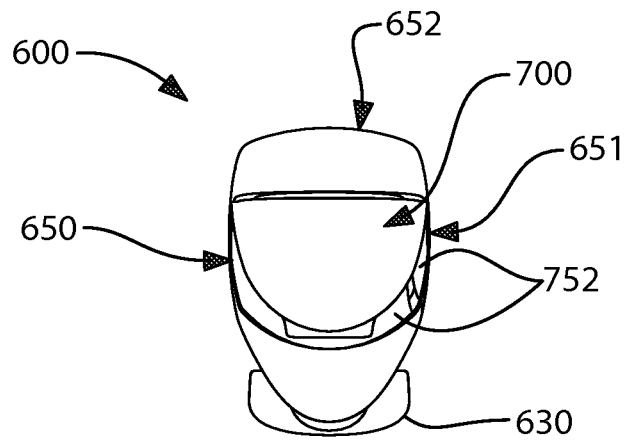
FIG. 21 is a rear end view of the oral care system of FIG. 16 with the dispenser mounted in the toothbrush.
Figure 22:
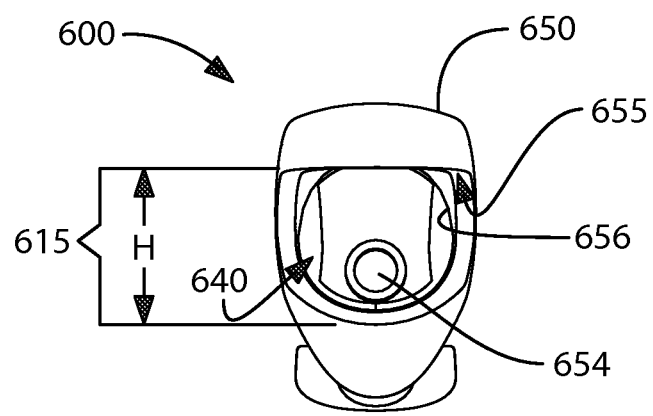
FIG. 22 is a rear end view of the oral care system of FIG. 16 with the dispenser completely removed from the toothbrush.

Referring to FIGS. 16-22, in preferred exemplary embodiments the handle 610 includes a removable portion that defines and incorporates a hand held dispenser 700 adapted to contain and dispense an oral care fluid onto a target surface in an oral cavity of a user. Accordingly, a substantial portion and preferably a majority of the toothbrush handle 610 is cut away both circumferentially and longitudinally to form a largely open longitudinally extending elongated cavity 640 with access opening 615 along the lateral side surfaces 650, 651 and the rear surface 653 of the handle 610 for removably receiving and supporting the dispenser 700. The opening 615 extends both axially and transversely relative to the longitudinal axis A-A of toothbrush handle 610 such that the proximal end 612, the lateral side surfaces 650, 651, and the rear surface 653 of the toothbrush handle are substantially open in structure while only the top surface 652 remains a closed structure, as best shown in FIGS. 20 and 22. When the dispenser 700 is mounted in the toothbrush handle 610, the dispenser 700 and more specifically the housing 701 forms a substantial part of the toothbrush handle 610 in this alternative exemplary oral care system 500 as shown. In one embodiment, the housing 701 of the dispenser 700 forms substantially a majority of the lower rear portion or half of the toothbrush handle 610. The toothbrush handle 610 therefore has only a front portion 660 and partial side surfaces 650, 651 in areas adjacent to the cavity 640, thereby exposing the underside of the handle front portion 660. The front portion 660 of the handle 610 therefore provides merely a supporting core or frame for mounting the dispenser 700 to a rear of the toothbrush 600, wherein the dispenser 700 substitutes for and forms a majority of the lateral side surfaces 650, 651 and rear surface 653 of the toothbrush handle, except for the distal most portion of the handle near the transition to neck portion 620.

Thought of another way, the handle 610 of the toothbrush 600 has a substantially elliptical transverse cross-sectional profile when the dispenser 700 is mounted within the cavity 640, wherein the housing 701 of the dispenser 700 forms a transverse section of this transverse cross-sectional profile. When assembled, a portion of the outer surface of the housing 701 of the dispenser 700 forms a circumferential section of the perimeter of the elliptical transverse cross-sectional profile of the handle 610 while the front portion 660 of the handle 610 forms the remaining circumferential section of the perimeter of the elliptical transverse cross-sectional profile of the handle 610.

In contrast to the embodiment shown in FIGS. 1-3, the maximum transverse cross-sectional size or diameter of the housing 701 of the dispenser 700 is not restricted by the transverse size or diameter of the toothbrush handle 610, unlike the handle 210 (see FIGS. 1-3 and 7A) which must be sized to accommodate a substantial portion of dispenser 300 therein as shown. In certain instances, where desirable, this allows the size of the dispenser 700 and the associated volumetric capacity of the reservoir 708 to be made as large as possible, being limited primarily by only the intended overall size selected for the toothbrush 600 which will fit comfortably in the hand of the user.

Figure 17:
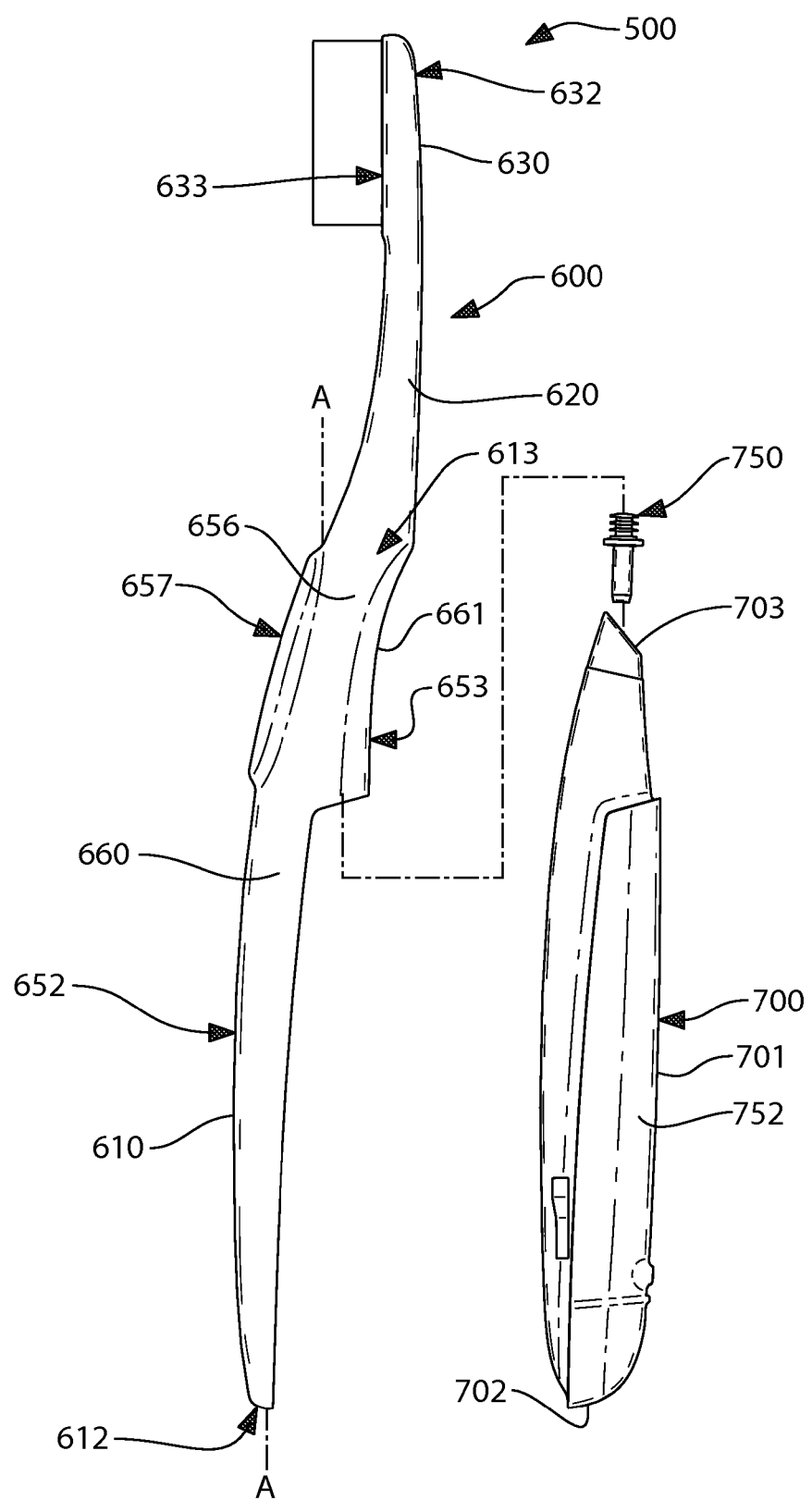
FIG. 17 is an exploded side elevation view thereof with the dispenser shown detached from the toothbrush.
Figure 18:
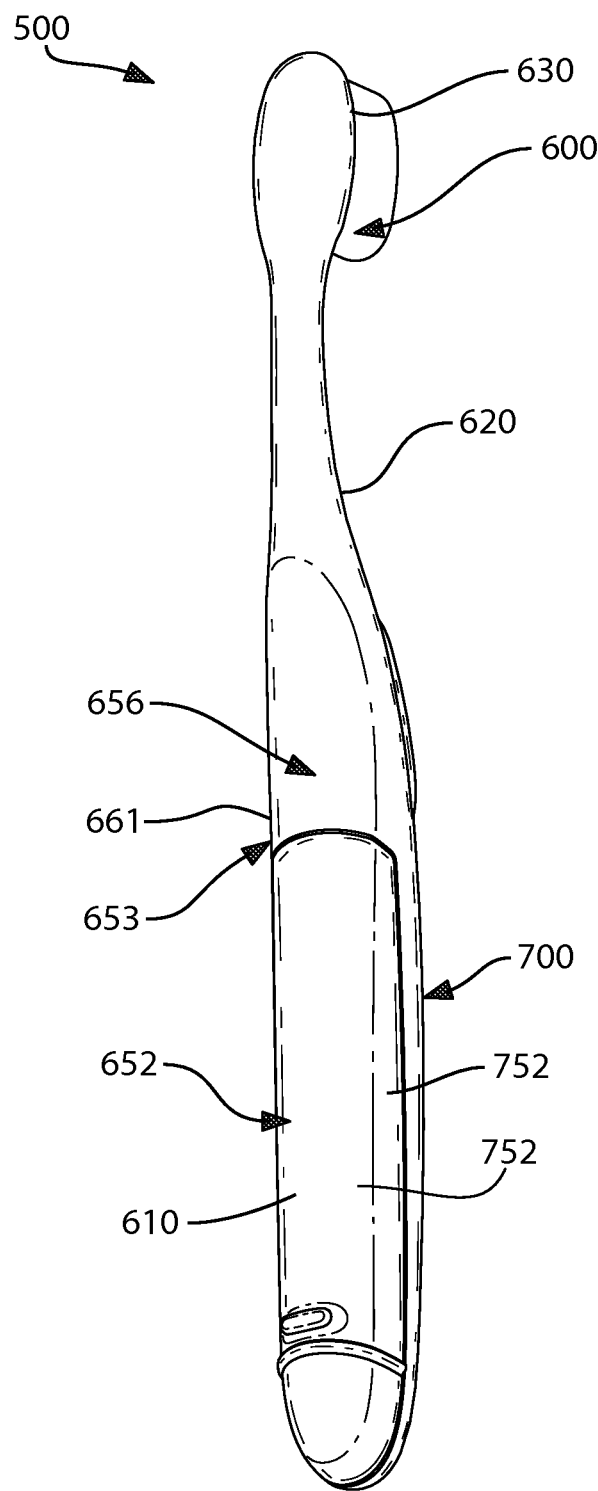
FIG. 18 is a rear perspective view of the oral care system of FIG. 16 with the dispenser mounted in the toothbrush.
Figure 31:
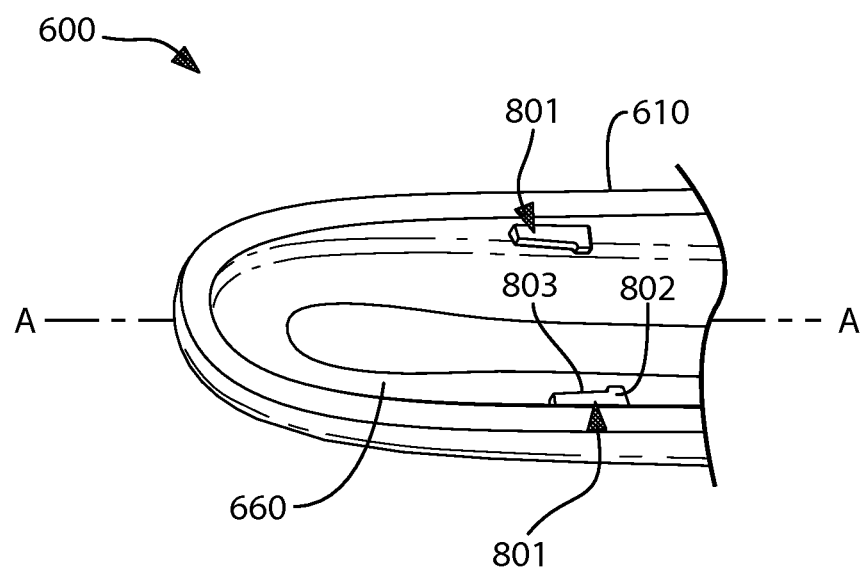
FIG. 31 is an enlarged perspective view of the rear or proximal end of the top portion of the toothbrush handle showing mounting tabs disposed thereon.

Referring primarily to FIGS. 17, 20, and 31, the toothbrush handle 610 and more particularly the front portion 660 defines peripheral lateral, rear, and front mounting edges 655 which are configured and sized to mate with and engage corresponding peripheral mounting edges 763 on the dispenser housing 701 (best shown in FIGS. 23-24 and 34) when the dispenser 700 is attached to the toothbrush 600. Preferably, the edges 655 and 763 of the handle 610 and the dispenser housing 701 respectively mutually align to form a relatively uniform combined circumferential surface when joined, thereby maintaining a smooth transition between the handle 610 and the dispenser housing 701 for user comfort purposes. In some embodiments, all or part of the peripheral mounting edges 763 on the dispenser 700 may be formed on resilient soft grip 752 further described herein elsewhere. The rear surface 753 of the dispenser 700 is also preferably contoured to smoothly transition into mating corresponding with the rear surface 653 of the handle 610.

Referring now to FIGS. 17, 20, 22, and 28, in exemplary embodiments of the cavity 640, the access opening 615 in toothbrush handle 610 has an axial length L (FIG. 20) that preferably extends for at least half the axial length of the handle 610 measured between the distal end 613 and the proximal end 612, and more preferably for a majority of the length of the handle to maximize the volumetric storage capacity of the reservoir 708 of the dispenser 700 and to facilitate gripping the dispenser. In preferred exemplary embodiments, the opening 615 and corresponding cavity 640 extend for approximately more than half of the height H and circumference of the handle 610 as shown in FIG. 22.

Figure 28:
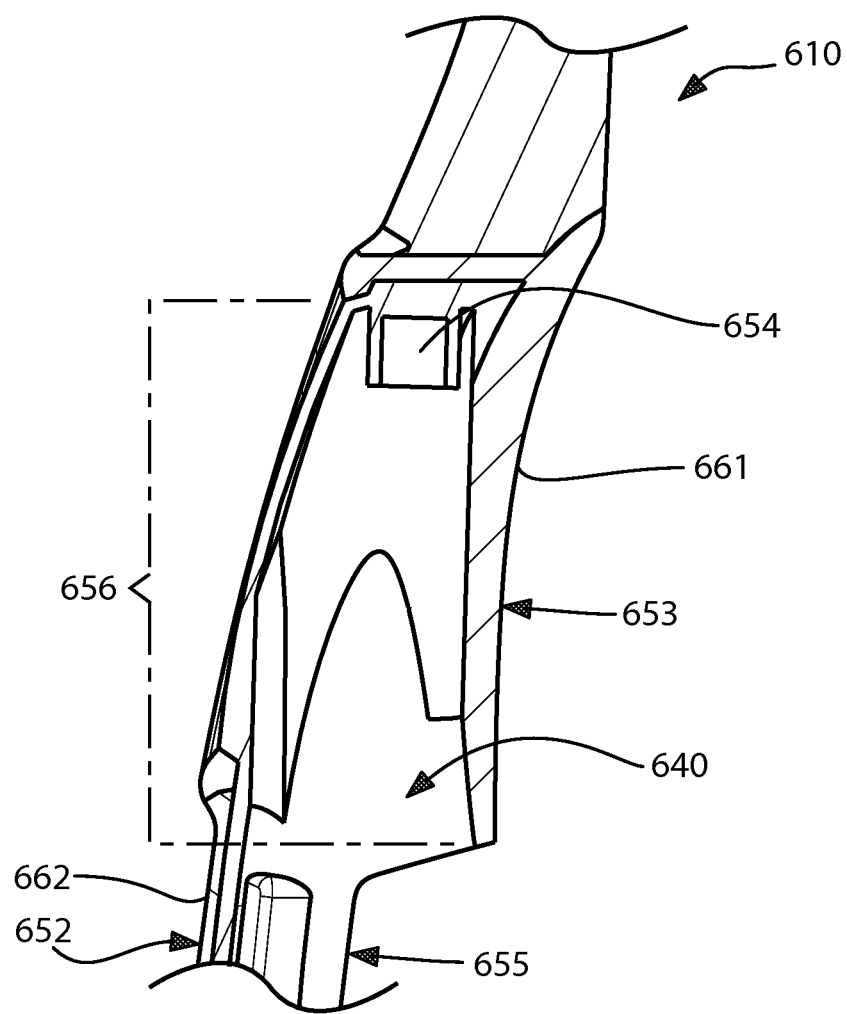
FIG. 28 is an enlarged partial side cross-sectional view of the distal end sheath portion of the toothbrush handle with the dispenser removed.

The distal most portion of the cavity 640 is preferably circumferentially enclosed by the distal end 613 of the toothbrush handle 610 as best shown in FIGS. 20, 22, and 28 to form a generally tubular sheath portion 656 configured and adapted for receiving the distal dispensing end 703 and the applicator 709 of the dispenser 700 therein. This fully enclosed sheath portion 656 facilitates secure docking of the dispenser 700 in the handle 610 and protects the applicator 709 from damage when the dispenser is in the docked or storage state affixed to toothbrush 600. The distal or front end of the sheath portion 656 is closed while the proximal or rear end of the sheath portion is open to receive the distal dispenser end 703 of dispenser 700 therein. In some embodiments, a socket 654 may be provided at the distal-most end of the sheath portion 656 in the cavity 640 that is configured and adapted for receiving an axially protruding plug 750 disposed in the applicator 709 (see FIG. 29) to further assist with securing the distal dispensing end 703. This socket 654, in the exemplified embodiment, is formed into the transverse end wall that closes the distal end of the cavity 640 in the sheath portion 656.

Figure 29:
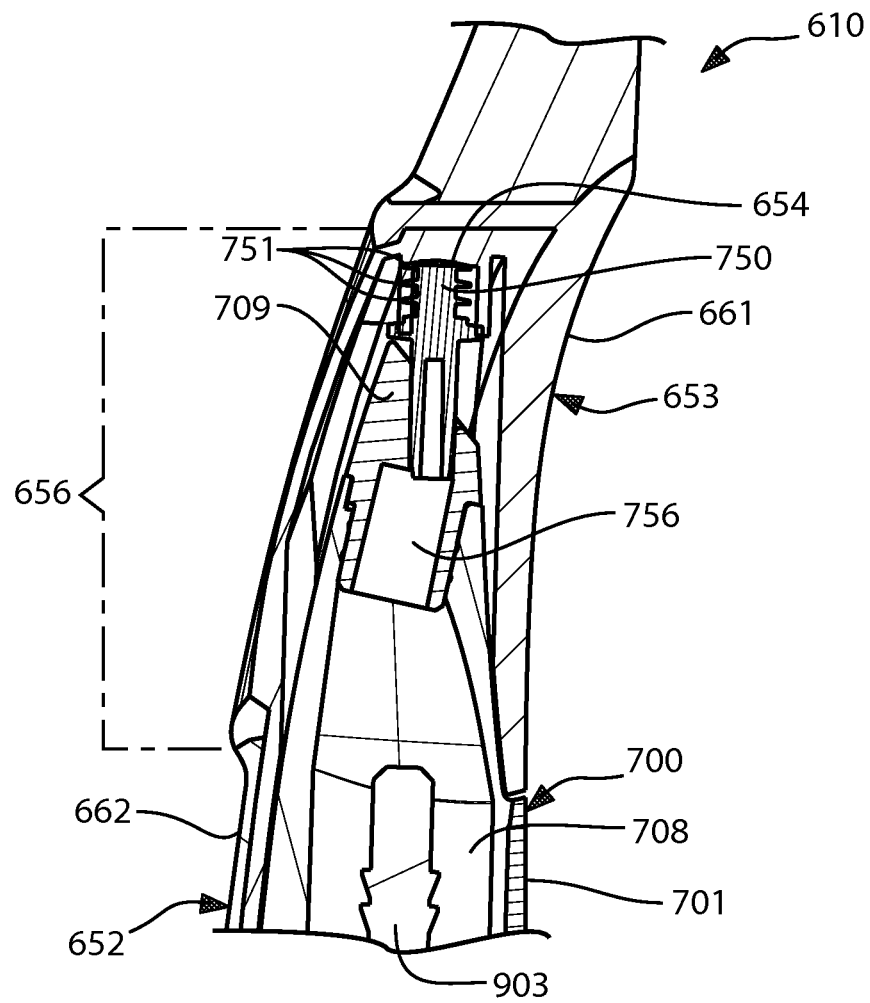
FIG. 29 is an enlarged partial side cross-sectional view thereof with the dispenser mounted in the sheath portion.
Figure 30:
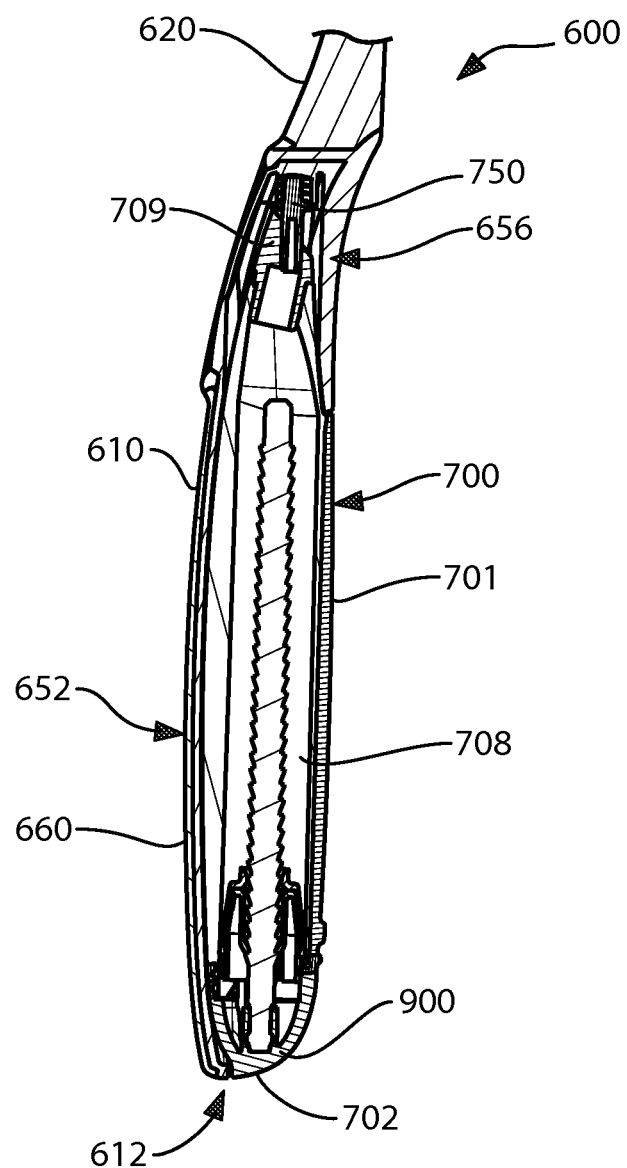
FIG. 30 is a full side cross-sectional view of the handle portion of the toothbrush with the dispenser mounted inside.
Figure 32:
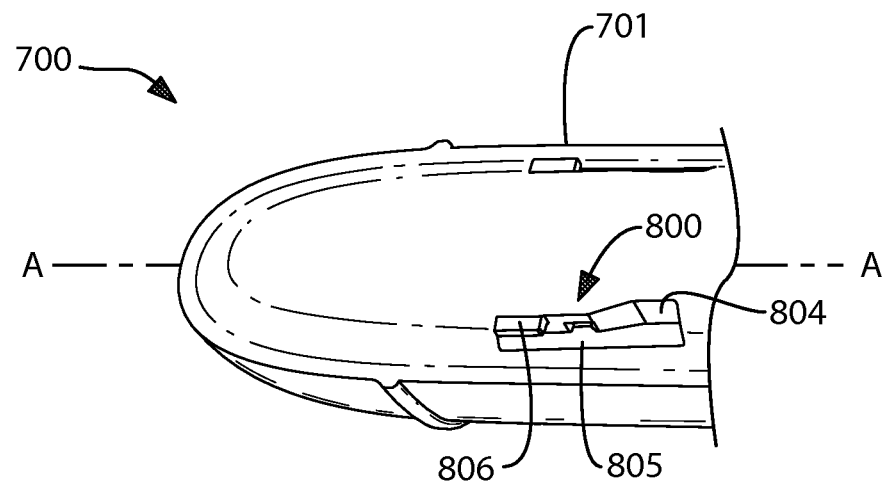
FIG. 32 is an enlarged perspective view of the rear or proximal end of the dispenser showing mounting recesses and locking lugs disposed therein.
Figure 33:
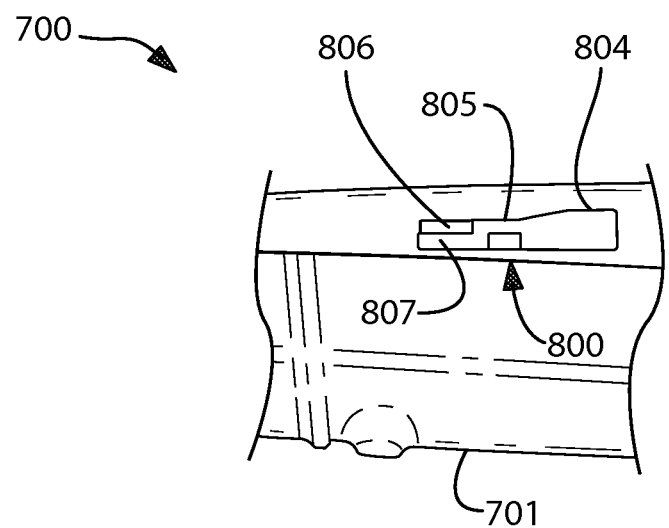
FIG. 33 is an enlarged side elevation view of the rear or proximal end of the dispenser showing the mounting recess and locking lug.

The rear portion of the dispenser 700 is detachably secured to toothbrush handle 610 via a locking mechanism disposed towards proximal end 612 of the handle. Referring to FIGS. 20, 23, 24, and 31-33, the dispenser locking mechanism 800 may be comprised of a cooperating tab and recess locking arrangement in one exemplary embodiment. The dispenser housing 701 includes a pair of laterally/transversely spaced apart mounting recesses 800 which are configured and adapted to receive a pair of laterally spaced apart mounting tabs 801 disposed on toothbrush handle 610. In one embodiment, the mounting tabs 801 are disposed on the underside of the front portion 660 of the toothbrush housing 610 and project inwards towards the longitudinal axis A-A and includes a forward enlarged section 802 and a rearward narrower section 803, as best shown in FIG. 31. The mounting recess 800 correspondingly includes a forward enlarged section 804 and a rearward narrower section 805, as best shown in FIGS. 32 and 33. The locking recess 800 further includes a locking lug 806 disposed in the rearward section 805 which protrudes laterally/transversely outwards from the dispenser 700. When the dispenser 700 is mounted to the toothbrush handle 610, the enlarged section 802 of the mounting tab 801 becomes positioned in and engages the corresponding enlarged section 804 of the mounting recess 800 and the narrower section 803 of the mounting tab 801 becomes positioned in and engages the corresponding narrower section 805 of the mounting recess 800. The locking lug 806 of the mounting recess frictionally engages a rear portion of the narrower section 803 of the mounting tab 801 to removably but securely attach the dispenser 700 to the toothbrush handle 610 via a characteristic "clicking" action. Since the front portion 660 of the toothbrush handle 610 adjacent the cavity 640 is preferably relatively thin in thickness to be at least partially resilient to a degree, the front portion 660 of the toothbrush handle 610 is able to flex laterally/transversely relative to the longitudinal axis A-A in response to the dispenser 700 being inserted therein when the mounting tabs 801 engage the mounting recesses 800. The enlarged sections 802 of the mounting tabs 801 will tend to engage the dispenser housing 701 before the narrower sections 803. The narrower sections 803 are received in the locking portion 807 of the recess 800 beneath the locking lugs 806 and they spring (or click) back inwards into place to complete the mounting. FIGS. 29 and 30 are cross-sectional views showing dispenser 700 fully seated or mounted in toothbrush handle 610.

The dispenser 700 will now be further described. FIGS. 23-26 show various views of the alternative dispenser 700 with FIG. 26 being a longitudinal cross-sectional view of the dispenser 700. In one embodiment, the dispenser 700 is an elongated and generally tubular pen-like structure that may be similar to the dispenser 300 already described herein (see FIGS. 5, 7A, and 7B) with respect to functionality and general construction. Some features of the dispenser 700, including the attachment mechanism for detachable mounting to handle 610, configuration, and other features, however, have been modified as will now be further described.

Figure 26:
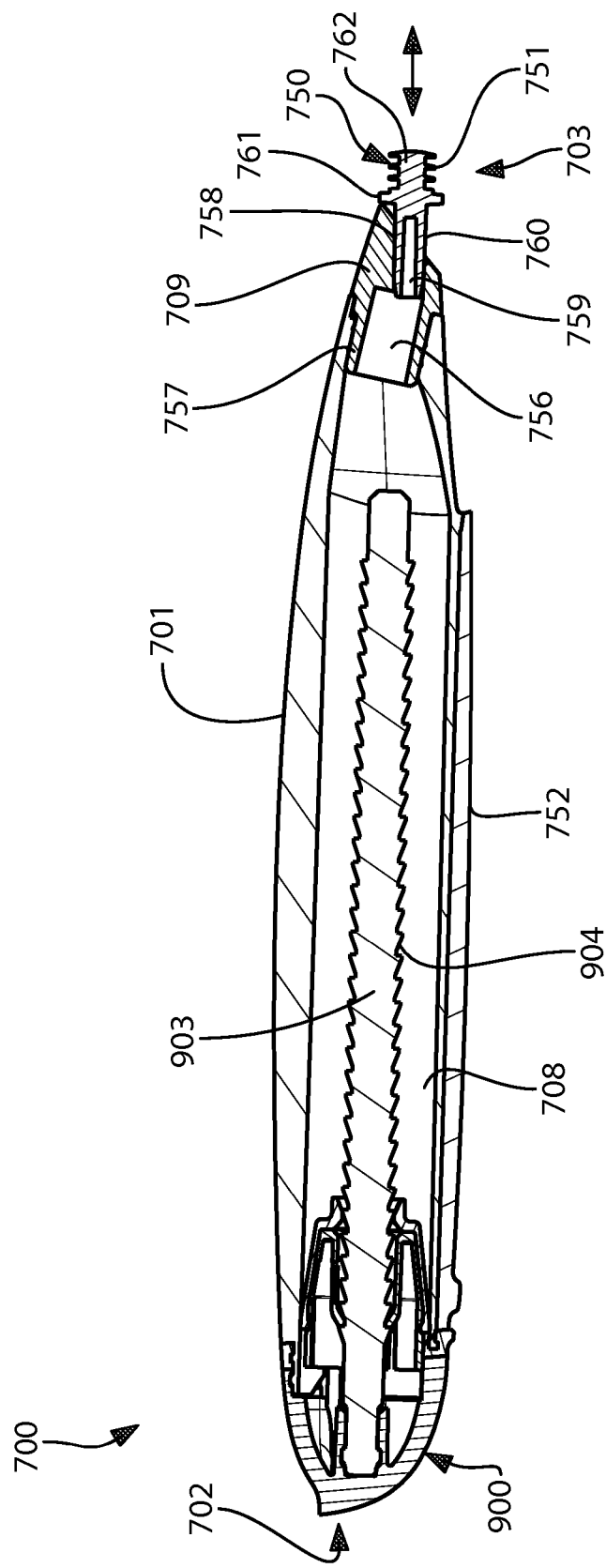
FIG. 26 is a side cross-sectional view thereof.

With continuing reference to FIGS. 23-26, the dispenser 700 includes a housing 701 that extends between a proximal operating end 702 and a distal dispensing end 703. As already noted herein, the housing 701 may be considered to form essentially a removable portion of the toothbrush handle 610. In some embodiments, the housing 701 may comprise inner and outer layers similarly to inner layer 306 and outer layer 307 of housing 301 shown in FIG. 5. Alternatively, in the embodiment as best shown in FIG. 26, the housing 701 has a relatively single layer shell construction formed of a preferably rigid material which may be a relatively rigid hard plastic/polymer such as a thermoplastic similar to materials already described herein with respect to the inner layer 306 of the housing 301. This provides structural rigidity to the dispenser 700. In some embodiments, at least part of the housing 701 may include resiliently deformable flexible portions to allow the user to squeeze and pressurize the contents of the dispenser for delivering the active oral care fluid.

Optionally, in some embodiments, at least a portion of external side of housing 701 may include a soft non-slip resilient grip 752 formed of a material such as an elastomer (e.g. as already described herein with respect to outer layer 307 of housing 301) to provide a slip resistant and comfortable gripping surface for the user. Because the dispenser 700 substitutes for and forms a substantial functional part of the toothbrush handle 610 in this embodiment, the resilient grip 752 in some embodiments preferably covers at least a portion of, and more preferably a majority of the exposed portions of the dispenser 700 when mounted in the handle 710. This facilitates removal and reinsertion of the dispenser 700 in the toothbrush handle 610 by allowing the dispenser 700 to be easily grasped, especially with wet hands after brushing. In at least one embodiment, the grip 752 may cover a majority of the lower half of the dispenser 700 and the housing 701, including the rear surface 753 and portions of the lateral side surfaces 754, 755 of the housing (see, e.g. FIGS. 21, 23-26, and 34). The grip 752 need not cover the front surface 766 or distal dispenser end 703 of the dispenser as these portions will be nested inside the toothbrush handle 610 when the dispenser 700 is seated in the handle 610. The resilient grip 752 may be attached to the housing 701 by any suitable conventional means used in the art and already described herein, including without limitation co-molding and adhesives.

With continuing reference to FIGS. 23-26, the housing 701 forms an internal chamber which defines a reservoir 708 for holding the desired oral care fluid. The oral care fluids that can be used have already been described herein in detail. The reservoir 708 is fluidly coupled to an applicator 709 which protrudes forward from the dispensing end 703 of the housing 701. In this embodiment of the dispenser 700, equivalents of a delivery channel 310 and an overflow chamber 311 (see, e.g. FIG. 4 and description herein) are omitted. Instead, the oral care agent containing fluid is in direct contact with the applicator 709 as best shown in FIGS. 26 and 29. The applicator 709 may include an internal flow conduit 756 which fluidly communicates with reservoir 708 to facilitate uniform wetting of the applicator with the oral care fluid.

Referring to FIGS. 23-26 and 29, the applicator 709 may be constructed of bristles, a porous or sponge material, or a fibrillated material similar to the applicator 309 already described herein. The applicator 709 may also be simply constructed of an elastomeric material, such as TPE. The applicator 709 includes a stem portion 757 in one embodiment which is received in a passage formed into the distal dispensing end 703 of the housing 701 and frictionally engages the inner surface of this passage to retain the applicator 709 in the housing 701. The dispenser 700 further includes a plug 750 which is slidably received and removably retained within an orifice of the applicator 709. In one embodiment, the plug 750 may be formed of polypropylene or an elastomeric material, examples of which are already described herein. In one possible exemplary embodiment, the plug 750 includes a distal plug portion portion 762 and an adjoining proximal plug portion portion 760 which is removably received in an axial orifice, such as passageway 758, formed in the forward end of the applicator 709. The plug 750 is non-unitary and non-integral with respect to the toothbrush 600 and the dispenser 700.

The passageway 758 fluidly communicates with the flow conduit 756 of the applicator 709 and provides an orifice for dispensing the flowable oral care fluid, or other oral care agent, from the dispenser 700. Preferably, the passageway 758 has a smaller cross-sectional internal diameter and transverse flow area than the adjoining flow conduit 756 to restrict and regulate the flow of the oral care fluid from the dispenser 700. Based on the viscosity of the flowable oral care fluid delivered by the dispenser, one skilled in the art can readily determine an appropriate internal diameter (i.e. orifice size) for the passageway 758 to establish a desired dispensing flow rate of the product to a user. In contrast to the porous type applicator 309 shown in FIG. 4 which does not have an open flow delivery conduit or pathway extending completely through the applicator to the outside, the orifice dispensing system used in applicator 709 is advantageously better suited for dispensing more viscous oral care fluids or products such as gels and pastes.

With continuing reference to FIGS. 23-26 and 29, the plug 750, including the plug portions 762, 760 may be generally cylindrical in shape. The plug 750 may further include a radially extending annular flange 761 to prevent over insertion of the plug into the passageway 758 (see FIGS. 26 and 29). The plug portions 760, 762 extend from opposite sides of the annular flange 761 in coaxial alignment along a longitudinal axis of the plug 750. The proximal plug portion 760 comprises a central void 759 extending along the longitudinal axis of the plug 750 while the distal plug portion 762 is a solid cylindrical structure.

With additional reference now to FIGS. 28 and 29, the removable plug 750 may further include a plurality of radially-protruding flexible annular ribs 751 on the distal plug portion 762 which serve several functions. The ribs 751 are configured and adapted to elastically deform and frictionally engage the complementary configured cylindrical socket 654 disposed internally in the toothbrush handle 610 near the distal end 613 at the distal-most portion of the internal cavity 640. The ribs 751 detachably secure the distal dispensing end 703 of the dispenser in the toothbrush handle 701 through cooperation with the plug 750 and the dispenser 700. Of course, other types and/or shapes of protrusions could be provided on the outer surface of the distal plug portion 762 as desired. The plug 750 further provides additional benefits, including preventing spilling of the oral care fluid while the dispenser 700 is being filled during manufacturing, reducing the chance of the oral care fluid to leak after the manufacturing phase, and keeping the exposed applicator 709 tip clean in between uses by the user.

Figure 27:
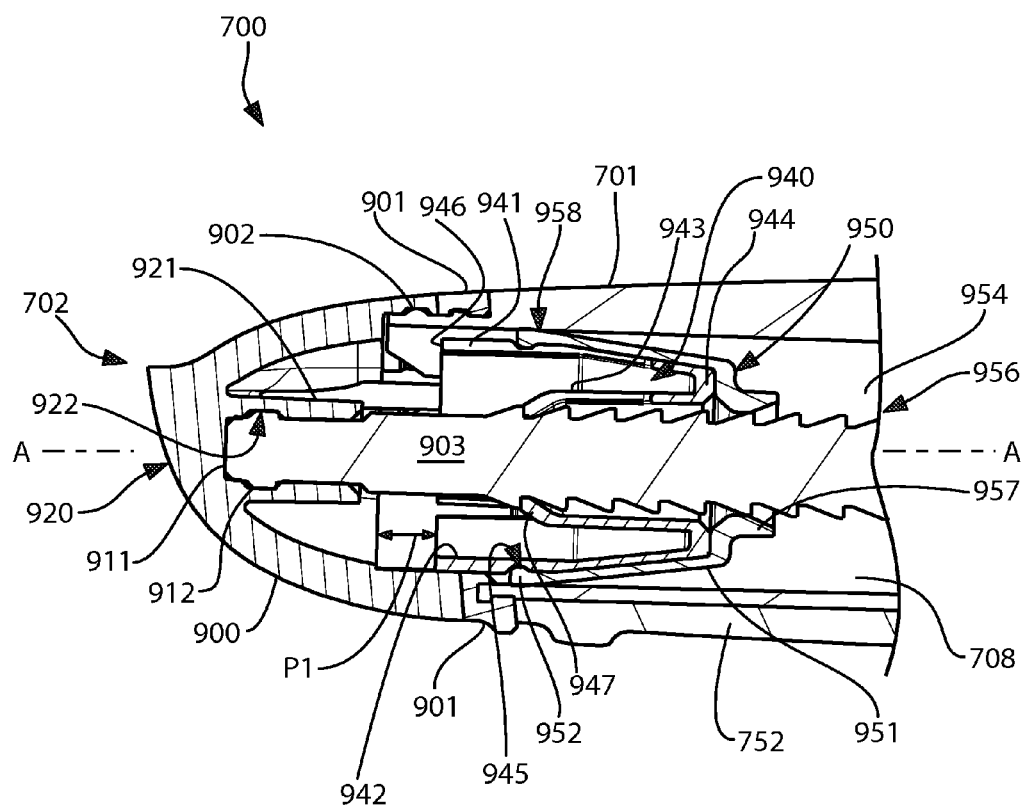
FIG. 27 is an enlarged partial side cross-sectional view of the proximal end portion of the dispenser of FIG. 26.
Figure 34:
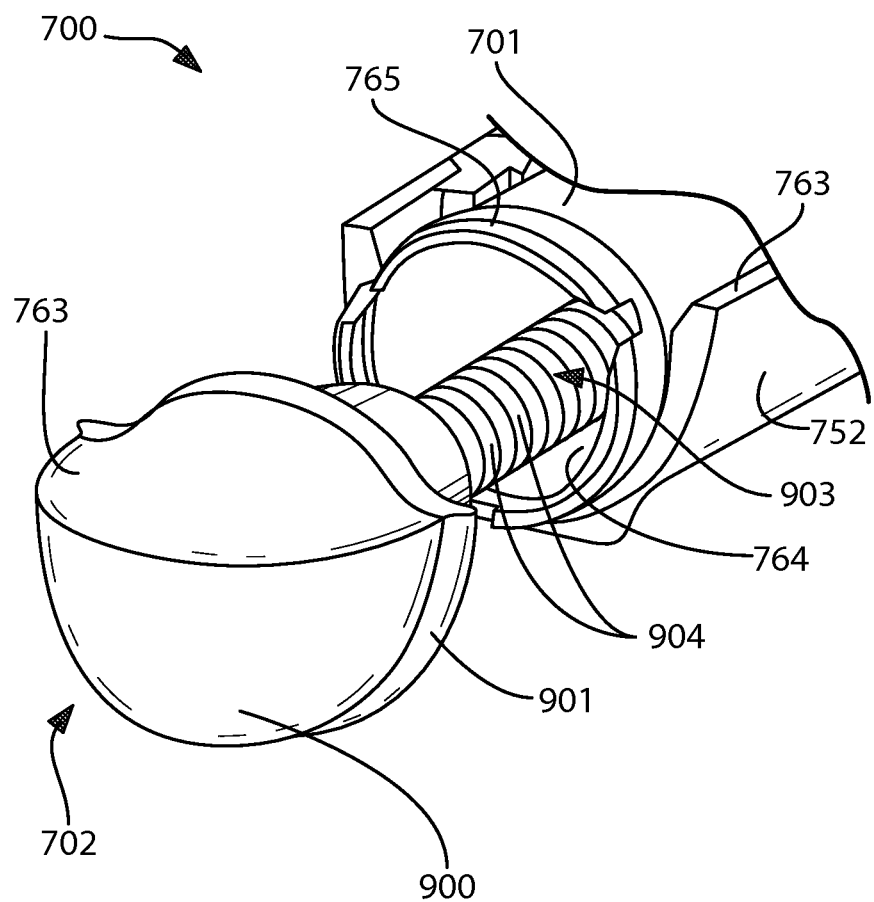
FIG. 34 is an enlarged perspective view of the rear or proximal end of the dispenser housing showing an end cap partially removed from the dispenser.
Figure 35:
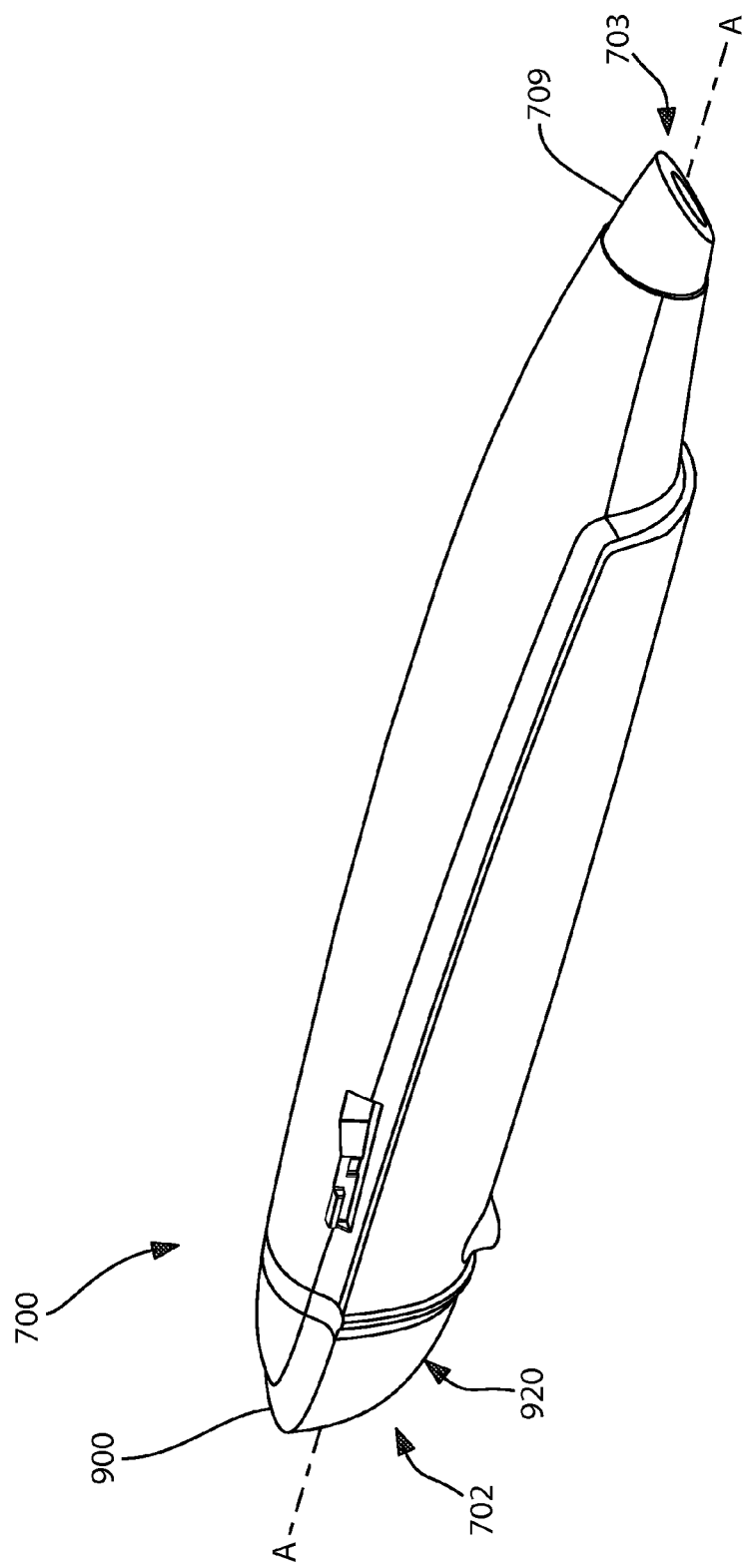
FIG. 35 is a perspective view of the dispenser of the oral care system of FIG. 16.

Referring to FIGS. 26, 27, and 34, the rear or proximal operating end 702 portion of dispenser 700 includes an attachable cap 900 that seals and closes proximal end 702 of the dispenser. The cap 900 may be formed of a resilient elastomeric material in some embodiments and acts as a push-button actuator to advance an internal rod 903 mechanism of the dispenser 700 and thereby releases oral care fluid through the applicator 709. The cap 900 compresses to perform the advancing function and then returns to its original shape. The cap 900 also provides for user comfort both when toothbrush 600 is used in the brushing mode with dispenser 700 fully seated therein and when dispenser 700 is detached from the toothbrush for applying the oral care fluid to the teeth. In one embodiment, the cap 900 preferably includes an annular collar or flange 901 that engages a groove formed on the proximal or rear end of dispenser 700. The flange 901 is preferably made of a more rigid material than the cap 900 to advantageously provide a surface for pressing the cap into position on dispenser 700 after the dispenser is filled with the oral care fluid during the manufacturing process. The proximal end portion 702 of the dispenser housing 701 may further include one or more raised ridges 765 disposed near the annular edge 764 that engage corresponding annular grooves 902 (see FIG. 27) on the cap 900 for securing the cap 900 and providing a rear hermetic seal of the dispenser 700. In some embodiments, as shown, the axially forward extending rod 903 may be mounted on the cap 900 for further securing the cap to the dispenser housing 701. As best shown in FIG. 27, the rod 903 may include a plurality of axially spaced apart angled serrations or teeth 904 which are configured to engage a retaining mechanism 905 disposed in the proximal end 702 of dispenser 700.

Figure 16:
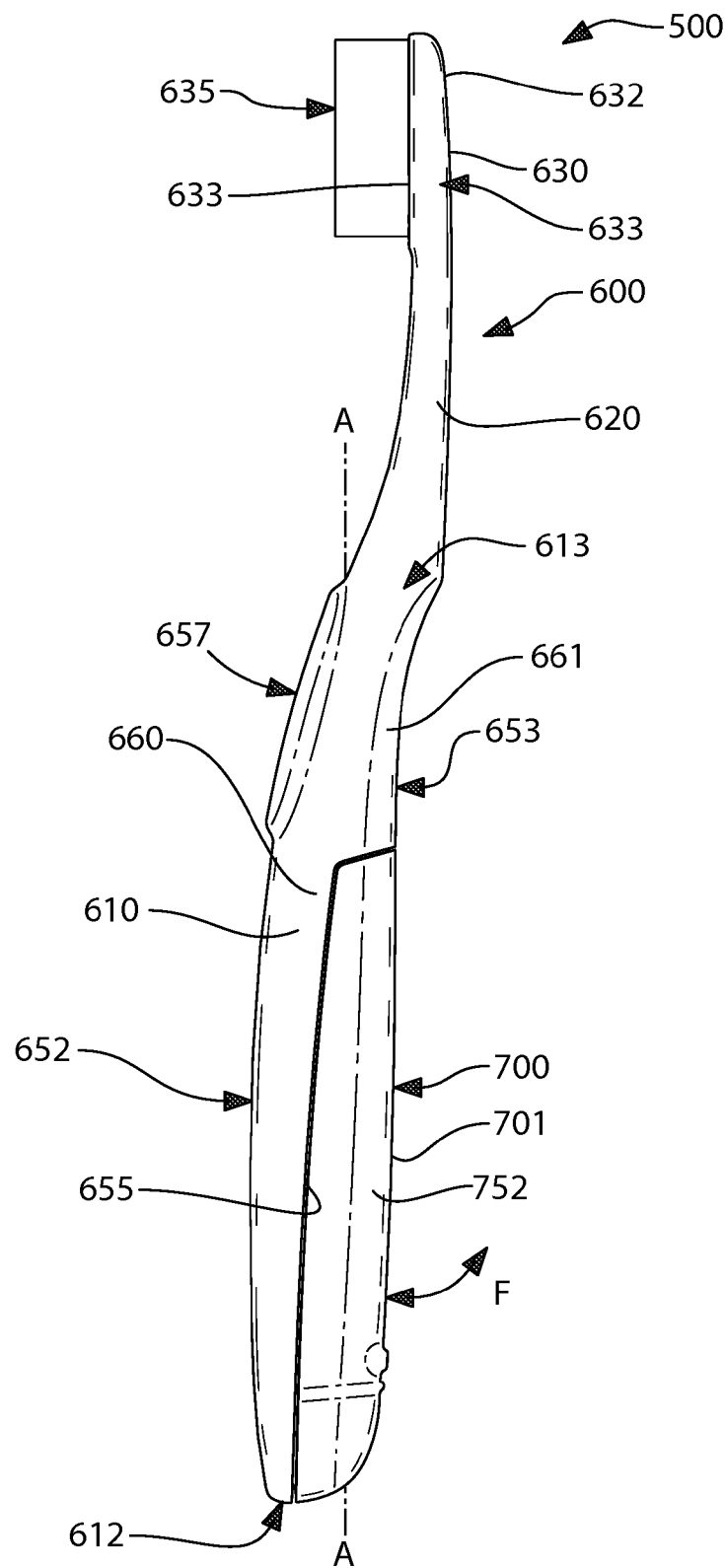
FIG. 16 is a side elevation view of a second alternative embodiment of an oral care system including a toothbrush and fluid dispenser according to an embodiment of the present invention.

An exemplary method of manufacturing and using the toothbrush 600 and the dispenser 700 will now be briefly described. During manufacture, the dispenser 700, with the plug 750 inserted therein so that the proximal plug portion 760 is disposed within and seals the conduit 758 while the distal plug portion 762 extends from the dispenser 700, is provided. The desired oral care material is then flowed into the reservoir 708 of the dispenser via an opening other than dispensing orifice, such as the opening formed when the cap 900 is removed. Once the desired amount of fluid has been flowed into the reservoir 708, the cap 900 is coupled to the housing 701, thereby sealing the opening into the reservoir 708. The dispenser 700, with the plug inserted therein as described above, is then detachably coupled to the toothbrush handle 610 by inserting the extending distal plug portion 762 of the plug 750 into the socket 654 and snapped into place as described in greater detail above, and as shown in FIG. 16. It should be noted at this time that the concepts described herein regarding the plug could be incorporated into any of the embodiments of the oral care system disclosed herein.

The toothbrush 600 with the dispenser 700 in the storage state as shown in FIG. 16 is then provided to a user. The dispenser 700 is fully seated and secured in the toothbrush handle 610 as shown with a bottom portion of the housing 701 near the proximal end 702 being lockingly engaged by the cantilevered front portion 660 of the handle 610 (via mounting tabs 801 and locking lugs 806 shown in FIGS. 31-33) and the distal dispensing end 703 being slidably frictionally engaged by the sheath portion 656 of the handle (see FIG. 29). After the user completes brushing his/her teeth with the toothbrush 600, or alternatively before brushing his/her teeth, the user grasps the dispenser housing 701 (preferably at grip portion 752 if provided) and pulls the proximal portion of the dispenser 700 near or at proximal end 702 outwards and away from toothbrush handle 610 by applying a force F initially in a direction generally transverse to longitudinal axis A-A. Since the distal dispenser end 703 is still seated in sheath portion 656 of toothbrush handle 610 (see, e.g. FIG. 29), this initial force applied by the user is a pivotal action with the dispenser end 703 acting as a pivot point. The rear or proximal half of to the dispenser 700 will therefore pivot in an arcuate path initially away from toothbrush handle 610 (see, e.g. FIG. 16 and applied force F) at an angle with respect to the toothbrush handle and longitudinal axis A-A. The locking lugs 806 of the dispenser housing 701 releases the mounting tabs 801 on the toothbrush handle 610 (see FIGS. 31-33) and the mounting tabs are withdrawn from mounting recesses 800 of the dispenser housing. This uncouples the proximal end 702 of the dispenser 700 from the toothbrush handle 610. The user may next unsheathe or withdraw the distal dispenser end 703 from the sheath portion 656 of toothbrush handle 610 by sliding dispenser 700 rearward in a generally axial direction along the longitudinal axis A-A towards the bottom or proximal end 612 of the handle.

During uncoupling, the plug 750 of the dispenser 700 slides out of the applicator 709 and is retained in the socket 654 in the toothbrush handle 610, thereby exposing the applicator 709. Retention of the plug within the socket 654 during use (and after the initial assembly during manufacturing) is accomplished by designing the distal plug portion 762 and/or the socket 654 so that the axial force required to remove the distal plug portion 762 from the socket 654 is greater than the axial force required to remove the proximal plug portion 760 from the passageway 758. In one embodiment, the ratio of the axial force required to remove the distal plug portion 762 from the socket 654 compared to the axial force required to remove the proximal plug portion 760 from the passageway 758 is in a range of 1:1.5 to 1:6.

The difference in required axial force can be accomplished in a number of ways, including, without limitation: (1) adjusting the tolerances so that a tighter fit is achieved between the distal plug portion 762 and the socket 654 than between the proximal plug portion 760 and the passageway 758; (2) designing the outer surface of the distal plug portion 762 and/or the inner surface of the socket 654 so that the frictional engagement between the outer surface of the distal plug portion 762 and the inner surface of the socket 654 is greater than the frictional engagement between outer surface of the proximal plug portion 760 and the inner surface of passageway 758, which can be done through selection of materials, area of contact, and/or modifying the surface topography; (3) creating interlocking geometry on the outer surface of the distal plug portion 762 and the inner surface of the socket 654; (4) designing the proximal plug portion 760 to be more easily compressible than the distal plug portion 762 by either using a more compressible material(s) and/or creating a void 759 in the proximal plug portion 760; (5) adding protuberances, such as the ribs 751, to the outer surface of the distal plug portion 762 to increase the compression fit in the socket 654; (6) adding an adhesive into the socket 654 prior to the initial installation; (7) tapering the proximal plug portion 760; and/or (8) combinations thereof.

Once the plug 750 is disengaged from the passageway 758 of the applicator 709, the user may then fully withdraw the dispenser 700 from the toothbrush 600 as shown in FIG. 17. As illustrated, the dispenser 700 is now in the application state and completely uncoupled and separated from the toothbrush 600. The user then applies the oral care fluid to the teeth and/or other portions of the oral cavity as required with the applicator 709.

To reinsert the dispenser 700 back into toothbrush handle 610, the user simply repeats the foregoing steps in reverse. During said reinsertion, the proximal plug portion 760 of the plug slides back into the passageway 758 and the mounting tabs 801 are snap locked into the mounting recesses 800, thereby returning the dispenser 700 back to the storage state, as shown in FIG. 16. It should be noted that whereas the dispenser 300 of FIGS. 1-15 is removed and reinserted from the toothbrush 200 by applying only an axial force and motion to the dispenser 300, the dispenser 700 of FIGS. 16-33 is removed from toothbrush 600 by a combination of forces and motions both transverse and axial as described above.

According to another aspect of the invention, the toothbrush handle 610 may further include a window 657 (best shown in FIG. 19). In a preferred exemplary embodiment, the window 657 may comprise a relatively clear and transparent insert 658 which is disposed in an aperture 659 in the handle 610 having a complementary shape to the insert. The window insert 658 may be formed as a separate piece and attached to handle 610 by any suitable means used in the art such as adhesives, heat or ultrasonic welding, or may be co-molded with the handle. Preferably, the window 657 is positioned on the toothbrush handle 610 so that at least a portion of the applicator 709 of dispenser 700 is visible through the window when the dispenser 700 is mounted in the handle 610. The window 657 communicates to the consumer/user that there is another product incorporated into the toothbrush 600. In some possible embodiments, different dispensers 700 may be available that contain different oral care fluids or formulations (e.g. whitening, enamel protection, anti-sensitivity, flavors, etc.). The applicator 709 and/or distal dispensing end 703 of dispenser housing 701 may be color-coded and/or include indicia to correspond with a particular type of oral care fluid formulation contained inside. This would allow the user to quickly identify which formulation is presently contained in the dispenser 700 seated in the toothbrush 600. Such different type dispensers 700 may be included in a kit as already described herein with reference to toothbrush 200 and dispenser 300.

According to another aspect of the invention, the fluid dispensing system operable to deliver and dispense a flowable fluid from the dispenser 700 will now be described in greater detail. Of course, the fluid dispensing system, along with the principles and components, described below, could be used in conjunction with a wide variety of dispenser types.

Figure 36:
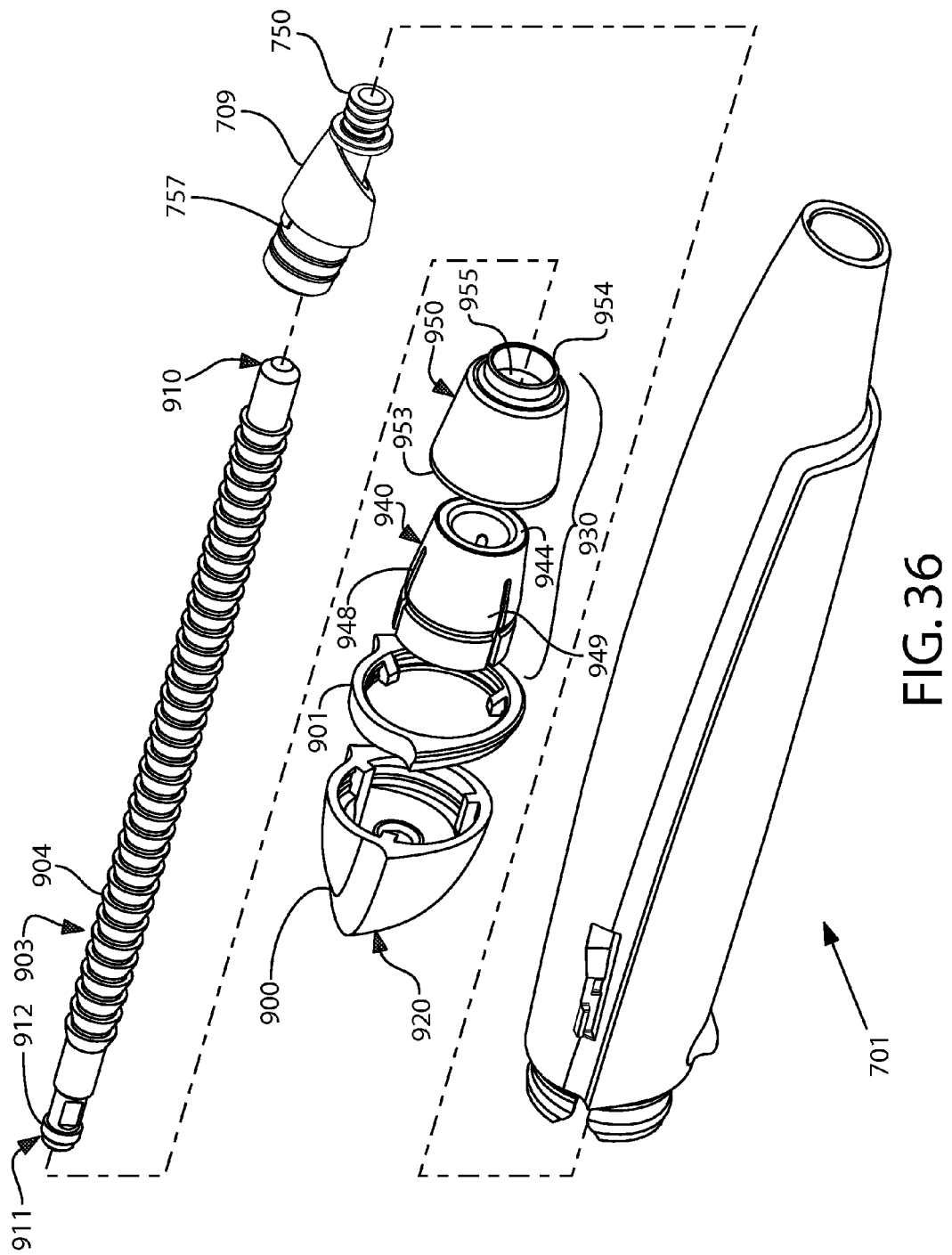
FIG. 36 is an exploded view thereof.
Figure 37:
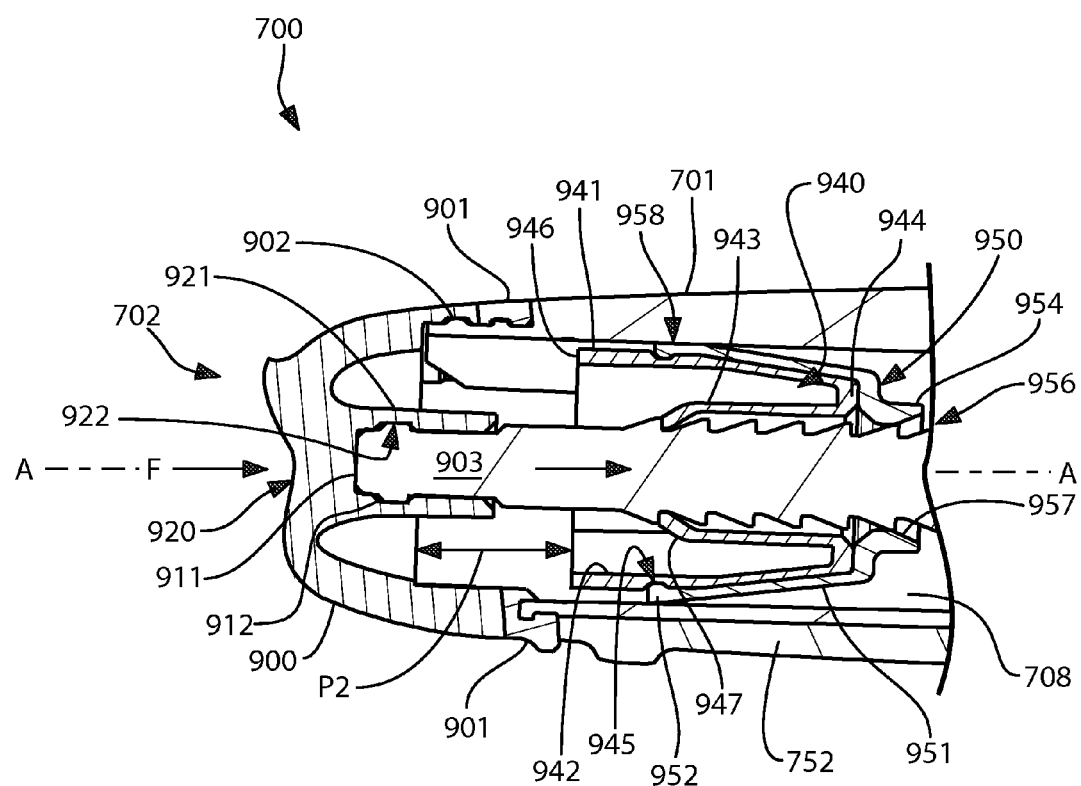
FIG. 37 is a partial cross sectional view of the proximal end of the dispenser thereof showing a push button actuator in an activated depressed position.
Figure 38:
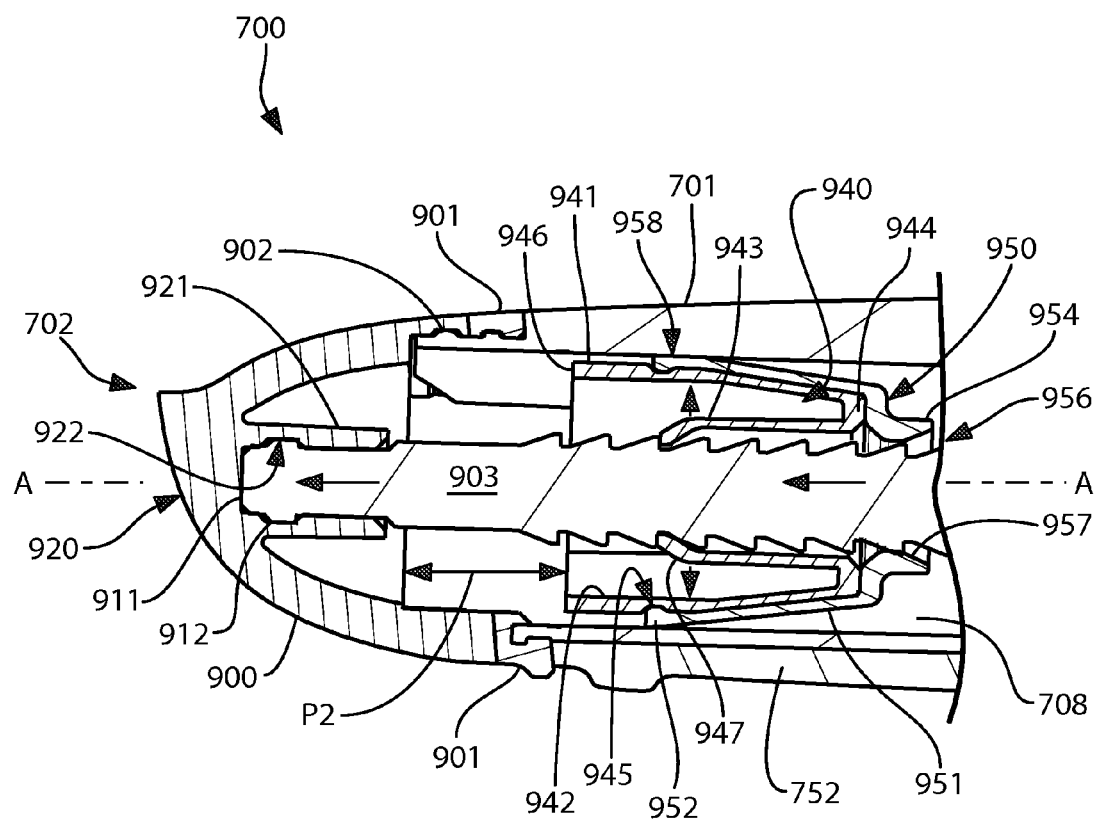
FIG. 38 is a partial cross sectional view of the proximal end of the dispenser thereof showing a push button actuator in a released and inactivated un-depressed position.

Referring initially to FIG. 36, the fluid dispensing system in one embodiment may include a ratchet mechanism including a rack, such as ratchet rod 903, with angled serrations or teeth 904, a cooperating plunger assembly 930 including a pawl 943 for engaging rod 903, and an axially-biased actuator, such as push-button actuator 920, (see also FIGS. 27 and 37-38). The ratchet mechanism advances the plunger assembly 930 forward within reservoir 708 of dispenser 700 to deliver the fluid to a user through the applicator 709. The components of the ratchet mechanism will now be further described individually in greater detail.

With reference to FIGS. 27 and 35-38, the ratchet rod 903 is movably disposed within the housing 701 of the dispenser 700 and extends into the reservoir 708 for translational axial movement in the direction of longitudinal axis A-A. The ratchet rod 903 includes a distal free end 910 and an opposite operating end 911 for mounting to and engagement with the actuator 920 (see FIG. 36). The operating end 911 in one embodiment is configured to engage a complementary configured portion of the actuator 920 which operably couples the rod to the actuator 920. In one possible embodiment, as best shown in FIGS. 27 and 37-38, the operating end 911 of the ratchet rod 903 engages a corresponding socket 921 formed in (or connected to) the actuator 920 of the end cap 900. The ratchet rod 903 may include an annular radially protruding annular flange, such as ring 912, which is seated in a complementary configured annular groove 921 formed inside the socket 921 on the actuator 920 to lock the rod 903 to the actuator 920. The interlock between the ratchet rod 903 and the socket 921 is preferably designed so that the rod will not pull out of the socket 921 during normal operation and movement of the rod 903 when used to dispense the oral care fluid from the dispenser 700. Other suitable arrangements of mounting the ratchet rod 903 to the actuator 920 may be provided and the invention is not limited to the embodiment shown and described herein.

In some embodiments, the ratchet rod 903 is preferably made of a relatively rigid material, such as polypropylene. Other suitable plastics and materials with similar mechanical properties, however, may be used so long as rod 903 is sufficiently structurally rigid to function as a rack in the ratchet mechanism.

When actuated by the actuator 920, the ratchet rod 903 is forced into a reciprocating motion, thereby moving axially in two opposite directions between a first proximal refracted or non-dispensing position and a second distal extended or dispensing position in which an oral care fluid is dispensed from dispenser 700, as further described herein. The angled teeth 904 on the ratchet rod 903 are configured to engage the plunger assembly 930 so that a ratcheting motion is imparted to the plunger assembly 930 by the rod 903 during actuation and retraction. The angled teeth 904 therefore are oriented to slope rearward toward the proximal end of the dispenser 700 as best shown in FIGS. 27 and 37-38.

Referring to FIGS. 27 and 36-38, the plunger assembly 930 is disposed and axially slideable within the reservoir 708 formed internally within the housing 701 of the dispenser 700 (see also FIG. 30). In one possible preferred embodiment, the plunger assembly 930 may be of two-piece construction including an inner generally cup-shaped plunger 940 and a mating outer cup seal 950 having a complementary cup-shape which receives the plunger 940 at least partially therein. The plunger 940 and the cup seal 950 are configured and sized to nest together wherein the cup seal serves as a sheath covering at least a portion of the inner plunger 940 as shown. In one embodiment, at least a portion of the plunger 940 is insertable into and lockingly engages the cup seal 950 (best shown in FIGS. 27 and 37-38) such that these components members remain joined and move in unison when actuated by the ratchet rod 903. In some embodiments, the plunger assembly 930 is configured such that a portion of the inner plunger 940 extends rearward and outward from the cup seal 950. In a further embodiment, the plunger 940 does not contact the interior surface of the dispenser housing 701 which is only engaged by the outer cup seal 950 to optimize material selection for each component as further described herein.

The inner cup-shaped plunger 940 and the outer cup seal 950 may be generally cylindrical, frusto-conical, or combination thereof in cross-sectional shape as shown in FIGS. 27 and 36-38. In some embodiments, as shown, portions of the plunger 940 and the cup seal 950 may be cylindrical in shape while other portions may be frusto-conical. In one embodiment, the rear or proximal portions of the plunger 940 and the cup seal 950 may be cylindrical in shape and adjoining portions forward thereof, including intermediate portions and front portions, may be frusto-conical.

With reference to FIGS. 27 and 36-38, the inner cup-shaped plunger 940 includes a generally cylindrical wall 941 extending between a front end 944 and a rear end 946, and defines an internal passageway 942 that receives the ratchet rod 903 therethrough. The outer cup seal 950 similarly includes a generally cylindrical wall 951 extending between a front end 954 and a rear end 953, and defines an internal passageway 955. The passageway 955 is concentrically aligned with passageway 942 in an exemplary embodiment. An annular circumferential groove 945 is formed on the exterior of the wall 941 of the inner plunger 940 which engages a complementary configured and arranged annular flange, such as rim 951, formed on the interior of the cylindrical wall 951 of the outer cup seal 950. The groove 945 and the rim 951 mate and interlock so as to lock the plunger 940 to the cup seal 950 via snap fit engagement to resist axial separation of the two components during use. In one embodiment, the rim 951 may be disposed on the rear end 953 of the sleeve member 950.

As best shown in FIG. 36, the inner cup-shaped plunger 940 includes one or more longitudinally extending slits 948 to assist with snapping and locking the pawl to the outer cup seal 950. The slits 948 define a plurality of circumferentially segmented and radially flexible portions or flanges 949 on the cylindrical wall 941, which permits the plunger 940 to be radially deformed inwards by contact with the outer cup seal 950 when snapping these two components together during assembly. When the rear end 953 of the cup seal 950 is slid over the front end 944 of the plunger 940, the annular rim 952 will engage and radially deform the segmented flanges 949 inwards temporarily until the rim 952 axially aligns with the annular groove 945 on the plunger 940. The segmented flanges 949 will then spring radially outwards to engage the rim 952 with the groove 945 to lock the plunger 940 and the cup seal 950 together thereby completing assemblage of the plunger assembly 930. The inner plunger 940 is removably insertable into the cup seal 950 and interlocked thereto via the foregoing annular rim and the groove system.

The frusto-conical cup-shapes of the plunger 940 and the cup seal 950 enable the nested assemblage of the plunger assembly 930. Accordingly, in one embodiment, the cylindrical walls 941, 951 of the inner plunger 940 and the outer cup seal 950 may be sloped in an axially forward direction to gradually narrow in diameter from the rear ends 946, 953 to the front ends 944, 954 of each, respectively. This allows the front end 946 of the inner plunger 940 to be slid into the rear end 953 of the outer cup seal 950.

Referring to FIGS. 27 and 36-38, the outer cup seal 950 provides an axially movable and generally transverse-oriented end wall that seals the proximal or rear end of the reservoir 708 to prevent or minimize leakage of the oral care fluid stored in the reservoir 708 rearward beyond the plunger assembly 930. The cup seal 950 forms a seal around both the ratchet rod 903 and the interior wall of dispenser housing 701, thereby forming a movable hermetically sealed tranverse end wall of the reservoir 708. In addition, the cup seal 950 protects and isolates the inner plunger 940 and the pawl 943 from the reservoir 708 and the oral care product contained therein to preserve proper operation of the ratchet mechanism and to prevent contamination of the reservoir.

The front end 954 of the cup seal 950 has a forward opening 956 that is sized and configured to form a relatively tight seal around the ratchet rod 903, but not so tight as to prevent the rod from sliding through the opening 956. This forms a slidable annular seal around the ratchet rod 903 that is intended to keep an excessive amount of oral care fluid or product from entering the passageway 955 of the cup seal 950. In one embodiment, the opening 956 includes an angled annular inner sealing surface 957 that closely matches the configuration, orientation, and angle of the angled teeth 904 of the ratchet rod 903. The sealing surface 957 thus slopes rearward and inward toward the ratchet rod 903 to define a frusto-conical shaped sealing surface. When the fluid dispensing system is not activated as shown in FIG. 38, at least a portion of the sealing surface 957 engages the mating angles surfaces of the ratchet rod teeth 904 to resist or prevent leakage along the rod into the rear of the dispenser housing 701. In one embodiment, the sealing surface 957 is preferably circumferentially continuous without any openings therein to eliminate potential leakage paths.

In addition to sealing, the configuration and placement of inner sealing surface 957 also functions to wipe and clean the oral care fluid or product from the ratchet rod 903 as it moves rearward through the forward opening 956 of the cup seal 950 as further explained herein. This reduces or eliminates any accumulation of the oral care product rearward of the plunger assembly 930 to preserve full movement and functionality of the push button actuator 920. In addition, accumulation or deposits of the product on the ratchet rod teeth 904 may reduce or prevent providing an audible click to the user when the oral care product is dispensed since such deposits tend to muffle the click sound. This audible indication that the ratcheting and fluid dispensing mechanism is functioning properly is desirable especially since each advance of the ratchet rod 903 will deliver a measured amount of product to the user each time the button actuator 920 is pushed and released.

With continuing reference to FIGS. 27 and 36-38, the outer cylindrical wall 941 of the cup seal 950 is configured and sized to frictionally and slidably engage the interior wall of the dispenser housing 701 to seal along the interior wall of the housing. Accordingly, in some embodiments, the outside diameter of at least a portion of the cylindrical wall 941 of the cup seal 950 is sized to be slightly larger than the inside diameter of the dispenser housing 701 in the reservoir 708 to provide a snug, but slideable fit. In one embodiment, a rear portion of the cup seal 950 proximate to the rear end 953 may be sized and configured to slidably engage the housing 701 thereby defining an annular outer sealing surface 958 that provides a seal between the cup seal 950 and an inner surface or wall of the dispenser housing 701. In the embodiment shown, intermediate and front portions forward of the sealing surface 958 may be smaller in diameter to avoid engagement with the interior of dispenser housing 701. This facilitates inserting the plunger assembly 930 into the open rear or proximal end of the housing 701 of the dispenser 700 during manufacturing.

In one embodiment, the outer cup seal 950 is preferably made of a plastic material having a relatively low coefficient of friction to facilitate smooth sliding engagement with the interior surface of the dispenser housing 701 and the material selected for the housing. In one embodiment, without limitation, the housing 701 may be made of polypropylene. The cup seal 950 may be made of low density polyethylene in some embodiments which provides good sliding performance when paired with a polypropylene material for the housing 701. Other suitable materials may be substituted so long as the cup seal 950 may slide smoothly within the dispenser housing 701.

Figure 39:
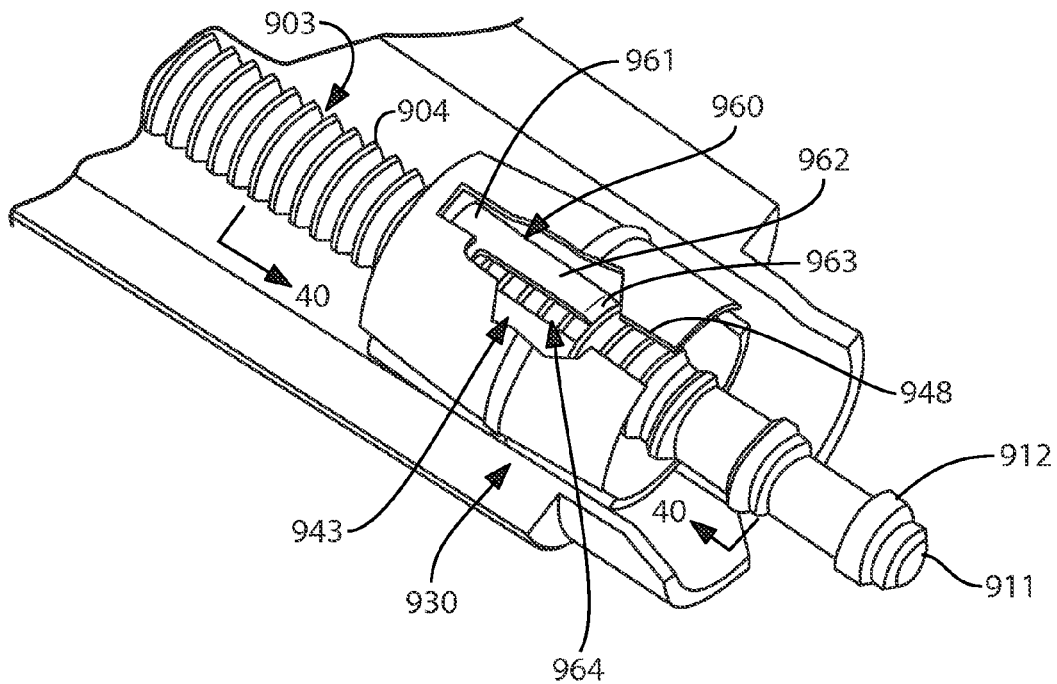
FIG. 39 is partial perspective view inside a portion of the internal reservoir of the dispenser of FIG. 16 showing the ratcheting fluid dispensing system including the ratchet rod and plunger assembly with pawl.
Figure 40:
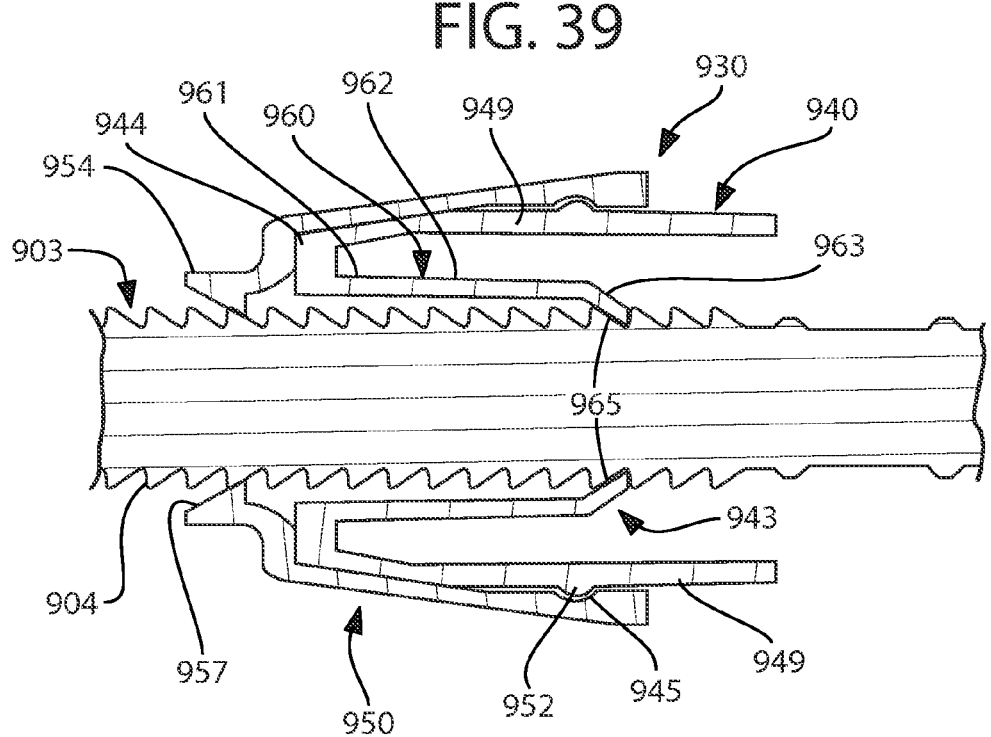
FIG. 40 is a cross-sectional view taken along line 40-40 in FIG. 39 showing the ratchet rod and plunger assembly in greater detail.

FIGS. 39 and 40 show the plunger assembly 930 in further detail. FIG. 39 is a perspective view of the plunger assembly 930 with a portion of the outer cup seal 950 removed to better show the plunger 948 therein. FIG. 40 shows a close up cross-sectional view of the plunger assembly 930 and the ratchet rod 903 disembodied from the dispenser 700 for clarity.

Referring now to FIGS. 27 and 36-40, the plunger assembly 930 further includes an internal pawl 943 which is configured to operably engage the ratchet rod 903 to produce the uni-directional ratcheting type action of the fluid dispensing system. The plunger 940 is disposed proximate to and enagageable with the ratchet rod 903. In one embodiment, the pawl 943 may be formed as an integral part of the plunger 940, or alternatively as a separate component mounted to the plunger. With particular reference to FIGS. 39 and 40 showing the pawl portion of the plunger 940 in greater detail, the pawl 943 preferably may be disposed at least partially within the internal passageway 942 of the plunger 940, and in some embodiments completely within passageway 940. As opposed to locating the pawl 943 outside of plunger assembly 930 in direct contact with the oral care product contained within the reservoir 708 of the dispenser 700, isolation of the pawl inside outer cup seal 950 advantageously protects the pawl from becoming embedded or encrusted in accumulations of the product that might otherwise interfere with proper operation of the pawl and production of the audible "click" sounds to the user when product is dispensed. The front end 954 of the cup seal 950 with its angled annular inner sealing surface 957 shields the pawl 943 from the oral care product due to its wiping action on the ratchet rod 903 as the rod travels back in through the plunger assembly 930 after dispensing product as further described herein, thereby preventing or at least minimizing any accumulations of the product on the pawl 943.

Referring to FIGS. 27 and 36-40, in one embodiment, the pawl 943 may be formed by a plurality of circumferentially spaced apart cantilevered and elastically flexible tines 960 projecting rearwards along longitudinal axis A-A from a central hub 961 disposed on the front end 944 of the plunger 940. The hub 961 may be an integral portion of the front end 944 of the plunger 940 and formed by a circumferentially continuous cylindrical wall. The tines 960 may each have a generally flattened configuration with a generally rectilinear lateral cross section preferably having a cross-sectional width larger than a cross-sectional height. The tines 960 each include an axially elongated body portion 962 terminating in an angled engaging end portion 963 terminated with a barb or tip 965 engaged with the teeth 704 of the ratchet rod 703 (see, e.g. FIGS. 39 and 40). The body portion 962 may be oriented substantially parallel to the cylindrical wall 949 of the plunger 940 and the ratchet rod 93. The engaging end portion 963 is angled and sloped radially inwards towards the ratchet rod 703 being disposed an angle to the body portion 962 and the cylindrical wall 949 of the plunger 940. The longitudinally-extending slots 964 formed between adjacent tines 960 make the tines flexible and movable in a radial direction with respect to the ratchet rod 904. The tines 960, and more particularly the tips 965 of the end engaging portion 963, are self-biased into full engagement with the angled teeth 904 of the ratchet rod 903 to produce uni-directional ratcheting action as further described herein.

The pawl 943 may preferably include at least two tines 960, and more preferably three or four tines circumferentially arranged around the central hub 961 to provide relatively uniform and secure engagement with the ratchet rod 904 around its entire circumference. In one exemplary embodiment, the pawl 943 may have four tines 960 to evenly distribute the engagement forces between the tines and rod 904 onto each quadrant of the ratchet rod 904 (i.e. top, bottom, and both opposite sides when viewed from the ends) to promote smooth operation of the ratchet mechanism and positive engagement between the tines and rod.

Referring to FIGS. 39 and 40, it should be noted that an alternative embodiment of the interlocking mechanism between the plunger 940 and the outer cup seal 950 is shown. In lieu of the arrangement shown in FIG. 38 wherein the cup seal 950 has a protruding annular rim 952 that engages the annular groove 945 formed on the plunger 940, the opposite arrangement is shown in FIGS. 39 and 40. Accordingly, it will be appreciated that either arrangement is suitable and the invention is not limited by one arrangement alone.

In contrast to monolithic or one-piece plungers, the two-piece plunger assembly 930 disclosed herein advantageously allows the material selection to be optimized for both the inner plunger 940 with the ratchet 943 and the outer cup seal 950 based upon their different functional or operating requirements. For example, the plastic material selected for forming the outer cup seal 950 preferably has characteristics of a relatively low coefficient of friction when used with the dispenser housing 701 and the ratchet rod 703 to provide smooth sliding engagement and operation of the ratchet mechanism and plunger assembly. In one exemplary embodiment, for example, the cup seal 950 may be made of homopolymer low density polyethylene such as LDPE 9931 available from The Dow® Chemical Company of Midland, Mich. or equivalent while the ratchet rod 903 and dispenser housing 701 may be made of polypropylene. LDPE 9931 has a typical nominal tensile strength (yield) of 1,500 psi, tensile modulus of 27,000 psi and flexural modulus of 46,000 psi providing the desired low coefficient of friction and ability to grip the interior surface of the dispenser housing 701. In one embodiment, the housing 701 may be a random copolymer polypropylene such as PP P5M6K-048 available from Flint Hills Resources® of Longview, Tex. or equivalent having a typical nominal tensile strength (yield) of 32 MPa (4,700 psi) and flexural modulus of 1050 MPa (153,000 psi).

By contrast, polypropylene or polyethylene are not necessarily optimum for the functions to be performed by the plunger 940, and particularly the integral pawl 943 which require a relatively harder and more rigid plastic having both stiffness and spring-like qualities. The pawl 943 is engaged by the ratchet rod 903 to advance the plunger 940 forward during the product dispensing stroke (requiring properties of axial rigidity), and then the pawl 943 performs the characteristic reciprocating flexing and "clicking" ratchet action (requiring elastic spring-like properties transverse to longitudinal axis LA) on the rearward return stroke of the rod when the rod slides back through the pawl while the plunger assembly maintains in stationary engagement with the dispenser housing 701 (operation further described herein). In one exemplary embodiment, the plunger 940 and the integral pawl 943 preferably may be made of an acetal copolymer such as Celcon® M90™ available from Ticona Engineering Polymers of Florence, Ky., or other plastics having similar properties. Celcon® M90™ has a nominal tensile strength (yield) of 66 MPa (9570 psi), tensile modulus of 2760 MPa (400,000 psi) and flexural modulus of 2550 MPa (370,000 psi) providing the desired spring-like and strength characteristics for the pawl 943 formed on the plunger 940. Accordingly, the benefits provided by the two-piece plunger assembly 930 allows material selection and optimization for the plunger 940 and the cup seal 950 based on the required functionality of each component.

It will be appreciated that other materials may be substituted for the foregoing exemplary materials included herein for illustrative purposes of possible preferred embodiments and not as limitations on material selection or the invention.

Figure 41:
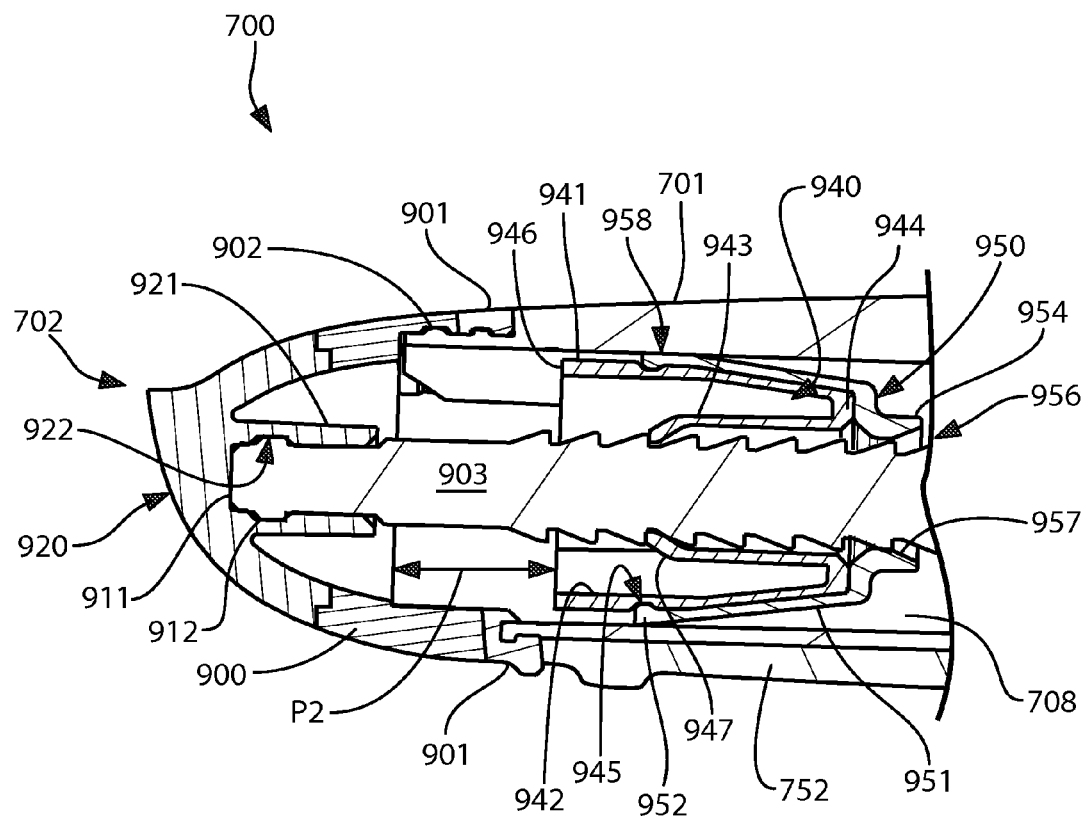
FIG. 41 is a partial cross sectional view of the proximal end of the dispenser thereof showing an alternative construction for the push button actuator in a released and inactivated un-depressed position.

Referring back again now to FIGS. 35-38, the push button actuator 920 is coupled to the ratchet rod 903 as previously described and operable to advance and retract the rod. In preferred exemplary embodiments, the actuator 920 may be formed of an elastically deformable and flexible material which may be either a separate component attached to part of the end cap 900 (see, e.g. FIG. 41), or alternatively the entire end cap 900 may be made completely of the elastically deformable material (see FIG. 38) with the actuator 920 being an integral flexible portion of the monolithic end cap. In some embodiments such as shown in FIG. 41 in which the actuator 920 is a separate component attached to the end cap 900, the actuator may be attached by any suitable mechanical method commonly used in the art including without limitation adhesives, press fit, interlocking component configurations, fasteners, ultrasonic or heat welding, or others. In this embodiment shown, the end cap includes 900 an annular seating surface 922 configured to receive and mount a portion of actuator 920 thereto. The end cap 900 may therefore be made of a relatively rigid plastic such as without limitation polypropylene or polyethylene instead of an elastomeric material which is preferred for the actuator 920 in some embodiments.

In either of the possible foregoing actuator constructions shown in FIGS. 38 and 41, the push actuator 920 preferably is made of a resilient and deformable material possessing sufficient elastic memory that allows the actuator to be depressed/deformed and then spring back to its original configuration. In one possible embodiment, without limitation, the push button actuator 920 may be made of TPE, rubber, or another similar deformable material having an elastic memory that allows the actuator to be deformed such as by applying pressure or force thereon with a user's finger or thumb and then return to its original configuration and position after the force is removed.

Beneficially, the resiliently flexible push button actuator 920 eliminates the need for separate biasing members or springs to return the actuator to its original undeformed configuration and position after activation. Accordingly, the actuator 920 incorporates the dual functionality of a push button actuator for the ratchet rod 903 and of a return spring in a single component, thereby conserving space within the housing 701 of the dispenser 700 which helps the dispenser to be made small enough to dock in the toothbrush handle 610 (see, e.g. FIGS. 17 and 18).

The foregoing dual functionality of the push button actuator 920 may be achieved in some embodiments by configuring the push button actuator to include a wall having an outwardly protruding generally convex or dome shape in the normal undeformed and unactuated position, as best shown in FIG. 27 or 38. In one embodiment, the actuator 920 is positioned on the end cap 900 to fall at least in part on the longitudinal axis A-A (coinciding with the axial centerline of the ratchet rod 903) so that pressing inward on the actuator applies a force having a line of action that preferably acts directly on and displaces the ratchet rod with respect to the housing 701 of the dispenser 700. As shown sequentially in FIGS. 27, 37, and 38 during activation of the push button actuator 920 by a user who applies axial force F shown in FIG. 37, the actuator is self-biased towards and will elastically return to the inactivated position shown in FIGS. 27 and 38 by its dome or convex shape when force F is removed.

In other possible embodiments contemplated, the actuator 920 may configured as an axially movable spring-biased button made of a relatively rigid or semi-rigid material and disposed on the proximal end 702 of the dispenser 700. In this case, a separate biasing member or spring is provided which acts on the actuator 920. Examples of such buttons are shown for example in U.S. Pat. No. 4,506,810, which is incorporated herein by reference in its entirety. Accordingly, the invention is not limited to any particular type of actuator 920 so long as the rod 903 may be axially advance in relation to the housing 701 of the dispenser 700.

Operation of the fluid dispensing system with ratcheting mechanism described herein will now be described. FIGS. 26 and 27 shows the ratcheting mechanism in an initial position. An oral care fluid or product is contained in the reservoir 708 of the dispenser 700. The ratchet rod 903 is in a first proximal non-dispensing and retracted position with respect to the proximal end 702 of the dispenser 700. The push button actuator 920 is in an inactivated condition or position with the actuator being undeformed. The plunger assembly 930 is shown in a first axial proximal position P1 being located near the proximal end 702 of the dispenser 700. This initial or first proximal position of the plunger assembly 930 establishes a first volumetric capacity for the reservoir 708 of the dispenser 700.

To dispense the oral care fluid or product, the user depresses the actuator 920 in an axial inward direction thereby applying a pressing or activation force F on the actuator as shown in FIG. 37. The force F acts in an axial direction against and opposite to the proximal or rearward spring biasing force of the self-biased push button actuator. Depressing the actuator 920 activates the dispensing system and the actuator 920 deforms axially as shown, wherein a portion of the actuator now assumes a relatively concave and inward flexed shape or configuration as shown. The ratchet rod 903, coupled to the actuator 920, concomitantly moves axially forward a short distance to a second temporary more distal and extended position than in FIG. 27 with respect to the proximal end 702 of the dispenser 700 (see directional arrow). The teeth 704 on the rod 703 engage the tines 960 of the pawl 943 in an abutting relationship. The tines 960 have sufficient structural stiffness in compression to avoid excessive flexing and slipping out of engagement with the teeth 704, thereby transmitting the force F to the rest of the plunger 940 and the outer cup seal 950 of the plunger assembly 930. This pushes and slides the entire plunger assembly 930 forward and more distally towards the dispensing end 703 of the dispenser 700. The plunger assembly 930 is now shown in a second axial distal position P2 being located farther away from the proximal operating end 702 of the dispenser 700. This second proximal position of the plunger assembly 930 establishes a second volumetric capacity for the reservoir 708 of the dispenser 700 that is less than the first volumetric capacity of the dispenser 700 shown in FIG. 27. The reduction in volumetric capacity results in the oral care fluid or product being dispensed through the applicator 709 on the distal end 703 of the dispenser, which is applied to the target oral surface.

Referring now to FIG. 38, the user next releases the push button actuator 920 after dispensing the product. The self-biasing spring force and elastic memory of the actuator 920 returns the actuator rearward or proximally to the inactivated condition or position as shown with the actuator being undeformed and convex in configuration again. The actuator 920 pulls and moves the ratchet rod 903 back rearward with it to the first proximal non-dispensing and retracted position with respect to the proximal end 702 of the dispenser 700, similar to that shown in FIG. 27 and described above. Although the ratchet rod 703 moves axially, the plunger assembly 930 remains stationary and engaged with the interior walls or surface of the dispenser housing 701 in position P2 as shown. The pawl 943 on the plunger 940 prevents rearward motion of the plunger assembly 930. The ratchet rod 903 slips through the flexible tines 960 of the pawl 943 which radially deflect and oscillate as the teeth 904 of the rod passes over the engaging end 963 portion of the tines. This produces a characteristic "clicking" sound of the ratchet mechanism which provides audible confirmation to the user that the dispenser has dispensed oral care product and is functioning properly.

When the ratchet rod 903 comes to rest, as shown in FIG. 38, the tines 960 remain engaged with the rod which is now ready to repeat the dispensing cycle in the foregoing manner already described, but this time beginning with the plunger assembly 930 in the axially farther advanced P2 position. During each subsequent dispensing cycle, the plunger assembly will continue to remain in a successively farther advanced position distally after each cycle until the reservoir 708 is essentially depleted of oral care fluid or product.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care system comprising:
   a toothbrush; and
   a dispenser detachably coupled to the toothbrush, the dispenser comprising:
     an internal reservoir containing a fluid; and
     a conduit in fluid communication with the reservoir and terminating in an orifice for dispensing the fluid from the reservoir; and
   a plug having an axis, a proximal plug portion disposed within the conduit, and a distal plug portion disposed within a socket of the toothbrush, wherein a first axial force is required to remove the proximal plug portion from the conduit of the dispenser and a second axial force is required to remove the distal plug portion from the socket of the toothbrush, the second axial force being greater than the first axial force;
   wherein the socket of the toothbrush is located within a cavity of the toothbrush in which at least a portion of the dispenser nests when detachably coupled to the toothbrush; and
   wherein the socket is formed in a transverse end wall that closes a distal end of the cavity.

2. The oral care system according to claim 1 wherein the plug further comprises a radially extending flange located between the proximal plug portion and the distal plug portion.

3. The oral care system according to claim 2 wherein the radially extending flange is an annular flange.

4. The oral care system according to claim 1 wherein the ratio of the second axial force to the first axial force is in a range of 1:1.5 to 1:6.

5. The oral care system according to claim 1 wherein the distal plug portion comprises one or more protrusions extending from an outer surface of the distal plug portion for frictionally engaging an inner surface of the socket.

6. The oral care system according to claim 5 wherein the one or more protrusions are a plurality of radially extending spaced-apart annular ribs.

7. The oral care system according to claim 1 wherein the proximal plug portion comprises a tapered end.

8. The oral care system according to claim 1 wherein the proximal plug portion comprises one or more voids.

9. The oral care system according to claim 8 wherein the proximal plug portion comprises a central void extending along the axis.

10. The oral care system according to claim 1 wherein the proximal plug portion seals the conduit when disposed therein.

11. The oral care system according to claim 1 wherein the distal plug portion and the proximal plug portion are axially aligned along the axis and are cylindrical in shape.

12. The oral care system according to claim 1 wherein upon application of the first axial force to the dispenser, the proximal plug portion slides out of the conduit and the distal plug portion remains disposed within the socket.

13. The oral care system according to claim 12 wherein the proximal plug portion can be repetitively slid into and out of the conduit by applying the first axial force without removing the distal plug portion from the socket.

14. The oral care system according to claim 1 wherein the plug assists with the detachable coupling of the dispenser to the toothbrush.

15. The oral care system according to claim 1 wherein the plug is non-unitary and non-integral with respect to the toothbrush and the dispenser.

16. The oral care system according to claim 1 wherein the plug further comprises a radially extending flange located between the proximal plug portion and the distal plug portion, wherein the ratio of the second axial force to the first axial force is in a range of 1:1.5 to 1:6, wherein the distal plug portion comprises one or more protrusions extending from an outer surface of the distal plug portion for frictionally engaging an inner surface of the socket, wherein the proximal plug portion comprises a central void extending along the axis, wherein the proximal plug portion seals the conduit when disposed therein, wherein the socket of the toothbrush is located within a cavity of the toothbrush in which at least a portion of the dispenser nests when the dispenser is detachably coupled to the toothbrush, wherein the distal plug portion and the proximal plug portion are axially aligned along the axis and are cylindrical in shape.

17. A method of manufacturing an oral care system comprising:
   a) providing a toothbrush having a socket;
   b) providing a dispenser having an internal reservoir containing a fluid and a conduit in fluid communication with the reservoir, the conduit terminating in an orifice for dispensing the fluid from the reservoir;
   c) inserting a proximal plug portion of a plug into the conduit, a distal plug portion of the plug extending from the dispenser; and
   d) detachably coupling the dispenser to the toothbrush by sliding the distal plug portion of the plug into the socket of the toothbrush.

18. The method according to claim 17 wherein step b) further comprises inserting the proximal plug portion into the conduit, flowing the fluid into the reservoir via an opening other than the orifice, and sealing the opening.

19. The method according to claim 17 wherein step d) further comprises nesting at least a portion of the dispenser within a cavity formed in the toothbrush, the socket located within the cavity.

20. The method according to claim 17, further comprising:
   e) removing the proximal plug portion from the conduit of the dispenser, the distal plug portion remaining positioned in the socket of the toothbrush.

21. The method according to claim 17 wherein the plug is non-unitary and non-integral with respect to the toothbrush and the dispenser.

22. A method of applying a fluid to an oral surface comprising:
   a) providing an oral care system comprising a toothbrush having a socket, a dispenser detachably coupled to the toothbrush, the dispenser comprising an internal reservoir containing a fluid and a conduit in fluid communication with the reservoir, the conduit terminating in an orifice for dispensing the fluid from the reservoir, and a plug having a proximal plug portion disposed within the conduit and a distal plug portion disposed within the socket of the toothbrush;
   b) detaching the dispenser from the toothbrush, the proximal plug portion sliding out of the conduit and the distal plug portion remaining in the socket of the toothbrush; and
   c) dispensing the fluid from the dispenser via the orifice directly onto the oral surface.

23. The method according to claim 22 further comprising:
   d) upon completion of step c), detachably re-coupling the dispenser to the toothbrush, the proximal plug portion sliding back into the conduit.

24. The method according to claim 22 wherein a first axial force is required to remove the proximal plug portion from the conduit of the dispenser and a second axial force is required to remove the distal plug portion from the socket of the toothbrush, the second axial force being greater than the first axial force.

* * * * *